US009139849B2

(12) United States Patent
Larionov et al.

(10) Patent No.: US 9,139,849 B2
(45) Date of Patent: Sep. 22, 2015

(54) RAPID GENERATION OF LONG SYNTHETIC CENTROMERIC TANDEM REPEATS FOR MAMMALIAN ARTIFICIAL CHROMOSOME FORMATION

(75) Inventors: Vladimir L. Larionov, Potomac, MD (US); William C. Earnshaw, Cingletie Peeples (GB); Reto Gassman, Zurich (CH); Stefanie Kandels-Lewis, Dielheim-Balzfeld (DE); Hiroshi Masumoto, Rockville, MD (US); Megumi Nakano, Rockville, MD (US); Vladimir Noskov, Rockville, MD (US); Natalay Y. Kouprina, Potomac, MD (US); Carl J. Barrett, Chapel Hill, NC (US); Stefano Cardinale, Edinburgh (GB)

(73) Assignees: The United States of America as Represented by the Government of the Department of Health and Human Services, Washington, DC (US); The University Court of the University of Edinburgh, Edinburg (GB)

( * ) Notice: Subject to any disclaimer, the term of this patent is extended or adjusted under 35 U.S.C. 154(b) by 1569 days.

(21) Appl. No.: 11/910,973

(22) PCT Filed: Apr. 7, 2006

(86) PCT No.: PCT/US2006/013362
§ 371 (c)(1),
(2), (4) Date: Oct. 8, 2007

(87) PCT Pub. No.: WO2006/110680
PCT Pub. Date: Oct. 19, 2006

(65) Prior Publication Data
US 2009/0136924 A1    May 28, 2009

Related U.S. Application Data

(60) Provisional application No. 60/669,589, filed on Apr. 8, 2005.

(51) Int. Cl.
*C12P 19/34* (2006.01)
*C12Q 1/68* (2006.01)
*C12N 15/85* (2006.01)

(52) U.S. Cl.
CPC .......... *C12N 15/85* (2013.01); *C12N 2800/204* (2013.01); *C12N 2800/206* (2013.01); *C12N 2800/208* (2013.01); *C12N 2830/003* (2013.01)

(58) Field of Classification Search
USPC ................ 435/6, 91.2, 252.3, 325, 91.4, 6.12
See application file for complete search history.

(56) References Cited

U.S. PATENT DOCUMENTS

| 4,464,472 | A | 8/1984 | Carbon et al. |
|---|---|---|---|
| 6,025,155 | A | 2/2000 | Hadlaczky et al. |
| 6,077,697 | A | 6/2000 | Hadlaczky et al. |
| 6,322,781 | B1 * | 11/2001 | McCutchen ................ 424/93.2 |
| 6,331,397 | B1 | 12/2001 | Schindelhauer et al. |
| 6,743,967 | B2 | 6/2004 | Hadlaczky et al. |
| 2002/0076811 | A1 | 6/2002 | Okazaki et al. |
| 2003/0064509 | A1 | 4/2003 | Marynen et al. |
| 2003/0082559 | A1 * | 5/2003 | Beach et al. ....................... 435/6 |
| 2003/0124555 | A1 | 7/2003 | Brasch et al. |
| 2003/0148988 | A1 | 8/2003 | Kool |
| 2004/0245317 | A1 | 12/2004 | Larionov et al. |
| 2006/0185025 | A1 | 8/2006 | Oshimura et al. |

FOREIGN PATENT DOCUMENTS

| WO | WO 95/03400 | 2/1995 |
|---|---|---|
| WO | WO 00/18941 | 4/2000 |
| WO | WO 01/77357 | 10/2001 |
| WO | WO 03/029430 | 4/2003 |
| WO | WO 03/057849 | 7/2003 |
| WO | WO 2004/058987 | 7/2004 |
| WO | WO 2005/003389 | 1/2005 |
| WO | WO 2005/014786 | 2/2005 |

OTHER PUBLICATIONS

Ebersole et al., "Rapid generation of long synthetic tandem repeats and its application for analysis in human artificial chromosome formation," *Nucleic Acids Research* 33(15): online publication, 2005.
Ohzeki et al., "CENP-B box is required for de novo centromere chromatin assembly on human alphoid DNA," *Journal of Cell Biology* 159(5): 765-775, 2002.
Harrington et al., "Formation of de novo centromeres and construction of first-generation human artificial microchromosomes," *Nature Genetics* 15(4): 345-355, 1997.
Smirnov et al., "Method for manufacturing whole-genome microarrays by rolling circle amplification," *Genes Chromosomes & Cancer* 40(1): 72-77, 2004.
Dean et al., "Rapid amplification of plasmid and phage DNA using Phi29 DNA polymerase and multiply-primed rolling circle amplification," *Genome Research* 11(6): 1095-1099, 2001.
Masumoto et al., "The role of CENP-B and alpha-satellite DNA: de novo assembly and epigenetic maintenance of human centromeres," *Chromosome Research* 12(6): 543-556, 2004.

(Continued)

*Primary Examiner* — Kenneth R. Horlick
*Assistant Examiner* — Joyce Tung
(74) *Attorney, Agent, or Firm* — Klarquist Sparkman, LLP

(57) ABSTRACT

Methods are described for construction of long synthetic arrays of DNA repeats, such as alphoid repeats or other repeat sequences. The methods include concatamerization of DNA into short repeats (for instance using rolling circle amplification or directional in vitro ligation), followed by assembling the short repeats into long arrays by homologous recombination during transformation into microbe cells. These methods can be described generally as Recombinational Amplification of Repeats (RAR). The long arrays are engineered centromere-like regions that allow one to construct mammalian artificial chromosomes with a predefined centromeric region structure. Artificial chromosomes, including human artificial chromosomes with a regulated centromere, and methods of their use are also provided.

18 Claims, 11 Drawing Sheets

(56) References Cited

OTHER PUBLICATIONS

Amersham Product Booklet for TempliPhi 100 Amplification Kit & TempliPhi 500 Amplification Kit (Product Codes 25-6400-10 and 25-6400-50) *Amersham Biosciences*, 27 sheets, 2002.
Amersham Product Booklet for TempliPhi DNA Sequencing Template Amplification Kit (Product code 25-64001-01) *Amersham Biosciences*, 14 sheets, 2002.
Pages 53-71, Abstract book for 2004 International Meeting of the Federation of Korean Microbiological Societies.
Chromos Molecular Systems Inc., Company Profile, 15 pages; accessed on-line on or around Mar. 7, 2005.
GenBank Accession U5114 (GI:1817729) Cloning Vector pBAC108L; Feb. 6, 1997 (downloaded Mar. 31, 2005; 3 pages).
GenBank Accession D29750 (BI:550080) Human DNA, alpha satellite in centromeric region of chromosome 21; May 29, 2002 (downloaded Apr. 6, 2005; 2 pages).
Alsmadi et al., "High accuracy genotyping directly from genomic DNA using a rolling circle amplification based assay," *BMC Genomics*, 4:21-39 (2003).
Annab et al., "Isolation of a functional the human BRCA1 gene by transformation-associated recombination in yeast," *Gene*, 250:201-208 (2000).
Baron et al., "Tet Repressor-Based System for Regulated Gene Expression in Eukaryotic Cells: Principles and Advances," *Methods in Enzymology*, 327:401-421 (2000).
Basu et al., "Efficient assembly of de novo human artificial chromosomes from large genomic loci," *BMC Biotechnology*, 5:21 (2005).
Basu et al., "Rapid creation of BAC-based human artificial chromosome vectors by transposition with synthetic alpha-satellite arrays," *Nucleic Acids Research*, 33:587-596 (2005).
Bradshaw et al., "A long-range regulatory element of *Hoxc8* identified by using the pClasper vector," *Proc. Natl. Acad. Sci. USA*, 93:2426-2430 (1996).
Bradshaw et al., "A new vector for recombination-based cloning of large DNA fragments from yeast artificial chromosomes," *Nucleic Acids Research*, 23:4850-4856 (1995).
Burke et al., "Cloning of Large Segments of Exogenous DNA into Yeast by Means of Artificial Chromosome Vectors," *Science*, 236:806-812 (1987).
Cancilla et al., "Direct Cloning of Human 10q25 Neocentromere DNA Using Transformation-Associated Recombination (TAR) in Yeast," *Genomics*, 47:399-404 (1998).
Collins et al., "De Novo Kinetochore Assembly Requires the Centromeric Histone H3 Variant$^D$," *Molecular Biology of the Cell*, 16:5649-5660 (2005).
Erickson et al., "Direct Cloning of Yeast Genes from an Ordered Set of Lambda Clones in *Saccharomyces cerevisiae* by Recombination in Vivo," *Genetics*, 134:151-157 (1993).
Grimes et al., "Engineering mammalian chromosomes," *Human Molecular Genetics*, 7:1635-1640 (1998).
Grimes et al., "α-Satellite DNA and Vector Composition Influence Rates of Human Artificial Chromosome Formation," *Molecular Therapy*, 5:798-805 (2002).
Humble et al., "Radial Transformation-Associated Recombination Cloning from the Mouse Genome: Isolation of Tg.AC Transgene with Flanking DNAs," *Genomics*, 70:292-299 (2000).
Kerkhof, "A Comparison of Substrates for Quantifying the Signal from a Nonradiolabeled DNA Probe," *Analytical Biochemistry*, 205:359-364 (1992).
Ketner et al., "Efficient manipulation of the human adenovirus genome as an infectious yeast artificial chromosome clone," *Proc. Natl. Acad. Sci., USA*, 91:6186-6190 (1994).
Kim et al., "Discovery of a Novel, Paternally Expressed Ubiquitin-specific Processing Protease Gene through Comparative Analysis of an Imprinted Region of Mouse Chromosome 7 and Human Chromosome 19q13.4," *Genome Research*, 10:1138-1147 (2000).
Kouprina et al., "A Model System to Assess the Integrity of Mammalian YACs during Transformation and Propagation in Yeast," *Genomics*, 21:7-17 (1994).

Kouprina et al., "Construction of Human Chromosome 16- and 5-Specific Circular YAC/BAC Libraries by in Vivo Recombination in Yeast (TAR Cloning)," *Genomics*, 53:21-28 (1998).
Kouprina et al., "Integrity of Human YACs during Propagation in Recombination-Deficient Yeast Strains," *Genomics*, 56:262-273 (1999).
Kouprina et al., "Cloning of human centromeres by transformation-associated recombination in yeast and generation of functional human artificial chromosomes," *Nucleic Acids Research*, 31:922-934 (2003).
Kouprina et al., "Exploiting the yeast *Saccharomyces cerevisiae* for the study of the organization and evolution of complex genomes," *FEMS Microbiology Reviews*, 27:629-649 (2003).
Kouprina et al., "TAR cloning: insights into gene function, long-range haplotypes and genome structure and evolution," *Nature Reviews-Genetics*, 7(10):805-812 (2006).
Larin et al., "Advances in human artificial chromosome technology," *Trends in Genetics*, 18:313-319 (2002).
Larionov et al., "Direct isolation of human *BRCA2* gene by transformation-associated recombination in yeast," *Proc. Natl. Acad. Sci. USA*, 94:7384-7387 (1997).
Larionov et al., "Highly selective isolation of human DNAs from rodent-human hybrid cells as circular yeast artificial chromosomes by transformation-associated recombination cloning," *Proc. Natl. Acad. Sci. USA*, 93:13925-13930 (1996).
Larionov et al., "Recombination during transformation as a source of chimeric mammalian artificial chromosomes in yeast (YACs)," *Nucleic Acids Research*, 22:4154-4162 (1994).
Larionov et al., "Specific cloning of human DNA as yeast artificial chromosomes by transformation-associated recombination," *Proc. Natl. Acad. Sci. USA*, 93:491-496 (1996).
Larionov et al., "Transformation-associated Recombination between Diverged and Homologous DNA Repeats is Induced by Strand Breaks,", *Yeast*, 10:93-104 (1994).
Lipps et al., "Chromosome-based vectors for gene therapy," *Gene*, 304:23-33 (2003).
Ma et al., "Plasmid construction by homologous recombination in yeast," *Gene*, 58:201-216 (1987).
Masumoto et al., "Assay of centromere function using a human artificial chromosome," *Chromosoma*, 107:406-416 (1998).
Mejía et al., "Efficiency of de Novo Centromere Formation in Human Artificial Chromosomes," *Genomics*, 79:297-304 (2002).
Mézard et al., "Recombination between Similar but Not Identical DNA Sequences during Yeast Transformation Occurs within Short Stretches of Identity," *Cell*, 70:659-670 (1992).
Myung et al., "SGS1, the *Saccharomyces cerevisiae* homologue of BLM and WRN, suppresses genome instability and homologous recombination," *Nature Genetics*, 27:113-116 (2001).
Nakano et al., "Epigenetic assembly of centromeric chromatin at ectopic α-satellite sites on human chromosomes," *Journal of Cell Science*, 116:4021-4034 (2003).
Nakashima et al., "Assembly of additional heterochromatin distinct from centromere-kinetochore chromatin is required for de novo formation of human artificial chromosome," *Journal of Cell Science*, 118:5885-5598 (2005).
Noskov et al., "A general cloning system to selectively isolate any eukaryotic or prokaryotic genomic region in yeast," *BMC Genomics*, 4:16-26 (2003).
Noskov et al., "A genetic system for direct selection of gene-positive clones during recombinational cloning in yeast," *Nucleic Acids Research*, 30(2) e8 (7 pages) (2002).
Osoegowa et al., "A Bacterial Artificial Chromosome Library for Sequencing the Complete Human Genome," *Genome Research*, 11:483-496 (2001).
Poddar et al., "Two Complexes of Spindle Checkpoint Proteins Containing Cdc20 and Mad2 Assemble during Mitosis Independently of the Kinetochore in *Saccharomyces cerevisiae*," *Eukaryotic Cell*, 4:867-878 (2005).
Pompon et al., "Protein engineering by cDNA recombination in yeasts: shuffling of mammalian cytochrome P-450," *Gene*, 83:15-24 (1989).
Prado et al., "New in-vivo cloning methods by homologous recombination in yeast," *Current Genetics*, 25:180-183 (1994).

(56) References Cited

OTHER PUBLICATIONS

Qin et al., "Site-specific cleavage of chromosome in vitro through Cre-*lox* recombination," *Nucleic Acids Research*, 23:1923-1927 (1995).

Saffery et al., "Strategies for engineering human chromosomes with therapeutic potential," *The Journal of Gene Medicine*, 4:5-13 (2002).

Schlessinger, "Yeast artificial chromosomes: tools for mapping and analysis of complex genomes," *Trends in Genetics*, 6:248-258 (1990).

Schneider et al., "pMPY-ZAP: A Reusable Polymerase Chain Reaction-directed Gene Disruption Cassette for *Saccharomyces cerevisiae*," *Yeast*, 12:129-134 (1996).

Shen et al., "Homologous Recombination in *Escherichia coli*: Dependence on Substrate Length and Homology," *Genetics*, 112:441-457 (1986).

Shizuya et al., "Cloning and stable maintenance of 300-kilobase-pair fragments of human DNA in *Escherichia coli* using an F-factor-based vector," *Proc. Natl. Acad. Sci. USA*, 89:8794-8797 (1992).

Spencer et al., "Targeted Recombination-Based Cloning and Manipulation of Large DNA Segments in Yeast," *Methods: A Comparison in Methods in Enzymology*, 5:161-175 (1993).

Stinchcomb et al., "Eukaryotic DNA segments capable of autonomous replication in yeast," *Proc. Natl. Acad. Sci. USA*, 77:4559-4563 (1980).

Sun et al., "Human artificial episomal chromosomes for cloning large DNA fragments in human cells," *Nature Genetics*, 8:33-41 (1994).

Toniatti et al., "Gene therapy progress and prospects: transcription regulatory systems," *Gene Therapy*, 11:649-657 (2004).

Wach et al., "New Heterologous Modules for Classical or PCR-based Gene Disruptions in *Saccharomyces cerevisiae*," *Yeast*, 10:1793-1808 (1994).

Watt et al., "Homology requirements for recombination in *Escherichia coli*," *Proc. Natl. Acad. Sci. USA*, 82:4768-4772 (1985).

\* cited by examiner

● : CENP-B box
○ : pseudo CENP-B box
→ : alphoid monomer
E : EcoR I 2-mer, 4-mer and 5-mer were used for RCA amplification.

FIG. 3A
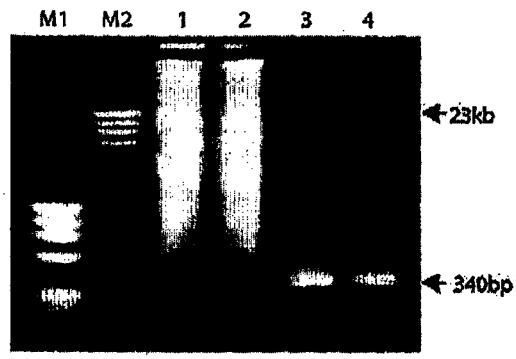
FIG. 3B
FIG. 3C
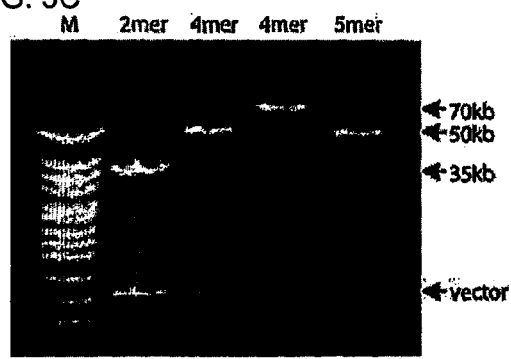
FIG. 3D
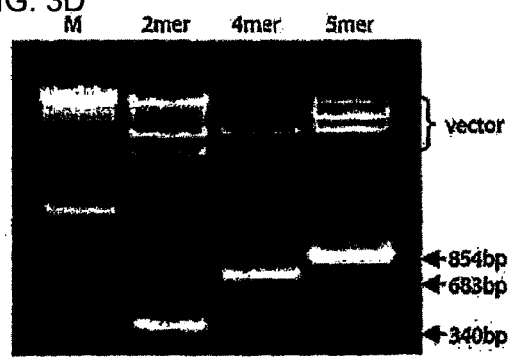
FIG. 4A
FIG. 4B
FIG. 4C  4mer
2mer
FIG. 4D  5mer
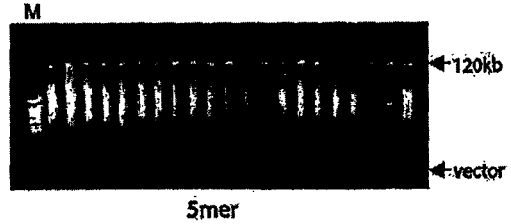
5mer

FIG. 6A

```
                        10         20         30         40         50         60
consensus       CATTCTCAGAAACTTCTTTGTGATGTGTGCATTCAACTCACAGAGTTGAACCTTCCTTTT
chr. 17 alphoid CATTCACAGAAAACTCTTGGTGACGACTGAGTTTAACTCACAGAGCTGAACATTCCTTTG
alphoid + tetO  CATTCTGAGAAACTTCTTTGTGATGTTTGCATTCAACTCACAGAGTTGAACATTCCTTTT 70         80         90        100        110        120
consensus       CATAGAGCAGTTTTGAAACACTCTTTTTGTAGAAT-CTGCAAGTGGATATTTGGACCGCT
chr. 17 alphoid GATGGAGCAGTTTCGAAACACACTATTTGTAGAAT-GTGCAAGTGGATATTTAGGCCTCT
alphoid + tetO  CATTGAGCAGTTTGGAAACACTCTTTTTGTAGAATCCTGCAAGTGGGAGTTTACCACTCG CENP-B box      150        160        170
consensus       TTGAGGC............ATATCTTCATATAAAAACTAGACAGAAG
chr. 17 alphoid CTGAGGATTTCGTTGGAAACGGGATAAACCGCACA---GAACTAAACAGAAG
alphoid + tetO  CTATCAGTGATAGAAAAGTGAAAGTTCTTCACATAAAAACTAGACAGAAG
                             tet operator
```

FIG. 6B

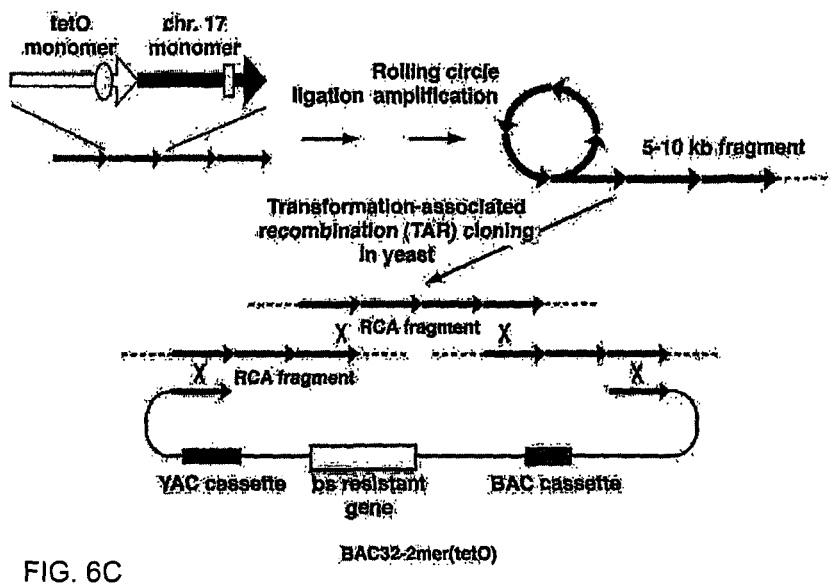

FIG. 6C

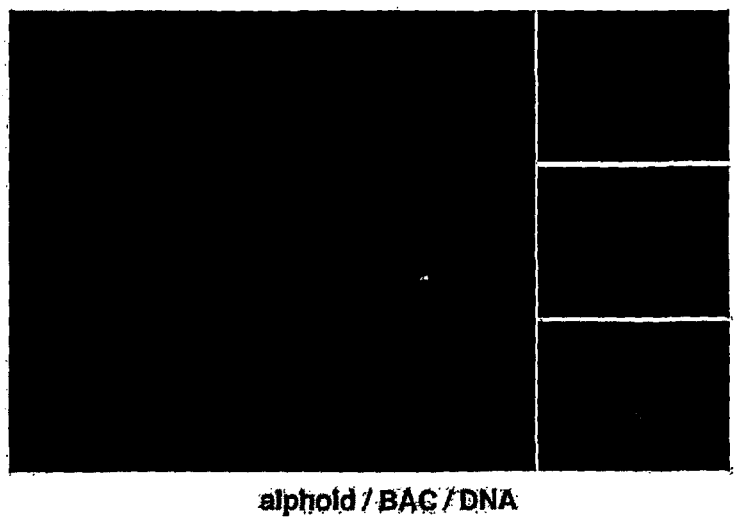

alphoid / BAC / DNA

DNA

HAC

5 µm

5 µm

HAC
microtubules
DNA

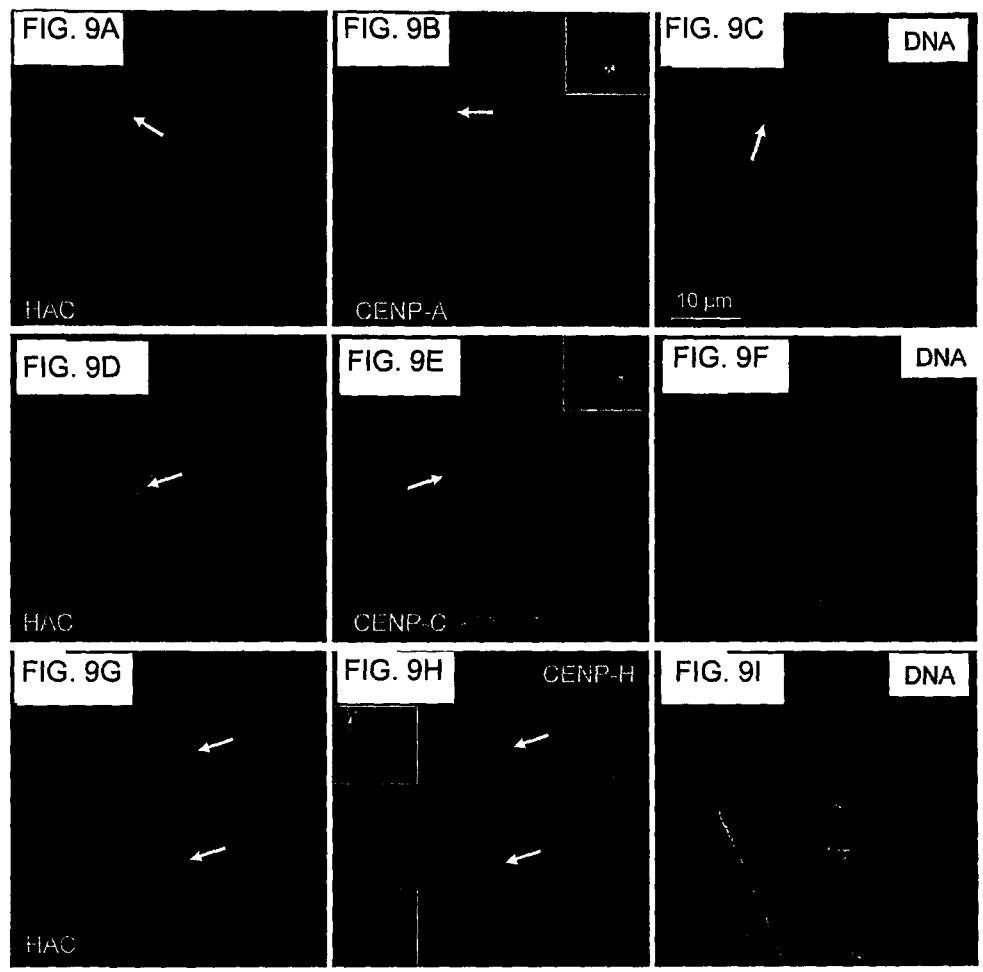
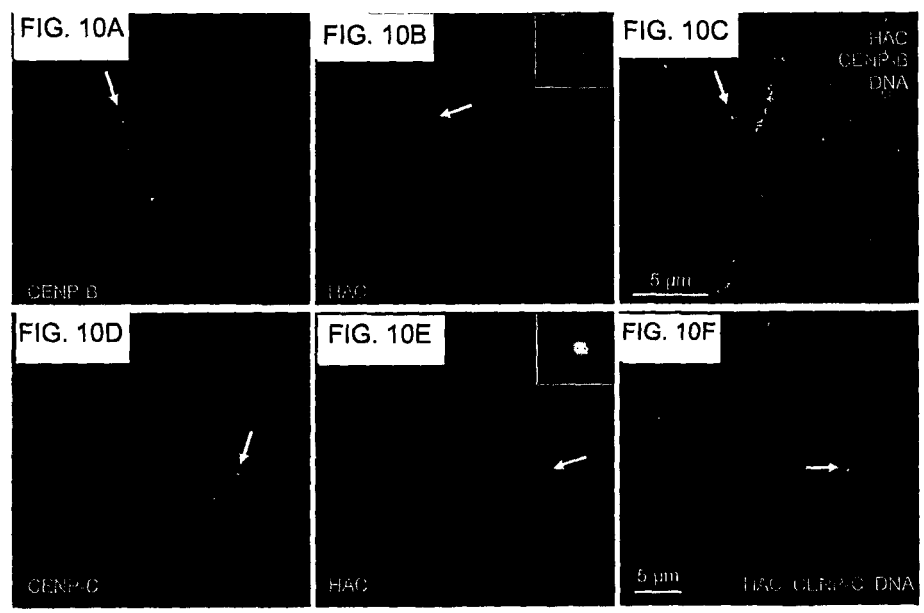

number of HACs per nucleus

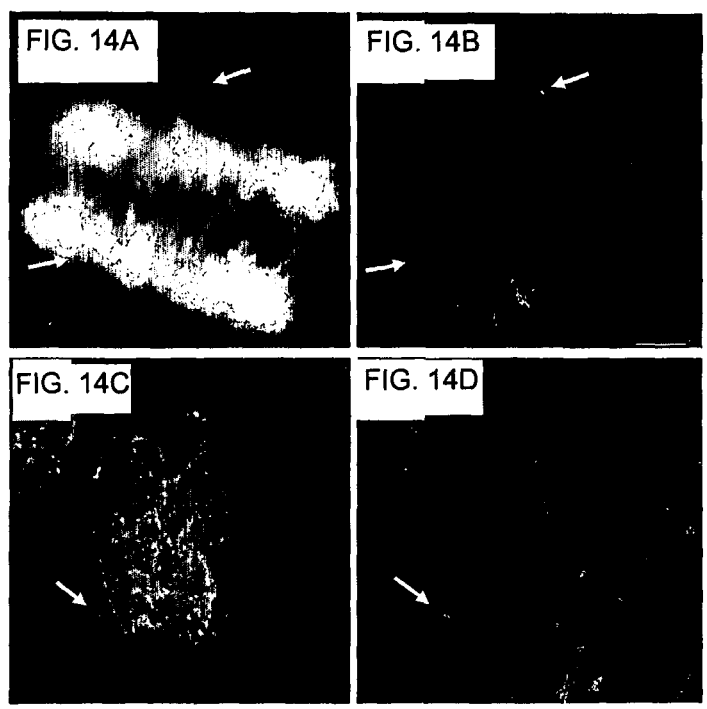

```
                        SEQUENCE LISTING

<160> NUMBER OF SEQ ID NOS: 51

<210> SEQ ID NO 1
<211> LENGTH: 8
<212> TYPE: DNA
<213> ORGANISM: Artificial sequence
<220> FEATURE:
<223> OTHER INFORMATION: upper strand RCA primer for alphoid DNA

<400> SEQUENCE: 1 aatctgca                                                              8

<210> SEQ ID NO 2
<211> LENGTH: 8
<212> TYPE: DNA
<213> ORGANISM: Artificial sequence
<220> FEATURE:
<223> OTHER INFORMATION: upper strand RCA primer for alphoid DNA

<400> SEQUENCE: 2 actagaca                                                              8

<210> SEQ ID NO 3
<211> LENGTH: 8
<212> TYPE: DNA
<213> ORGANISM: Artificial sequence
<220> FEATURE:
<223> OTHER INFORMATION: upper strand RCA primer for alphoid DNA

<400> SEQUENCE: 3 acagagtt                                                              8

<210> SEQ ID NO 4
```

```
<211> LENGTH: 8
<212> TYPE: DNA
<213> ORGANISM: Artificial sequence
<220> FEATURE:
<223> OTHER INFORMATION: lower strand RCA primer for alphoid DNA

<400> SEQUENCE: 4 agagtgtt                                                                   8

<210> SEQ ID NO 5
<211> LENGTH: 8
<212> TYPE: DNA
<213> ORGANISM: Artificial sequence
<220> FEATURE:
<223> OTHER INFORMATION: lower strand RCA primer for alphoid DNA

<400> SEQUENCE: 5 tctgagaa                                                                   8

<210> SEQ ID NO 6
<211> LENGTH: 8
<212> TYPE: DNA
<213> ORGANISM: Artificial sequence
<220> FEATURE:
<223> OTHER INFORMATION: lower strand RCA primer for alphoid DNA

<400> SEQUENCE: 6 ggcctcaa                                                                   8

<210> SEQ ID NO 7
<211> LENGTH: 9
<212> TYPE: DNA
<213> ORGANISM: Artificial sequence
<220> FEATURE:
<223> OTHER INFORMATION: upper strand primer for the mouse major
      satellite

<400> SEQUENCE: 7 acttgacga                                                                  9

<210> SEQ ID NO 8
<211> LENGTH: 10
<212> TYPE: DNA
<213> ORGANISM: Artificial sequence
<220> FEATURE:
<223> OTHER INFORMATION: upper strand primer for the mouse major
      satellite

<400> SEQUENCE: 8
tgcacactga                                                                10

<210> SEQ ID NO 9
<211> LENGTH: 10
<212> TYPE: DNA
<213> ORGANISM: Artificial sequence
<220> FEATURE:
<223> OTHER INFORMATION: lower strand primer for the mouse major
      satellite

<400> SEQUENCE: 9
ttagaaatgt                                                                10

<210> SEQ ID NO 10
<211> LENGTH: 10
<212> TYPE: DNA
<213> ORGANISM: Artificial sequence
<220> FEATURE:
```

```
<223> OTHER INFORMATION: lower strand primer for the mouse major
      satellite

<400> SEQUENCE: 10
gaatatggcg                                                              10

<210> SEQ ID NO 11
<211> LENGTH: 8
<212> TYPE: DNA
<213> ORGANISM: Artificial sequence
<220> FEATURE:
<223> OTHER INFORMATION: an upper strand primer for the mouse minor
      satellite

<400> SEQUENCE: 11 aatgagtt                                                                 8

<210> SEQ ID NO 12
<211> LENGTH: 15
<212> TYPE: DNA
<213> ORGANISM: Artificial sequence
<220> FEATURE:
<223> OTHER INFORMATION: an upper strand primer for the mouse minor
      satellite

<400> SEQUENCE: 12
ttcgttggaa acggg                                                        15

<210> SEQ ID NO 13
<211> LENGTH: 9
<212> TYPE: DNA
<213> ORGANISM: Artificial sequence
<220> FEATURE:
<223> OTHER INFORMATION: lower strand primer for the mouse minor
      satellite

<400> SEQUENCE: 13 agtgtggtt                                                                9

<210> SEQ ID NO 14
<211> LENGTH: 9
<212> TYPE: DNA
<213> ORGANISM: Artificial sequence
<220> FEATURE:
<223> OTHER INFORMATION: upper strand primer for the human gamma-8
      satellite

<400> SEQUENCE: 14 aattctggg                                                                9

<210> SEQ ID NO 15
<211> LENGTH: 8
<212> TYPE: DNA
<213> ORGANISM: Artificial sequence
<220> FEATURE:
<223> OTHER INFORMATION: lower strand primer for the human gamma-8
      satellite

<400> SEQUENCE: 15 ccagaatt                                                                 8

<210> SEQ ID NO 16
<211> LENGTH: 8
<212> TYPE: DNA
<213> ORGANISM: Artificial sequence
<220> FEATURE:
<223> OTHER INFORMATION: lower strand primer for the human gamma-8
``` satellite

<400> SEQUENCE: 16 gacacctc                                                                      8

<210> SEQ ID NO 17
<211> LENGTH: 8
<212> TYPE: DNA
<213> ORGANISM: Artificial sequence
<220> FEATURE:
<223> OTHER INFORMATION: upper strand primer for the human Alu repeat

<400> SEQUENCE: 17 aatgtagc                                                                      8

<210> SEQ ID NO 18
<211> LENGTH: 11
<212> TYPE: DNA
<213> ORGANISM: Artificial sequence
<220> FEATURE:
<223> OTHER INFORMATION: upper strand primer for the human Alu repeat

<400> SEQUENCE: 18
tcctgagctc a                                                                 11

<210> SEQ ID NO 19
<211> LENGTH: 8
<212> TYPE: DNA
<213> ORGANISM: Artificial sequence
<220> FEATURE:
<223> OTHER INFORMATION: lower strand primer for the human Alu repeat

<400> SEQUENCE: 19 gtaatccc                                                                      8

<210> SEQ ID NO 20
<211> LENGTH: 34
<212> TYPE: DNA
<213> ORGANISM: Mus musculus

<400> SEQUENCE: 20
acgtgaattc tggcgaggaa aactgaaaaa ggtg                                         34

<210> SEQ ID NO 21
<211> LENGTH: 34
<212> TYPE: DNA
<213> ORGANISM: Mus musculus

<400> SEQUENCE: 21
gccagaattc acgtcctaaa gtgtgtattt ctca                                         34

<210> SEQ ID NO 22
<211> LENGTH: 39
<212> TYPE: DNA
<213> ORGANISM: Mus musculus

<400> SEQUENCE: 22
gagtgaattc cactgaaaaa cacattcgtt ggaaacggg                                    39

<210> SEQ ID NO 23
<211> LENGTH: 40
<212> TYPE: DNA
<213> ORGANISM: Mus musculus

<400> SEQUENCE: 23
ttcagtggaa ttcactcatc taatatgttc tacagtgtgg  40

<210> SEQ ID NO 24
<211> LENGTH: 35
<212> TYPE: DNA
<213> ORGANISM: Artificial sequence
<220> FEATURE:
<223> OTHER INFORMATION: forward primer for the Alu repeats

<400> SEQUENCE: 24
ttaaatgaat tctgagcatg gtggctcaca cctgt  35

<210> SEQ ID NO 25
<211> LENGTH: 35
<212> TYPE: DNA
<213> ORGANISM: Artificial sequence
<220> FEATURE:
<223> OTHER INFORMATION: reverse primer for the Alu repeats

<400> SEQUENCE: 25
atttcagaat tcgaagccaa ggcagttgga ttgtt  35

<210> SEQ ID NO 26
<211> LENGTH: 22
<212> TYPE: DNA
<213> ORGANISM: Artificial sequence
<220> FEATURE:
<223> OTHER INFORMATION: forward primer for the Gamma 8 repeats

<400> SEQUENCE: 26
cgatgaaggc ctctccgatc ct  22

<210> SEQ ID NO 27
<211> LENGTH: 22
<212> TYPE: DNA
<213> ORGANISM: Artificial sequence
<220> FEATURE:
<223> OTHER INFORMATION: reverse primer for the Gamma 8 repeats

<400> SEQUENCE: 27
gaaagtcctg ggggcttctg ga  22

<210> SEQ ID NO 28
<211> LENGTH: 131
<212> TYPE: DNA
<213> ORGANISM: Mus musculus

<400> SEQUENCE: 28
gatccggacc gatggcgagg aaaactgaaa aaggtggaaa atttagaaat gtccactgta  60
ggacgtggaa tatggcaaga aaactgaaaa tcatggaaaa tgagaaacat ccacttgacg  120
aacgcgtgat c  131

<210> SEQ ID NO 29
<211> LENGTH: 138
<212> TYPE: DNA
<213> ORGANISM: Mus musculus

<400> SEQUENCE: 29
gatcacgcgt tgaaaaatga cgaaatcact aaaaacgtga aaatgagaa atgcacactg  60
aaggacctgg aatatggcga gaaaactgaa aatcacggaa aatgagaaat acacacttta  120
ggacgtgcgg accggatc  138

<210> SEQ ID NO 30
<211> LENGTH: 83
<212> TYPE: DNA
<213> ORGANISM: Mus musculus

<400> SEQUENCE: 30
gatccggacc gacagtgtat atcaatgagt tacaatgaga acatggaaa atgataaaaa    60 ccacactgta gaaacgcgtg atc                                          83

<210> SEQ ID NO 31
<211> LENGTH: 81
<212> TYPE: DNA
<213> ORGANISM: Mus musculus

<400> SEQUENCE: 31
gatcacgcgt aacatattag atgagtgagt tacactgaaa acacattcg ttggaaacgg   60 gatttgtaga cggaccggat c                                            81

<210> SEQ ID NO 32
<211> LENGTH: 189
<212> TYPE: DNA
<213> ORGANISM: Artificial sequence
<220> FEATURE:
<223> OTHER INFORMATION: representative targeting hook for the Alu
      repeats 5'

<400> SEQUENCE: 32
gatccggacc gtcaagacca gcctaggcaa tgtagcgaga cgccatctca aaatattaaa   60 ataagtaaa taagtaaata aaagaaggt taagtataca aatgtatttc ctttgttgtg   120
aatttatttc aatttatag tgatttttt ttttgagac gaagtctcac tcttgtccca   180
cgcgtgatc                                                         189

<210> SEQ ID NO 33
<211> LENGTH: 129
<212> TYPE: DNA
<213> ORGANISM: Artificial sequence
<220> FEATURE:
<223> OTHER INFORMATION: representative targeting hook for the Alu
      repeats 3'

<400> SEQUENCE: 33
gatcacgcgt atcttggttc actgcaacct ctgcgtgggc tcaagcaatc ctcccacctc   60
cctttccaga gtagcgggga ccacaggtgt gtgccaccac acctgactaa tttttgcacg  120
gaccggatc                                                         129

<210> SEQ ID NO 34
<211> LENGTH: 163
<212> TYPE: DNA
<213> ORGANISM: Artificial sequence
<220> FEATURE:
<223> OTHER INFORMATION: representative targeting hook for the Gamma 8
      repeats 5'
<220> FEATURE:
<221> NAME/KEY: misc_feature
<222> LOCATION: (116)..(116)
<223> OTHER INFORMATION: n is a, c, g, or t

<400> SEQUENCE: 34
gatccggacc gactatggtg gacattgtgg tcaggcagag gtgagaagac agtgagaccg   60
cagggaatgc tgggagcctc ctagggatgt ctctcccacc ccagaagctt accatngttg  120

```
tttcggatgg gctgtaatac cccatgcttt ggtacgcgtg atc                    163
```

<210> SEQ ID NO 35
<211> LENGTH: 128
<212> TYPE: DNA
<213> ORGANISM: Artificial sequence
<220> FEATURE:
<223> OTHER INFORMATION: representative targeting hook for the Gamma 8
      repeats 3'

<400> SEQUENCE: 35

```
gatcacgcgt gtagagggaa gaattggcaa gactgcaggg taatgctgcg accctcccaa    60
ggagagcctc tcccatccta gaagcccccc aggtctgtca cggataggct gtagtgtcgg   120
accggatc                                                            128
```

<210> SEQ ID NO 36
<211> LENGTH: 59
<212> TYPE: DNA
<213> ORGANISM: Homo sapiens

<400> SEQUENCE: 36

```
atgcatcgat aagagtgttt caaaactgct ctatcaaaag gaatgttcaa cgcgtgatc     59
```

<210> SEQ ID NO 37
<211> LENGTH: 63
<212> TYPE: DNA
<213> ORGANISM: Homo sapiens

<400> SEQUENCE: 37

```
gatcacgcgt gagttgaatg caaacttcac aaagaagttt ctgagaatgc tcgaggcatg    60
cat                                                                  63
```

<210> SEQ ID NO 38
<211> LENGTH: 17
<212> TYPE: DNA
<213> ORGANISM: Artificial sequence
<220> FEATURE:
<223> OTHER INFORMATION: CENP-B consensus sequence
<220> FEATURE:
<221> NAME/KEY: misc_feature
<222> LOCATION: (1)..(1)
<223> OTHER INFORMATION: N = A, T, C, or G
<220> FEATURE:
<221> NAME/KEY: misc_feature
<222> LOCATION: (6)..(9)
<223> OTHER INFORMATION: N = A, T, C, or G, independently
<220> FEATURE:
<221> NAME/KEY: misc_feature
<222> LOCATION: (11)..(12)
<223> OTHER INFORMATION: N = A, T, C, or G, independently
<220> FEATURE:
<221> NAME/KEY: misc_feature
<222> LOCATION: (17)..(17)
<223> OTHER INFORMATION: N = A, T, C, or G

<400> SEQUENCE: 38

```
nttcgnnnna nncgggn                                                   17
```

<210> SEQ ID NO 39
<211> LENGTH: 1868
<212> TYPE: DNA
<213> ORGANISM: Artificial sequence
<220> FEATURE:
<223> OTHER INFORMATION: p11-4 alphoid DNA probe

<400> SEQUENCE: 39

-continued

| | |
|---|---|
| aattcaaata aaaggtagac agcagcattc tcagaaattt ctttctgatg tctgcattca | 60 |
| actcatagag ttgaagattg cctttcatag agcaggtttg aaacactctt tctggagtat | 120 |
| ctggatgtgg acatttggag cgctttgatg cctacggtgg aaaagtaaat atcttccata | 180 |
| aaaacgagac agaaggattc tcagaaacaa gtttgtgatg tgtgtactca gctaacagag | 240 |
| tggaaccttt cttttacag agcagctttg aaactctatt tttgtggatt ctgcaaattg | 300 |
| atatttagat tgctttaacg atatcgttgg aaaagggaat atcgtcatac aaaatctaga | 360 |
| cagaagcatt ctcacaaact tctttgtgat gtgtgtcctc aactaacaga gttgaacctt | 420 |
| tcttttgatg cagcagtttg gaaacactct ttttgtagaa actgtaagtg gatatttgga | 480 |
| tagctctaac gatttcgttg gaaacgggaa tatcatcatc taaaatctag acagaagcac | 540 |
| tattagaaac tacttggtga tatctgcatt caagtcacag agttgaacat tcccttactt | 600 |
| tgagcacgtt tgaaacactc ttttggaaga atctggaagt ggacatttgg agcgctttga | 660 |
| ctgcctttgt tgaaaaggaa acgtcttcca ataaaagcca gacagaagca ttctcagaaa | 720 |
| cttgttcgtg atgtgtgtac tcaactaaaa gagttgaacc tttctattga tagagcagtt | 780 |
| ttgaaacact cttttgtgg attctgcaag tggatatttg gattgctttg aggatttcgt | 840 |
| tggaagcggg aattcgtata aaaactagac agcagcattc ccagaaattt ctttcggata | 900 |
| tttccattca actcatagag atgaacatgg cctttcatag agcaggtttg aaacactctt | 960 |
| tttgtagttt gtggaagtgg acatttcgat cgccttgacg cctacggtga aaaaggaaat | 1020 |
| atcttcccat aaaaatagac agaagcattc tcagaaactt gttggtgata tgtgtctcaa | 1080 |
| ctaacagagt tgaactttgc cattgataga gagcagtttt gaaacactct ttttgtggaa | 1140 |
| tctgcaagtg gatatttgga tagcttggag gatttcgttg gaagcgggaa ttcaaataaa | 1200 |
| aggtagacag cagcattctc agaaatttct ttctgatgac tgcattcaac tcatagagtt | 1260 |
| gaacattccc tttcatagag caggtttgaa acactctttc tggagtatct ggatgtggac | 1320 |
| atttggagcg ctttgatgcc tatggtgaaa agtaaatat cttcccataa aaacgagaca | 1380 |
| gaaggattct gagaaacaag tttgtgatgt gtgtactcag ctaacagagt ggaacctctc | 1440 |
| ttttgatgca gcagtttgga aacactcttt tgtagaaac tgtaagtgga tatttggata | 1500 |
| gctctaatga tttcgttgga aacgggaata tcatcatcta aaatctagac agaagccctc | 1560 |
| tcagaaacta ctttgtgata tctgcattca agtcacagag ttgaacattc gctttcttag | 1620 |
| agcacgttgg aaacactctt tttgtagtgt ctggaagtgg acatttggag cgctttgatg | 1680 |
| cctttggtga aaagggaat gtcttcccat aaaaactaga cagaagcatt ctcagaaact | 1740 |
| tgtttttgat gtgtgtaccc agccaaagga gttgaacatt tctattgata gagcagtttt | 1800 |
| gaaacactct ttttgtggaa aatgcaggtg gatatttgga tagcttggag gatttcgttg | 1860 |
| gaagcggg | 1868 |

<210> SEQ ID NO 40
<211> LENGTH: 6941
<212> TYPE: DNA
<213> ORGANISM: Artificial sequence
<220> FEATURE:
<223> OTHER INFORMATION: Vector sequence
<220> FEATURE:
<221> NAME/KEY: misc_feature
<222> LOCATION: (1813)..(6473)
<223> OTHER INFORMATION: Vector probe sequence

<400> SEQUENCE: 40
gcggccgcta atacgactca ctatagggag aagcttggat cctatagtgt cacctaaatc    60

```
gtatgcggcc gcccgggccg tcgaccaatt ctcatgtttg acagcttatc atcgaatttc    120
tgccattcat ccgcttatta tcacttattc aggcgtagca accaggcgtt taagggcacc    180
aataactgcc ttaaaaaaat tacgccccgc cctgccactc atcgcagtac tgttgtaatt    240
cattaagcat tctgccgaca tggaagccat cacaaacggc atgatgaacc tgaatcgcca    300
gcggcatcag caccttgtcg ccttgcgtat aatatttgcc catggtgaaa acggggcga    360 agaagttgtc catattggcc acgtttaaat caaaactggt gaaactcacc cagggattgg    420
ctgagacgaa aaacatattc tcaataaacc ctttagggaa ataggccagg ttttcaccgt    480
aacacgccca atcttgcgaa tatatgtgta gaaactgccg gaaatcgtcg tggtattcac    540
tccagagcga tgaaaacgtt tcagtttgct catggaaaac ggtgtaacaa gggtgaacac    600
tatcccatat caccagctca ccgtctttca ttgccatacg gaattccgga tgagcattca    660
tcaggcgggc aagaatgtga ataaaggccg gataaaactt gtgcttattt ttctttacgg    720 tcttaaaaa ggccgtaata tccagctgaa cggtctggtt ataggtacat tgagcaactg    780
actgaaatgc ctcaaaatgt tctttacgat gccattggga tatatcaacg gtggtatatc    840
cagtgatttt tttctccatt ttagcttcct tagctcctga aaatctcgat aactcaaaaa    900
atacgcccgg tagtgatctt atttcattat ggtgaaagtt ggaacctctt acgtgccgat    960
caacgtctca ttttcgccaa aagttggccc agggcttccc ggtatcaaca gggacaccag   1020
gatttattta ttctgcgaag tgatcttccg tcacaggtat ttattcgcga taagctcatg   1080
gagcggcgta accgtcgcac aggaaggaca gagaaagcgc ggatctggga agtgacggac   1140
agaacggtca ggacctggat tggggaggcg gttgccgccg ctgctgctga cggtgtgacg   1200
ttctctgttc cggtcacacc acatacgttc cgccattcct atgcgatgca catgctgtat   1260
gccggtatac cgctgaaagt tctgcaaagc ctgatggac ataagtccat cagttcaacg   1320
gaagtctaca cgaaggtttt tgcgctggat gtggctgccc ggcaccgggt gcagtttgcg   1380
atgccggagt ctgatgcggt tgcgatgctg aaacaattat cctgagaata aatgccttgg   1440
cctttatatg gaaatgtgga actgagtgga tatgctgttt ttgtctgtta aacagagaag   1500
ctggctgtta tccactgaga gcgaacgaaa acagtcggga aaatctccca ttatcgtaga   1560
gatccgcatt attaatctca ggagcctgtg tagcgtttat aggaagtagt gttctgtcat   1620
gatgcctgca agcggtaacg aaaacgattt gaatatgcct tcaggaacaa tagaaatctt   1680
cgtgcggtgt tacgttgaag tggagcggat tatgtcagca atggacagaa caacctaatg   1740
aacacagaac catgatgtgg tctgtccttt tacagccagt agtgctcgcc gcagtcgagc   1800
gacagggcga agccctcgag tgagcgagga agcaccaggg aacagcactt atatattctg   1860
cttacacacg atgcctgaaa aaacttccct tggggttatc cacttatcca cggggatatt   1920
tttataatta tttttttat agttttaga tcttcttttt tagagcgcct tgtaggcctt   1980
tatccatgct ggttctagag aaggtgttgt gacaaattgc cctttcagtg tgacaaatca   2040
ccctcaaatg acagtcctgt ctgtgacaaa ttgcccttaa ccctgtgaca aattgccctc   2100
agaagaagct gttttttcac aaagttatcc ctgcttattg actctttttt atttagtgtg   2160
acaatctaaa aacttgtcac acttcacatg gatctgtcat ggcggaaaca gcggttatca   2220
atcacaagaa acgtaaaaat agcccgcgaa tcgtccagtc aaacgacctc actgaggcgg   2280
catatagtct ctcccgggat caaaaacgta tgctgtatct gttcgttgac cagatcagaa   2340
aatctgatgg caccctacag gaacatgacg gtatctgcga gatccatgtt gctaaatatg   2400
```

```
ctgaaatatt cggattgacc tctgcggaag ccagtaagga tatacggcag gcattgaaga    2460
gtttcgcggg gaaggaagtg gttttttatc gccctgaaga ggatgccggc gatgaaaaag    2520
gctatgaatc ttttccttgg tttatcaaac gtgcgcacag tccatccaga gggctttaca    2580
gtgtacatat caacccatat ctcattccct tctttatcgg gttacagaac cggtttacgc    2640
agtttcggct tagtgaaaca aaagaaatca ccaatccgta tgccatgcgt ttatacgaat    2700
ccctgtgtca gtatcgtaag ccggatggct caggcatcgt ctctctgaaa atcgactgga    2760
tcatagagcg ttaccagctg cctcaaagtt accagcgtat gcctgacttc cgccgccgct    2820
tcctgcaggt ctgtgttaat gagatcaaca gcagaactcc aatgcgcctc tcatacattg    2880
agaaaaagaa aggccgccag acgactcata tcgtattttc cttccgcgat atcacttcca    2940
tgacgacagg atagtctgag ggttatctgt cacagatttg agggtggttc gtcacatttg    3000
ttctgaccta ctgagggtaa tttgtcacag ttttgctgtt tccttcagcc tgcatggatt    3060
ttctcatact ttttgaactg taattttttaa ggaagccaaa tttgagggca gtttgtcaca    3120
gttgatttcc ttctctttcc cttcgtcatg tgacctgata tcgggggtta gttcgtcatc    3180
attgatgagg gttgattatc acagtttatt actctgaatt ggctatccgc gtgtgtacct    3240
ctacctggag tttttcccac ggtggatatt tcttcttgcg ctgagcgtaa gagctatctg    3300
acagaacagt tcttctttgc ttcctcgcca gttcgctcgc tatgctcggt tacacggctg    3360
cggcgagcgc tagtgataat aagtgactga ggtatgtgct cttcttatct ccttttgtag    3420
tgttgctctt atttttaaaca actttgcggt ttttttgatga cttgtgcgatt ttgttgttgc    3480 tttgcagtaa attgcaagat ttaataaaaa aacgcaaagc aatgattaaa ggatgttcag    3540
aatgaaactc atggaaacac ttaaccagtg cataaacgct ggtcatgaaa tgacgaaggc    3600
tatcgccatt gcacagttta atgatgacag cccggaagcg aggaaaataa cccggcgctg    3660
gagaataggt gaagcagcgg atttagttgg ggtttcttct caggctatca gagatgccga    3720
gaaagcaggg cgactaccgc acccggatat ggaaattcga ggacgggttg agcaacgtgt    3780
tggttataca attgaacaaa ttaatcatat gcgtgatgtg tttggtacgc gattgcgacg    3840
tgctgaagac gtatttccac cggtgatcgg ggttgctgcc cataaaggtg gcgtttacaa    3900
aacctcagtt tctgttcatc ttgctcagga tctggctctg aaggggctac gtgttttgct    3960 cgtgaaggt aacgacccccc agggaacagc ctcaatgtat cacgatgggg taccagatct    4020
tcatattcat gcagaagaca ctctcctgcc tttctatctt ggggaaaagg acgatgtcac    4080
ttatgcaata aagcccactt gctggccggg gcttgacatt attccttcct gtctggctct    4140
gcaccgtatt gaaactgagt taatgggcaa atttgatgaa ggtaaactgc ccaccgatcc    4200
acacctgatg ctccgactgg ccattgaaac tgttgctcat gactatgatg tcatagttat    4260
tgacagcgcg cctaacctgg gtatcggcac gattaatgtc gtatgtgctg ctgatgtgct    4320
gattgttccc acgcctgctg agttgtttga ctacacctcc gcactgcagt ttttcgatat    4380
gcttcgtgat ctgctcaaga acgttgatct taaagggttc gagcctgatg tacgtatttt    4440
gcttaccaaa tacagcaata gtaatggctc tcagtccccg tggatggagg agcaaattcg    4500
ggatgcctgg ggaagcatgg ttctaaaaaa tgttgtacgt gaaacggatg aagttggtaa    4560
aggtcagatc cggatgagaa ctgttttttga acaggccatt gatcaacgct cttcaactgg    4620
tgcctggaga aatgctcttt ctatttggga acctgtctgc aatgaaattt tcgatcgtct    4680
gattaaacca cgctgggaga ttagataatg aagcgtgcgc ctgttattcc aaaacatacg    4740
ctcaatactc aaccggttga agatacttcg ttatcgacac cagctgcccc gatggtggat    4800
```

```
tcgttaattg cgcgcgtagg agtaatggct cgcggtaatg ccattacttt gcctgtatgt    4860
ggtcgggatg tgaagtttac tcttgaagtg ctccggggtg atagtgttga agagacctct    4920
cgggtatggt caggtaatga acgtgaccag gagctgctta ctgaggacgc actggatgat    4980
ctcatcccct cttttctact gactggtcaa cagacaccgg cgttcggtcg aagagtatct    5040
ggtgtcatag aaattgccga tgggagtcgc cgtcgtaaag ctgctgcact taccgaaagt    5100
gattatcgtg ttctggttgg cgagctggat gatgagcaga tggctgcatt atccagattg    5160
ggtaacgatt atcgcccaac aagtgcttat gaacgtggtc agcgttatgc aagccgattg    5220
cagaatgaat ttgctggaaa tatttctgcg ctggctgatg cggaaaatat ttcacgtaag    5280
attattaccc gctgtatcaa caccgccaaa ttgcctaaat cagttgttgc tcttttttct    5340
cacccgggtg aactatctgc ccggtcaggt gatgcacttc aaaaagcctt tacagataaa    5400
gaggaattac ttaagcagca ggcatctaac cttcatgagc agaaaaaagc tggggtgata    5460
tttgaagctg aagaagttat cactctttta acttctgtgc ttaaaacgtc atctgcatca    5520
agaactagtt taagctcacg acatcagttt gctcctggag cgacagtatt gtataagggc    5580
gataaaatgg tgcttaacct ggacaggtct cgtgttccaa ctgagtgtat agagaaaatt    5640
gaggccattc ttaaggaact tgaaaagcca gcaccctgat gcgaccacgt tttagtctac    5700
gtttatctgt ctttacttaa tgtcctttgt tacaggccag aaagcataac tggcctgaat    5760
attctctctg ggcccactgt tccacttgta tcgtcggtct gataatcaga ctgggaccac    5820
ggtcccactc gtatcgtcgg tctgattatt agtctgggac cacggtccca ctcgtatcgt    5880
cggtctgatt attagtctgg gaccacggtc ccactcgtat cgtcggtctg ataatcagac    5940
tgggaccacg gtcccactcg tatcgtcggt ctgattatta gtctgggacc atggtcccac    6000
tcgtatcgtc ggtctgatta ttagtctggg accacggtcc cactcgtatc gtcggtctga    6060
ttattagtct ggaaccacgg tcccactcgt atcgtcggtc tgattattag tctgggacca    6120
cggtcccact cgtatcgtcg gtctgattat tagtctggga ccacgatccc actcgtgttg    6180
tcggtctgat tatcggtctg ggaccacggt cccacttgta ttgtcgatca gactatcagc    6240
gtgagactac gattccatca atgcctgtca agggcaagta ttgacatgtc gtcgtaacct    6300
gtagaacgga gtaacctcgg tgtgcggttg tatgcctgct gtggattgct gctgtgtcct    6360
gcttatccac aacattttgc gcacggttat gtggacaaaa tacctggtta cccaggccgt    6420
gccggcacgt taaccgggct gcatccgatg caagtgtgtc gctgtcgacg agctcgcgag    6480
ctcggacatg aggttgcccc gtattcagtg tcgctgattt gtattgtctg aagttgtttt    6540
tacgttaagt tgatgcagat caattaatac gatacctgcg tcataattga ttatttgacg    6600
tggtttgatg gcctccacgc acgttgtgat atgtagatga taatcattat cactttacgg    6660
gtcctttccg gtgatccgac aggttacggg gcggcgacct cgcgggtttt cgctatttat    6720
gaaaattttc cggtttaagg cgtttccgtt cttcttcgtc ataacttaat gttttttattt    6780 aaaatacccct ctgaaaagaa aggaaacgac aggtgctgaa agcgagcttt ttggcctctg    6840
tcgtttcctt tctctgttttt tgtccgtgga atgaacaatg gaagtccgag ctcatcgcta    6900
ataacttcgt atagcataca ttatacgaag ttatattcga t                        6941
```

<210> SEQ ID NO 41
<211> LENGTH: 28
<212> TYPE: DNA
<213> ORGANISM: Artificial sequence
<220> FEATURE:

<223> OTHER INFORMATION: BACX primer

<400> SEQUENCE: 41
ccctcgagtg agcgaggaag caccaggg                                28

<210> SEQ ID NO 42
<211> LENGTH: 29
<212> TYPE: DNA
<213> ORGANISM: Artificial sequence
<220> FEATURE:
<223> OTHER INFORMATION: BACS primer

<400> SEQUENCE: 42
gctcgtcgac agcgacacac ttgcatcgg                               29

<210> SEQ ID NO 43
<211> LENGTH: 18
<212> TYPE: DNA
<213> ORGANISM: Artificial sequence
<220> FEATURE:
<223> OTHER INFORMATION: primer alpha(1)18a

<400> SEQUENCE: 43
acagaagcat tctcagaa                                           18

<210> SEQ ID NO 44
<211> LENGTH: 18
<212> TYPE: DNA
<213> ORGANISM: Artificial sequence
<220> FEATURE:
<223> OTHER INFORMATION: primer alpha(1)18b

<400> SEQUENCE: 44
ttctgagaat gcttctgt                                           18

<210> SEQ ID NO 45
<211> LENGTH: 18
<212> TYPE: DNA
<213> ORGANISM: Artificial sequence
<220> FEATURE:
<223> OTHER INFORMATION: primer alpha(Y)a

<400> SEQUENCE: 45
agaaacttct ttgtgatg                                           18

<210> SEQ ID NO 46
<211> LENGTH: 18
<212> TYPE: DNA
<213> ORGANISM: Artificial sequence
<220> FEATURE:
<223> OTHER INFORMATION: primer alpha(Y)b

<400> SEQUENCE: 46
catcacaaag aagtttct                                           18

<210> SEQ ID NO 47
<211> LENGTH: 15
<212> TYPE: DNA
<213> ORGANISM: Artificial sequence
<220> FEATURE:
<223> OTHER INFORMATION: primer CB15a

<400> SEQUENCE: 47
tcgttggaaa cggga                                              15

```
<210> SEQ ID NO 48
<211> LENGTH: 15
<212> TYPE: DNA
<213> ORGANISM: Artificial sequence
<220> FEATURE:
<223> OTHER INFORMATION: primer CB15b

<400> SEQUENCE: 48
tcccgtttcc aacga                                                        15

<210> SEQ ID NO 49
<211> LENGTH: 168
<212> TYPE: DNA
<213> ORGANISM: Homo sapiens

<400> SEQUENCE: 49
cattcacaga aaactcttgg tgacgactga gtttaactca cagagctgaa cattcctttg        60
gatggagcag tttcgaaaca cactatttgt agaatgtgca agtggatatt taggcctctc       120
tgaggatttc gttggaaacg ggataaaccg cacagaacta aacagaag                    168

<210> SEQ ID NO 50
<211> LENGTH: 171
<212> TYPE: DNA
<213> ORGANISM: Artificial sequence
<220> FEATURE:
<223> OTHER INFORMATION: One monomer of the tetO dimer alphoid,
      containing a tetO motif

<400> SEQUENCE: 50
cattctgaga aacttctttg tgatgtttgc attcaactca cagagttgaa cattcctttt        60
cattgagcag tttggaaaca ctcttttttgt agaatcctgc aagtgggagt ttaccactcc     120
ctatcagtga tagagaaagt gaaagtcctt cacataaaaa ctagacagaa g                171

<210> SEQ ID NO 51
<211> LENGTH: 171
<212> TYPE: DNA
<213> ORGANISM: Artificial sequence
<220> FEATURE:
<223> OTHER INFORMATION: Consensus alphoid monomer

<400> SEQUENCE: 51
cattctcaga aacttctttg tgatgtgtgc attcaactca cagagttgaa ccttcctttt        60
catagagcag ttttgaaaca ctcttttttgt agaatctgca agtggatatt tggaccgctt     120
tgaggccttc gttggaaacg ggaatatctt catataaaaa ctagacagaa g                171
```

RAPID GENERATION OF LONG SYNTHETIC CENTROMERIC TANDEM REPEATS FOR MAMMALIAN ARTIFICIAL CHROMOSOME FORMATION

CROSS REFERENCE TO RELATED APPLICATIONS

This is the U.S. National Stage of International Application No. PCT/US 2006/013362, filed Apr. 8, 2006, which was published in English under PCT Article 21(2), which in turn claims the benefit of U.S. Provisional Patent Application 60/669,589, filed Apr. 8, 2005. Both applications are incorporated by reference herein in their entirety.

FIELD

This disclosure relates to methods of forming and using mammalian artificial chromosomes (MACs), such as human artificial chromosomes (HACs), which include a long synthetic centromeric tandem repeat. Long synthetic tandem repeats are concatenated and captured using in vivo homologous recombination. In particular embodiments, the long synthetic centromeric tandem repeat is generated using a combination of rolling circle amplification (RCA), and in vivo homologous recombination (such as transformation-associated recombination, TAR). In other embodiments, relatively short repeat sequences are assembled (multimerized) using directional in vitro ligation and one or more such multimers are captured (concatamerized) using in vivo homologous recombination (such as TAR) to form an engineered centromeric region useful in forming a MAC.

BACKGROUND OF THE DISCLOSURE

Tandem repeat arrays are present throughout the genomes of eukaryotes and play important roles in creating and maintaining of specialized chromatin, e.g., at centromeres and telomeres, and are often associated with heterochromatin (Lee et al., *Hum. Genet.* 100:291-304, 1997; de Lange, *Nat. Rev. Mol. Cell. Biol.* 5:323-329, 2004). Small tandem repeat arrays also play a role in gene regulation (Lippman et al., *Nature* 430:471-476, 2004; Jasinska & Krzyzosiak, *FEBS Lett.* 567:136-141, 2004; Li et al., *Mol. Biol. Evol.* 21:991-1007, 2004), and variants have been linked to human disease or disease likelihood (Riley & Krieger, *Gene* 344:203-211, 2005; Mandola et al., *Cancer Res.* 63:2898-2904, 2003; Watanabe et al., *Am. J. Pathol.* 163:633-641, 2003; Everett & Wood, *Brain* 127:2385-2405, 2004). They also may play a role in rapid evolution (Fondon & Garner, *Proc. Natl. Acad. Sci. USA.* 101:18058-18063, 2004; Sinha & Siggia, *Mol. Biol. Evol.* [Epub], Jan. 19, 2005).

Centromeric tandem repeats are associated with the functional kinetochore, the structure that attaches to spindle microtubules for chromosome partitioning to daughter cells. The centromeres of most of the higher eukaryotes that have been studied so far contain tandem repeat arrays of hundreds to thousands of kilobases in size, including centromeres of plants, invertebrates, and vertebrates (Guenatri et al., *J. Cell Biol.* 166:493-505, 2004; Jiang et al., *Trends Plant. Sci.* 8:570-575, 2003; Sun et al., *Genome Res.* 13:182-194, 2003).

Alphoid (alpha-satellite) arrays at human centromeres can extend over many millions of base pairs. Type I arrays are composed of highly homogeneous higher-order repeats (HOR) of 170 bp monomer that are unique to a specific chromosome or shared by a few chromosomes (Lee et al., *Hum. Genet.* 100:291-304, 1997). Type I arrays are believed to be an important DNA component of a functional centromere. These arrays associate with centromere proteins (such as CENP-A), which closely interact with DNA to form the kinetochore (Ando et al., *Mol. Cell. Biol.* 22, 2229-2241, 2002; Spence et al., *EMBO J.* 21:5269-5280, 2002). Moreover, type I arrays are competent to form Human Artificial Chromosomes (HACs) when transformed into human cells (Harrington et al., *Nat. Genet.* 15:345-355, 1997; Ikeno et al., *Nat. Biotechnol.* 16:431-439, 1998; Ebersole et al., *Hum. Mol. Genet.* 9:1623-1631, 2000; Larin & Mejia, *Trends Genet.* 18:313-319, 2002; Laner et al., *Cytogenet. Genome Res.* 107:9-13, 2004; Ohzeki et al., *J. Cell Biol.* 159, 765-775, 2002; Kouprina et al., *Nucleic Acids Res.* 31:922-934, 2003; Basu et al., *Nucleic Acids Res.* 33:587-596, 2005; Schueler et al., *Science* 294:109-115, 2001).

HACs represent extra chromosomes carrying all the required components of a functional kinetochore. HACs have various advantages as gene expression vectors with potential for use in gene therapy. They are stably maintained at a low copy in the host nucleus. They also contain no viral genes or proteins and therefore they should not cause severe immunogenic responses that have been found to be a serious problem with adenoviral vectors. HACs are particularly well suited for carrying intact mammalian genes surrounded by all their long range controlling elements that should confer physiological levels of fully regulated gene expression. Several groups have had success in complementing a genetic deficiency with HACs carrying the full-size gene (e.g., see discussion in Larin & Mejia, *Trends Genet.* 18:313-319, 2002).

Early HAC formation studies used only a few of the many subfamilies of alphoid DNA arrays that were identified in BAC and YAC libraries. Alphoid arrays with monomers containing the 17 bp CENP-B box from chromosomes 21, X, 17 and 5 cloned into YAC, BAC or PAC vectors have been shown to be competent to form de novo artificial chromosomes in cultured cells, whereas arrays lacking the CENP-B box from the Y chromosome, chromosome 21 type II, and chromosome 22 have proved to be inefficient (Harrington et al., *Nat. Genet.* 15:345-355, 1997; Ikeno et al., *Nat. Biotechnol.* 16:431-439, 1998; Ebersole et al., *Hum. Mol. Genet.* 9:1623-1631, 2000; Larin & Mejia, *Trends Genet.* 18:313-319, 2002; Laner et al., *Cytogenet. Genome Res.* 107:9-13, 2004; Ohzeki et al., *J. Cell Biol.* 159, 765-775, 2002; Kouprina et al., *Nucleic Acids Res.* 31:922-934, 2003; Basu et al., *Nucleic Acids Res.* 33:587-596, 2005). Recently, the requirement of the CENP-B box for de novo centromere and HAC assembly was demonstrated using synthetic type I alphoid DNAs containing functional CENP-B boxes or mutant CENP-B boxes, (Ohzeki et al., *J. Cell Biol.* 159, 765-775, 2002; Basu et al., *Nucleic Acids Res.* 33:587-596, 2005).

However the presence of the CENP-B box is not sufficient to predict an effective array. X chromosome arrays that contain CENP-B boxes are relatively poor substrates when compared to chromosome 17-derived arrays (Schueler et al., *Science* 294:109-115, 2001). Substitution of alphoid sequence outside the CENP-B box for GC rich DNA in a synthetically constructed array demonstrated that the CENP-B box alone is not sufficient for centromere nucleation (Ohzeki et al., *J. Cell Biol.* 159, 765-775, 2002). Although core residues within the 170-base CENP-B box have been identified which are required for efficient CENP-B binding (Muro et al., *J. Cell Biol.* 116:585-596, 1992; Masumoto et al., *J. Cell. Biol.* 109: 1963-1973, 1989; Masumoto et al., In *Chromosome and Aneuploidy* (Vig, B K, ed.), pp. 31-43, Springer-Verlag, Berlin, 1993), which bases of the alphoid monomer apart from the CENP-B box are essential for successful centromere nucleation remains unknown. AT richness is found in the centromere repeats of many organisms including human alphoid repeats, but it has yet to be determined if this is a meaningful feature or if specific bases are critical.

Large alphoid tandem repeat DNA segments isolated from genomic libraries are difficult to fully characterize and cannot be modified readily. Therefore, further analysis of alphoid DNA arrays with a defined sequence is required to elucidate the structural requirements for efficient de novo assembly of centromere structure.

SUMMARY OF THE DISCLOSURE

To address deficiencies in the technology previously available, methods to rapidly construct synthetic DNA arrays, including particularly synthetic alphoid DNA arrays, with a predetermined structure have been developed and are described herein. Specific examples of these techniques involve two steps: (1) assembly of multiple copies of a starting repeat sequence, for instance using in vitro ligation or rolling circle amplification of a relatively short alphoid or other DNA multimer, for example a dimer, trimer, quadramer, pentamer, etc., and (2) assembly of the amplified (or assembled/concatamerized), repetitive fragments by in vivo homologous recombination (such as transformation-associated recombination) in yeast or another host cell capable of recombination. Using the described method, a set of different representative synthetic alphoid DNA arrays varying in size from 30 to 120 kb was constructed and demonstrated to be competent in HAC (that is, human artificial chromosome) formation.

Because any nucleotide can be easily changed in a starting repeat (e.g., an alphoid) sequence before its amplification, the artificial chromosome construction methods described herein are useful for identifying and/or altering functional regions of the repeat, for instance for de novo centromere/kinetochore seeding and the construction of regulatable centromeres and chromosomes. Practicable manipulation of alphoid or other types of repeats can also be a basis for elucidating substructure(s) that lead to heterochromatin formation.

With the provision herein of methods for producing de novo long tandem synthetic repeats useful in artificial chromosomes, such as mammalian artificial chromosomes (MACs) and more particularly HACs, there are now enabled various methods of using them. Thus, MACs made using these methods can be used for expression of mammalian and other sequences, particularly in native or near-native sequence context; characterization of native and engineered repeat structure and function; gene therapy, including for instance replacement therapy; and so forth.

There are many other varieties of tandem repeats populating the genomes of eukaryotes, some of which are known to play important roles in cell function by forming or maintaining specialized chromatin required for chromosome segregation, the stabilizing of chromosome ends, or gene regulation, and some of which may be an important substrate for rapid evolution. Because many types of DNA repeats may be similarly amplified, the methods provided herein have more general application to elucidate the role of tandem repeats in the genome and exploit them in various applications. For example, synthetic non-alphoid DNA arrays (such as arrays employing or derived from human gamma-8 satellite, mouse major and minor satellite, or Alu) can be created using methods provided herein. With such arrays, the composition and length of a tandem repeat array can be manipulated, for instance to affect heterochromatin formation by targeting the arrays to a structurally defined ectopic chromosomal site by Cre-lox site-specific recombination. Such manipulation may also be useful to study and alter (e.g., inhibit or regulate) the phenomenon of repeat-induced gene silencing that prevents or reduces transgene expression.

An additional example type of MAC that can be created using this technology is a MAC (or HAC) with a regulated or conditional chromosome. Thus, also provided herein is the first human artificial chromosome (HAC) with a regulated (also described as a "conditional") centromere. A representative regulated chromosome described herein is based around a repetitive DNA array that allows specific targeting of proteins fused to the E. coli tetracycline repressor into the kinetochore of the HAC (or MAC). In certain and selectable cases, this causes the artificial chromosome to lose kinetochore function, and to be rapidly lost from the cells. Such regulatable chromosomes are useful for studies of centromere function, as they can be used to identify proteins the targeting of which will make the HAC more stable, or, conversely, to identify proteins the targeting of which will make the HAC less stable. Selectively targeting different proteins into the HAC to regulate centromere function not only opens the way for functional and structural analysis of the human centromere, but enables a new HAC-based (or MAC-based) gene expression system. Artificial chromosomes with regulated (conditional) centromeres also have application in pharmacology (for instance, in detecting and determining the influence of drugs on aneuploidy) and gene therapy. Variations of this technology are believed to be useful in humans and animal models, as the activity of the centromere can be manipulated by the presence or absence of tetracycline, which prevents tetracycline repressor from binding to the artificial chromosome.

The foregoing and other features and advantages will become more apparent from the following detailed description of several embodiments, which proceeds with reference to the accompanying figures.

BRIEF DESCRIPTION OF THE FIGURES

FIG. 2A: The first step includes amplification of alphoid DNA multimers by rolling circle amplification (RCA) to 1-5 kb. Repeat-specific exonuclease-resistant primers are used for efficient RCA reaction. FIG. 2B: The second step includes co-transformation of the RCA-amplified fragments into yeast cells along with a vector containing alphoid-specific hooks. End to end recombination of alphoid DNA fragments, followed by interaction of the recombined fragments with the vector, results in the rescue of large arrays as circular YACs in yeast. The illustrated vector contains, for instance, a yeast cassette, HIS3/CEN/ARS (a selectable marker HIS3, a centromere sequence CEN6 from yeast chromosome VI, yeast origin of replication ARSH4, correspondingly), a mammalian selectable marker (the Neo or BS gene), and a BAC replicon that allows the YAC clones to be transferred into E. coli or other prokaryote cells.

FIGS. 3A-3D are a series of DNA gels, illustrating generation of large alphoid arrays. FIG. 3A: Multiply-primed RCA reaction products from a 340 bp alphoid dimer (lanes 1 and 2) that retain tandem repeat structure as shown by EcoRI restriction enzyme digestion (lanes 3 and 4). FIG. 3B: The YAC/

BACs generated from the 5-mer alphoid array after recombinational cloning with insert sizes from 30 to 120 kb. FIG. 3C: Array size for alphoid 2-mer, 4-mer, and 5-mer. FIG. 3D: Origin of insert arrays is confirmed by EcoRI digestion. The upper bands represent vector fragments. The 5-mer based array differs from 2-mer and 4-mer based arrays because the 5-mer array was assembled using a TAR-NV vector variant that lacked a BAC cassette. The YAC clone was then converted into YAC/BAC with the BRV1 retrofitting vector (Kouprina et al., Nucleic Acids Res. 31, 922-934, 2003).

FIGS. 4A-4D are a series of gels, illustrating the stability of synthetic 2-mer-, 4-mer, and 5-mer based alphoid arrays. Of 21 independent *E. coli* subclones for each construct, only a few showed a different size (believed to be due to deletions/rearrangements).

FIG. 5A: Both a chromosome 21-specific alphoid ("11mer") and a BAC vector ("BAC") probe detect the HAC (arrows). Additional signal in the alphoid probe and merged panel are detecting the endogenous chromosome 21 centromere in HT1080 cells. FIG. 5B: Validation of the HAC in the clone HT4-10. The pan-alphoid probe ("PAN-") (blocked for chromosome 21 alphoid) does not detect the HAC. FIG. 45C: Detection of HACs with anti-CENP-A, -B, and -E antibodies. A DAPI staining of the DNA is including in each panel.

FIGS. 6A-6C illustrates construction of a tetO dimer alphoid BAC. FIG. 6A: Sequence comparison between the alphoid monomers units used for the tetO dimer alphoid BAC construction and the alphoid consensus. One monomer (SEQ ID NO: 49) of the tetO dimer alphoid is derived from chromosome 17 alphoid type I 16=mer unit and contains a CENP-B box. The other monomer (SEQ ID NO: 50) is a consensus alphoid monomer (SEQ ID NO: 51) in which corresponding sequence of CENP-B box was replaced with 42 bp fragment containing a tetO motif. Individual substituted bases from the consensus are shaded. CENP-B box (position 107 to 148) and tetO motif (position 128 to 144) are shown in shaded blocks at the indicated positions. FIG. 6B: Schematic diagram of the method for construction of tetO dimer alphoid BAC using rolling circle amplification (RCA) and transformation-associated recombination (TAR) cloning in yeast cells. As a results of these processes, a BAC clone was obtained, BAC32-2mer(tetO), containing the 50 kb of tetO dimer alphoid DNA. FIG. 6C: FISH analysis of metaphase cell spreads containing a stable tetO alphoid HAC (AB2-2-18). Signals indicate tetO dimer alphoid probe (top right panel) and BAC vector probe (middle right panel), respectively; overlap is shown in the bottom right panel. Chromosomes were counterstained with DAPI. Chromosome 17 centromeres were also detected with tetO dimer alphoid probe.

(FIG. 8A) Mitotic chromosome spread from the AB 2.2.18 cell line stained with DAPI to show all chromosomes. (FIG. 8B) FISH using a BAC probe on the same spread; the HAC is indicated by an arrow. (FIGS. 8C-8D) FISH on AB 2.2.18 cells in metaphase (FIG. 8C) and anaphase (FIG. 8D). Arrows indicate the HAC undergoing normal segregation. (FIG. 8E) Cell in cytokinesis transfected with RFP-TetRepresser (RFP-TetR) and stained with anti-tubulin antibody (cytoskeleton) and DAPI (DNA). RFP-TetR concentrates to the HAC (arrows), which has segregated to the two daughter cells.

FIGS. 9A-9I are a series of micrographs illustrating that the HAC recruits several centromere/kinetochore proteins throughout the cell cycle. The HAC (arrows) was identified by FISH with a BAC probe, and shown to colocalize with CENP-A (in FIG. 9A), CENP-C (in FIG. 9B) and CENP-H (in FIG. 9C). Insets show the colocalization of the HAC and kinetochore proteins by immunoFISH. The cells shown were in interphase (FIGS. 9A-9C), prophase (FIGS. 9D-9F) and anaphase (FIGS. 9G-9I).

FIGS. 10A-10F are a series of micrographs illustrating that the RFP-TetRepresser localizes to the HAC in vivo. Cells transfected with RFP-TetR (FIG. 10B, FIG. 10E) were fixed with paraformaldehyde and stained for CENP-B (FIG. 10A) or CENP-C (FIG. 10D), and with DAPI for DNA (FIG. 10, FIG. 10F). Both signals colocalize with the HAC (arrows).

FIG. 12A: Experimental protocol for the HAC stability assay. Proteins to be tested were cloned into a vector that also expresses a puromycin resistance marker. Treatment of cultures with puromycin effectively killed any non-transfected cells within the 24 hour treatment period. FIG. 12B: Results of a single experiment showing the effects of expressing a range of proteins as fusions to the tetracycline repressor on HAC stability. Results are expressed as percentage of cells showing 0, 1 or 2 copies of the HAC per nucleus, as detected by FISH for the BAC probe. FIG. 12C: Results from three experiments show that transcriptional activators (tTA, tTA3 and tTA4) cause a significant destabilization of the HAC. To correct for variability in transfection and killing efficiency, all values were normalized to the results of the transfection control (empty vector bearing puromycin resistance—black bars in FIG. 12B). Constructs that were indistinguishable from the control have a value on the ordinate of 1.0. RFP-TetR and CENP-H RFP were essentially identical to the control, while RFP-HP1 and RFP-CENP-A showed a slight, and statistically insignificant, tendency to destabilize the HAC.

FIGS. 14A-14D are a series of micrographs, showing targeting of a transcriptional activator into the kinetochore causes the HAC to mis-segregate at mitosis. The HAC (detected by FISH and indicated with arrows) fails to segregate with the bulk chromosomes (stained with DAPI—shown in FIGS. 14A and 14B) in anaphase. Micronucleus revealed by DAPI staining (FIG. 14C) contains the HAC (FIG. 14D), as revealed by FISH with the BAC probe. The HAC is indicated by arrows.

SEQUENCE LISTING

Figure 1:
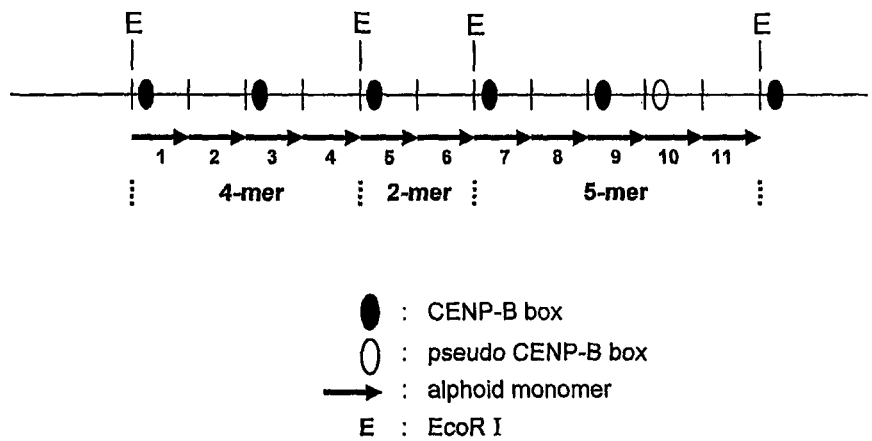
FIG. 1 is a schematic representation of the organization of the 11-mer alphoid DNA unit from the human chromosome 21. This unit is repeated thousands of times in the centromeric region of chromosome 21, and represents a functional core of the centromere. Arrays of this unit are highly competent in formation of HACs when transformed into human cells.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand.

SEQ ID NOs: 1-6 are upper (1-3) and lower (4-6) strand RCA primers for alphoid DNA.
SEQ ID NOs: 7-10 are upper (7,8) and lower (9,10) strand primers for the mouse major satellite.
SEQ ID NOs: 11-13 are upper (11,12) and lower (13) strand primers for the mouse minor satellite.
SEQ ID NOs: 14-16 are upper (14) and lower (15,16) strand primers for the human gamma-8 satellite.
SEQ ID NOs: 17-19 are upper (17,18) and lower (19) strand primers for the human Alu repeat.
SEQ ID NO: 20 is a primer for the Mouse major F repeat.
SEQ ID NO: 21 is a primer for the Mouse major R repeat.
SEQ ID NO: 22 is a primer for the Mouse minor F repeat.
SEQ ID NO: 23 is a primer for the Mouse minor R repeat.
SEQ ID NOs: 24 (forward) and 25 (reverse) are primers for the Alu repeats.
SEQ ID NOs: 26 (forward) and 27 (reverse) are primers for the Gamma 8 repeats.
SEQ ID NOs: 28-37 are representative targeting hooks for the Mouse major satellite (28, 29), Mouse minor satellite (30, 31), Alu repeats (32,33), Gamma 8 repeats (34,35), and Human alpha satellite (36,37).
SEQ ID NO: 38 is a CENP-B consensus sequence.
SEQ ID NO: 39 is a p11-4 alphoid DNA probe.
SEQ ID NO: 40 is a Vector probe.
SEQ ID NOs: 41 and 42 are the BACX and BACS primers, respectively.
SEQ ID NOs: 43 and 44 are primers alpha(1)18a and alpha(1)18b, respectively.
SEQ ID NOs: 45 and 46 are primers alpha(Y)a and alpha(Y)b, respectively.
SEQ ID NOs: 47 and 48 are primers CB15a and CB15b, respectively.

DETAILED DESCRIPTION

I. Abbreviations

ARS: yeast origin of replication
BAC: bacterial artificial chromosome
CEN: yeast centromere
DNA: deoxyribonucleic acid
FISH: fluorescent in situ hybridization
HAC: human artificial chromosome
HOR: higher-order repeat
MAC: mammalian artificial chromosome
ORF: open reading frame
PCR: polymerase chain reaction
RCA: rolling circle amplification
TAR: transformation-associated recombination
YAC: yeast artificial chromosome II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments, the following explanations of specific terms are provided:

5' and/or 3': Nucleic acid molecules (such as, DNA and RNA) are said to have "5' end" and "3' ends" because mononucleotides are reacted to make polynucleotides in a manner such that the 5' phosphate of one mononucleotide pentose ring is attached to the 3' oxygen of its neighbor in one direction via a phosphodiester linkage. Therefore, one end of a linear polynucleotide is referred to as the "5' end" when its 5' phosphate is not linked to the 3' oxygen of a mononucleotide pentose ring. The other end of a polynucleotide is referred to as the "3' end" when its 3' oxygen is not linked to a 5' phosphate of another mononucleotide pentose ring. Notwithstanding that a 5' phosphate of one mononucleotide pentose ring is attached to the 3' oxygen of its neighbor, an internal nucleic acid sequence also may be said to have 5' and 3' ends.

In either a linear or circular nucleic acid molecule, discrete internal elements are referred to as being "upstream" or 5' of the "downstream" or 3' elements. With regard to DNA, this terminology reflects that transcription proceeds in a 5' to 3' direction along a DNA strand. Promoter and enhancer elements, which direct transcription of a linked gene, are generally located 5' or upstream of the coding region. However, enhancer elements can exert their effect even when located 3' of the promoter element and the coding region. Transcription termination and polyadenylation signals are located 3' or downstream of the coding region.

Alphoid DNA (alpha satellite DNA): Alphoid DNA is the abundant family of repeated DNA elements associated with human centromeres. The general nature of alphoid DNA is reviewed, for instance, in Willard and Waye (TIG 3:192-197, 1987) and Choo et al. (*Nucleic Acids Res.* 19, 1179-1182, 1991), wherein the authors provide a consensus sequence based on analysis of 130 alpha monomers isolated from high order repeat units in at least 14 different human chromosomes. Of the sequences analyzed, 15-20% divergence of individual monomers from the consensus was noted.

Alu sequence: A repeated, relatively conserved sequence of about 300 bp that often contains a cleavage site for the restriction enzyme AluI near the center; about 1 million copies occur throughout the human genome. A representative Alu sequence can be found in GI:408373 (which is incorporated herein by reference as of the date of filing of this application).

Amplifying a nucleic acid: To increase the number of copies of a nucleic acid. The resulting amplification products are called "amplicons."

Cassette: A nucleic acid sequence encoding at least one selectable marker that can be inserted into the genome of a cell or into a plasmid or artificial chromosome, for instance a prokaryotic or eukaryotic cell. In one embodiment, the cassette includes a reporter gene such a nucleic acid sequence that confers resistance to an antibiotic in a host cell in which the nucleic acid is translated. Examples of antibiotic resistance genes include, but are not limited to, genes that provide resistance to: kanamycin, ampicillin, tetracycline, chloramphenicol, neomycin, hygromycin, and zeocin.

Commonly used yeast genetic markers include URA3, LYS2, TRP1, LEU2, HIS3, ADE2, and G418R. Less frequently used yeast genetic markers include $CYH2^S$ and $CAN1^S$ (determining sensitivity to cycloheximide and canavanine, respectively); KlURA3 (from *Kluyveromyces lactis* and homologous to *S. cerevisiae* URA3, both of which determine resistance to 5-FOA); hygromicin$B^R$ (determining resistance to hygromicin); and NAT$^R$ (Nourseothricin) (determining resistance to nourseothricin).

Counter-selectable markers (markers for which there is a system where loss of the marker can be selected for) in yeast include URA3, KlURA3, CYH2, CAN1, TRP1, and LYS2. In certain embodiments, counter-selectable markers URA3 and KlURA3 are particularly beneficial because the majority of yeast strains have a mutation in the URA3 gene (ura$^-$ strains), and the frequency of spontaneous reversions is low. KlURA3 is preferred to URA3 because it can substitute URA3 of *S. cerevisiae*, but it is at the same time divergent enough to reduce the possibility of gene conversion with the chromosomal mutated copy of URA3 in ura$^-$ strains.

Other counter-selectable markers are toxic gene products that, when expressed or over-expressed, prevent growth and/or kill the host cell. Included in this class of counter-selectable markers are restriction enzymes such as EcoRI (Lewis et al., *Mol. Cell. Biol.* 18: 1891-1902, 1998) and PvuII, and the gene that encodes p53 and toxic versions of the p53 gene (Inga and Resnick, *Oncogene* 20: 3409-3419, 2001) from humans and other mammals. These counter-selectable genes are generally used under a highly regulatable promoter (that provides a low basal level and a high inducible level). In some embodiments, the expressed PvuII gene may have modifications either in the coding sequence or in a GAL1 or other inducible promoter used to drive expression of the gene. These are each examples of markers that can provide counter-election in a broad range of biological systems for which more conventional counter-selectable markers may not be available or are inconvenient. These counter-selectable markers are thus considered "universal" or "generic," in that they are not dependent (or are only indirectly or minimally dependent) on the species or genetic background of the host cell.

The following markers are also considered heterologous markers in yeast, since the involved genetic sequence is not native to *S. cerevisiae* but has been added from a different species: KlURA3, G418$^R$, hygromicin$^R$, NAT$^R$, and p53.

cDNA (complementary DNA): A piece of DNA lacking internal, non-coding segments (introns) and regulatory sequences which determine transcription. cDNA may be synthesized in the laboratory by reverse transcription from messenger RNA extracted from cells.

CENP-B box: A sequence of DNA to which a centromeric (CENP-B) protein binds. Centromere protein (CENP) B boxes, recognition sequences of CENP-B, appear at regular intervals in human centromeric alpha-satellite DNA (alphoid DNA) (Masumoto et al., *J. Cell Biol.*, 109:1963-1973, 1998). It has been suggested that CENP-B boxes are important for centromere function (Ohzeki et al., *J. Cell Biol.*, 159:765-775, 2002), because efficient MAC formation was observed with alphoid DNA constructs containing the protein binding sites. CENP-B boxes have been studied and described (Ikeno et al., *Hum. Mol. Genet.* 3:1245-1257, 1994). The following consensus sequence has been established: 5'-NTTCGNNN-NANNCGGGN-3' (wherein N is any of A, T, C, or G; SEQ ID NO: 38) (Masumoto et al., *NATO ASI Series V H*72, Springer-Verlag, pp. 31-43, 1993; Yoda et al., *Mol. Cell. Biol.*, 16:5169-5177, 1996; U.S. patent publication 2002/0076811).

Concatamer: Two or more identical linear molecular units, such as nucleic acid sequences, covalently linked in tandem.

Deletion: The removal of a sequence of DNA, the regions on either side of the removed sequence being joined together. Correspondingly, a deletion in a protein is the removal of a region of amino acid sequence of the protein or peptide. Deletions can be quite short, for instance only one or a few nucleic acids to 10, 15, 20, 25, 30, 50, 80, or 100 nucleic acids or longer, and may be quite long. In particular embodiments long deletions may be at least 500 nucleic acids, at least 750, at least 1000, at least 2500, at least 3000, at least 5000, at least 8000, at least 10,000, or more nucleic acids in length. Particularly long deletions may be over 10,000 nucleic acids, for instance as long as 15,000, 20,000, 30,000, or more.

DNA (deoxyribonucleic acid): DNA is a long chain polymer that comprises the genetic material of most living organisms (some viruses have genes comprising ribonucleic acid, RNA). The repeating units in DNA polymers are four different nucleotides, each of which comprises one of the four bases, adenine, guanine, cytosine, and thymine bound to a deoxyribose sugar to which a phosphate group is attached. Triplets of nucleotides, referred to as codons, in DNA molecules code for amino acid in a polypeptide. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule.

Double strand break: Breaks that occur in the DNA backbones of both strands at approximately the same nucleotide pair are called double-strand breaks. This is in contrast to a nick, which indicates that only one DNA backbone is broken at a particular nucleotide.

Endonuclease: An enzyme that breaks (cleaves, cuts) the internal phosphodiester bonds in a DNA molecule.

Engineered centromeric sequence/region: An engineered nucleic acid sequence comprising a tandem array of repeated sequences generated, for instance, through rolling circle amplification of a starting repeat sequence or direction in vitro ligation of an array of repeat sequences. In most instances, the starting array of repeats, once assembled into a synthetic long tandem repeat sequence, will be further concatamerized by tandem capture mediated by in vivo recombination (e.g., TAR in yeast).

As provided herein, engineered centromeric sequences/regions are competent to provide chromosome-like meiotic and/or mitotic activity to a nucleic acid molecule of which they are part. Thus, for instance, an engineered centromeric sequence confers some or all of the functions of a native centromere (e.g., centromere-like activities) to a vector containing the engineered centromeric sequence. Centromeric-like activities include: (direct or indirect) spindle fiber attachment, chromosome orientation during cell splitting, mitotic stability, meiotic stability, and so forth. In specific embodiments, there are provided long synthetic tandem repeats that are competent for use as a centromeric region in an artificial chromosome.

Flanking: Near or next to, also, including adjoining, for instance in a linear or circular polynucleotide, such as a DNA molecule.

Gene: A nucleic acid sequence, typically a DNA sequence, that comprises control and coding sequences necessary for the transcription of an RNA, whether an mRNA or otherwise. For instance, a gene may comprise a promoter, one or more enhancers or silencers, a nucleic acid sequence that encodes a RNA and/or a polypeptide, downstream regulatory sequences and, possibly, other nucleic acid sequences involved in regulation of the expression of an mRNA.

As is well known in the art, most eukaryotic genes contain both exons and introns. The term "exon" refers to a nucleic acid sequence found in genomic DNA that is bioinformatically predicted and/or experimentally confirmed to contribute a contiguous sequence to a mature mRNA transcript. The term "intron" refers to a nucleic acid sequence found in genomic DNA that is predicted and/or confirmed not to contribute to a mature mRNA transcript, but rather to be "spliced out" during processing of the transcript. "RefSeq genes" are those genes identified in the National Center for Biotechnology Information RefSeq database, which is a curated, non-redundant set of reference sequences including genomic DNA contigs, mRNAs and proteins for known genes, and entire chromosomes (The NCBI handbook [Internet], Bethesda (MD): National Library of Medicine (US), National Center for Biotechnology Information; 2002 October Chapter 18, The Reference Sequence (RefSeq) Project; available from the NCBI website).

Gene therapy: The introduction of a heterologous nucleic acid molecule into one or more recipient cells, wherein expression of the heterologous nucleic acid in the recipient cell affects the cell's function and results in a therapeutic effect in a subject. For example, the heterologous nucleic acid molecule may encode a protein, which affects a function of the recipient cell. In another example, the heterologous nucleic acid molecule may encode an anti-sense nucleic acid that is complementary to a nucleic acid molecule present in the recipient cell, and thereby affect a function of the corresponding native nucleic acid molecule. In still other examples, the heterologous nucleic acid may encode a ribozyme or deoxyribozyme, which are capable of cleaving nucleic acid molecules present in the recipient cell. In another example, the heterologous nucleic acid may encode a so-called decoy molecule, which is capable of specifically binding a peptide molecule present in the recipient cell.

Genomic DNA: The DNA originating within the nucleus and containing an organism's genome, which is passed on to its offspring as information for continued replication and/or propagation and/or survival of the organism. The term can be used to distinguish between other types of DNA, such as DNA found within plasmids or organelles. The "genome" is all the genetic material in the chromosomes of a particular organism.

Heterologous: A sequence that is not normally (i.e., in the wild-type sequence) found adjacent to a second sequence. In one embodiment, the sequence is from a different genetic source, such as a virus or other organism, than the second sequence.

Hybridization: Poly- and oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

"Specifically hybridizable" and "specifically complementary" are terms that indicate a sufficient degree of complementarity such that stable and specific binding occurs between the poly- or oligonucleotide (or its analog) and the DNA or RNA target. The poly- or oligonucleotide (or its analog) need not be 100% complementary to its target sequence to be specifically hybridizable. A nucleotide molecule or analog thereof is specifically hybridizable when its binding to a target DNA or RNA molecule occurs with a sufficient degree of complementarity to avoid non-specific binding of the nucleotide or analog to non-target sequences under conditions where specific binding is desired, for example under physiological conditions in the case of in vivo assays or systems. Such binding is referred to as specific hybridization.

Hybridization conditions resulting in particular degrees of stringency will vary depending on the nature of the hybridization method of choice and the composition and length of the hybridizing nucleic acid sequences. Generally, the temperature of hybridization and the ionic strength (especially the $Na^+$ concentration) of the hybridization buffer will determine the stringency of hybridization, though wash times also influence stringency. Calculations regarding hybridization conditions required for attaining particular degrees of stringency are discussed by Sambrook et al. (ed.), *Molecular Cloning: A Laboratory Manual,* 2nd ed., vol. 1-3, Cold Spring Harbor Laboratory Press, Cold Spring Harbor, N.Y., 1989, chapters 9 and 11, incorporated herein by reference.

By way of illustration, hybridization is generally carried out in vitro in a solution of high ionic strength such as 6×SSC at a temperature that is 20-25° C. below the melting temperature, $T_m$, described below. For instance, for Southern hybridization experiments where the target DNA molecule on the Southern blot contains 10 ng of DNA or more, hybridization is typically carried out for 6-8 hours using 1-2 ng/ml radiolabeled poly- or oligonucleotide probe (of specific activity equal to $10^9$ CPM/μg or greater, for instance). Following hybridization, the nitrocellulose filter (Southern blot) is washed to remove background hybridization. The washing conditions should be as stringent as possible to remove background hybridization but to retain a specific hybridization signal.

The term $T_m$ represents the temperature above which, under the prevailing ionic conditions, the probe nucleic acid molecule will not hybridize to its target DNA molecule. The $T_m$ of such a hybrid molecule may be estimated from the following equation:

$$T_m = 81.5°\text{C} - 16.6(\log_{10}[\text{Na}^+]) + 0.41(\% G+C) - 30.63(\% \text{ formamide}) - (600/l)$$

Where l=the length of the hybrid in base pairs.

This equation is valid for concentrations of $\text{Na}^+$ in the range of 0.01 M to 0.4 M, and it is less accurate for calculations of $T_m$ in solutions of higher $[\text{Na}^+]$. The equation is also primarily valid for DNAs whose G+C content is in the range of 30% to 75%, and it applies to hybrids greater than 100 nucleotides in length (the behavior of oligonucleotide probes is described in detail in Ch. 11 of Sambrook et al., 1989). Thus, by way of example, for a 150 base pair DNA probe with a hypothetical GC content of 45%, a calculation of hybridization conditions required to give particular stringencies may be made as follows:

For this example, it is assumed that the filter will be washed in 0.3×SSC solution following hybridization, thereby
$[\text{Na}^+]$=0.045M
% GC=45%
Formamide concentration=0
l=150 base pairs $$T_m = 81.5 - 16(\log_{10}[\text{Na}^+]) + (0.41 \times 45) - (600/150)$$

and so $T_m$=74.4° C.

The $T_m$ of double-stranded DNA decreases by 1-1.5° C. with every 1% decrease in homology (Bonner et al., *J. Mol. Biol.* 81:123-135, 1973). Therefore, for this given example, washing the filter in 0.3×SSC at 59.4-64.4° C. will produce a stringency of hybridization equivalent to 90%; that is, DNA molecules with more than 10% sequence variation relative to the target cDNA will not hybridize. Alternatively, washing the hybridized filter in 0.3×SSC at a temperature of 65.4-68.4° C. will yield a hybridization stringency of 94%; that is, DNA molecules with more than 6% sequence variation relative to the target cDNA molecule will not hybridize. The above examples are given entirely by way of theoretical illustration. One skilled in the art will appreciate that other hybridization techniques may be utilized and that variations in experimental conditions will necessitate alternative calculations for stringency.

For purposes of the present disclosure, the term "stringent conditions" generally encompasses conditions under which hybridization will only occur if there is less than 25% mismatch between the hybridization probe and the target sequence. "Stringent conditions" may be broken down into particular levels of stringency for more precise distinction. Thus, as used herein, "moderately stringent" conditions are those under which DNA molecules with more than 25% sequence variation (also termed "mismatch") will not hybridize; "medium stringent" conditions are those under which DNA molecules with more than 15% mismatch will not hybridize, and "highly stringent" conditions are those under which DNA sequences with more than 10% mismatch will not hybridize. "Very highly stringent" conditions are those under which DNA sequences with more than 6% mismatch will not hybridize.

In vitro amplification: Techniques that increase the number of copies of a nucleic acid molecule in a sample or specimen. An example of in vitro amplification is the polymerase chain reaction (PCR), in which a nucleic acid molecule (such as one contained in a biological sample collected from a subject) is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid.

The product of in vitro amplification may be characterized by electrophoresis, restriction endonuclease cleavage patterns, oligonucleotide hybridization or ligation, and/or nucleic acid sequencing, using standard techniques.

Other examples of in vitro amplification techniques include strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134). Also encompassed in the term in vitro amplification is rolling-circle amplification.

Isolated: An isolated biological component (such as a nucleic acid, peptide, protein, or organelle) has been substantially separated, produced apart from, or purified away from other biological components in the cell of the organism in which the component naturally occurs, i.e., other chromosomal and extra-chromosomal DNA and RNA, proteins, or organelles.

Nucleic acids, peptides, and proteins that have been isolated include nucleic acids and proteins purified by standard purification methods. The term also embraces nucleic acids, peptides and proteins prepared by recombinant expression in a host cell as well as chemically synthesized nucleic acids.

Ligation: The process of forming phosphodiester bonds between two or more polynucleotides, such as between double-stranded DNAs, or between a linker and an integration junction fragment. Techniques for ligation are well known to the art and protocols for ligation are described in standard laboratory manuals and references, such as, for example, Sambrook et al., *Molecular Cloning: A Laboratory Manual*, 2d ed., Cold Spring Harbor Laboratory Press, 1989.

Mammalian Repeat Sequence: Repeat sequences are very common in mammalian genomes. Generally, mammalian repeat sequences include simple sequence repeats, microsatellites, minisatellites, megasatellites, and repeating units found in tandemly repeated sequences in a mammalian genome (e.g., centromeres, telomeres, and short arms of acrocentric chromosomes), as well as segmental duplications interspersed throughout the genome. Particularly contemplated are interspersed elements, including long interspersed elements (LINEs) and short interspersed elements (SINEs), as well as alphoid DNA. In general, interspersed elements are about 100-500 bp in length, and occur up to about 1,000,000 times in a genome. In primates, a main type of interspersed repeat is the Alu repeat (named for the AluI restriction site usually found in this repeat).

Nucleic acid molecule: A single- or double-stranded polymeric form of nucleotides, including both sense and antisense strands of RNA, cDNA, genomic DNA, and synthetic forms and mixed polymers of the above. A nucleotide refers to a ribonucleotide, deoxynucleotide or a modified form of either type of nucleotide. A "nucleic acid molecule" as used herein is synonymous with "nucleic acid" and "polynucleotide." The term includes single- and double-stranded forms of DNA or RNA. A polynucleotide may include either or both naturally occurring and modified nucleotides linked together by naturally occurring and/or non-naturally occurring nucleotide linkages.

Nucleic acid molecules may be modified chemically or biochemically or may contain non-natural or derivatized nucleotide bases, as will be readily appreciated by those of ordinary skill in the art. Such modifications include, for example, labels, methylation, substitution of one or more of the naturally occurring nucleotides with an analog, internucleotide modifications, such as uncharged linkages (for example, methyl phosphonates, phosphotriesters, phosphoramidates, carbamates, etc.), charged linkages (for example, phosphorothioates, phosphorodithioates, etc.), pendent moieties (for example, polypeptides), intercalators (for example, acridine, psoralen, etc.), chelators, alkylators, and modified linkages (for example, alpha anomeric nucleic acids, etc.).

The term "nucleic acid molecule" also includes any topological conformation of such molecules, including single-stranded, double-stranded, partially duplexed, triplexed, hairpinned, circular and padlocked conformations. Also included are synthetic molecules that mimic polynucleotides, for instance, in their ability to bind to a designated sequence via hydrogen bonding and other chemical interactions. Such molecules are known in the art and include, for example, those in which peptide linkages substitute for phosphate linkages in the backbone of the molecule.

Unless specified otherwise, each nucleotide sequence is set forth herein as a sequence of deoxyribonucleotides. It is intended, however, that the given sequence be interpreted as would be appropriate to the polynucleotide composition: for example, if the isolated nucleic acid is composed of RNA, the given sequence intends ribonucleotides, with uridine substituted for thymidine.

Nucleotide: This term includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Oligonucleotide: A linear polynucleotide sequence usually of up to about 200 nucleotide bases in length, for example a polynucleotide (such as DNA or RNA) which is at least six nucleotides, for example at least 15, 20, 50, 100 or even 200 nucleotides long. In certain embodiments, it is envisioned that oligonucleotides may be over 200 nucleotides in length, for instance, 220, 250, 270, 290, 300, 350, 400 or more nucleotides.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

ORF (open reading frame): A series of nucleotide triplets (codons) coding for amino acids. These sequences are usually translatable into a peptide.

Ortholog: Two nucleotide sequences are orthologs of each other if they share a common ancestral sequence, and diverged when a species carrying that ancestral sequence split into two species. Orthologous sequences are also homologous sequences.

Polynucleotide: A linear nucleic acid sequence of any length. Therefore, a polynucleotide includes molecules which are at least 15, 20, 50, 100, 200, 250, 300, 400 (e.g., oligonucleotides) or more, and also including nucleotides as long as a full length cDNAs, genes, or chromosomes.

Peptide Nucleic Acid (PNA): An oligonucleotide analog with a backbone comprised of monomers coupled by amide (peptide) bonds, such as amino acid monomers joined by peptide bonds.

Probes and primers: A probe comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al., *Molecular Cloning: A Laboratory Manual*, Cold Spring Harbor Laboratory Press (1989); and Ausubel et al., *Current Protocols in Molecular Biology*, Greene Publishing Associates and Wiley-Intersciences (1987).

Primers are short nucleic acids, for example DNA oligonucleotides at least about six nucleotides in length, and/or no longer than 10, 20, 50, 100 or 200 nucleotides in length, though in some embodiments they are longer. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by PCR or other nucleic acid amplification methods known in the art.

Methods for preparing and using probes and primers are described, for example, in Sambrook et al (*Molecular Cloning: A Laboratory Manual*, Cold Spring Harbor Laboratory Press, 1989), Ausubel et al., *Current Protocols in Molecular Biology*, Greene Publishing Associates and Wiley-Intersciences (1987), and Innis et al., *PCR Protocols, A Guide to Methods and Applications,* 1990, Innis et al (eds.), 21-27, Academic Press, Inc., San Diego, Calif. PCR primer pairs can be derived from a known sequence, for example, by using computer programs intended for that purpose, such as Primer (Version 0.5, ©1991, Whitehead Institute for Biomedical Research, Cambridge, Mass.).

Probes and primers comprise at least ten nucleotides of a nucleic acid sequence, although a shorter nucleic acid (e.g., six nucleotides) may be used as a probe or primer if it specifically hybridizes under stringent conditions with a target nucleic acid by methods well known in the art. One of skill in the art will appreciate that the specificity of a particular probe or primer increases with its length. Thus, for example, a primer comprising 20 consecutive nucleotides of a sequence will anneal to a target sequence (for instance, contained within a genomic DNA library) with a higher specificity than a corresponding primer of only 15 nucleotides. To enhance specificity, longer probes and primers can be used, for example probes and primers that comprise at least 20, 30, 40, 50, 60, 70, 80, 90, 100 or more consecutive nucleotides from any region of a target.

When referring to a probe or primer, the term "specific for (a target sequence)" indicates that the probe or primer hybridizes under stringent conditions substantially only to the target sequence in a given sample comprising the target sequence.

Promoter: An array of nucleic acid control sequences which direct transcription of a nucleic acid. A promoter includes necessary nucleic acid sequences near the start site of transcription, such as, in the case of a polymerase II type promoter, a TATA element. In one embodiment, a promoter includes an enhancer. In another embodiment, a promoter includes a repressor element. In these embodiments, a chimeric promoter is created (a promoter/enhancer chimera or a promoter/repressor chimera, respectively). Enhancer and repressor elements can be located adjacent to, or distal to the promoter, and can be located as much as several thousand base pairs from the start site of transcription. Examples of promoters include, but are not limited to the SV40 promoter, the CMV enhancer-promoter, the CMV enhancer/β-actin promoter, and the tissue-specific promoter probasin.

Other promoter sequences which can be used to construct the nucleic acids and practice the methods disclosed herein include, but are not limited to: the lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors, any retroviral LTR promoter such as the RSV promoter; inducible promoters, such as the MMTV promoter; the metallothionein promoter; heat shock promoters; the albumin promoter; the histone promoter; the α-actin promoter; TK promoters; B19 parvovirus promoters; the SV10 late promoter; the ApoAI promoter and combinations thereof.

In one embodiment, a promoter is a strong promoter, which promotes transcription of RNA at high levels, for example at levels such that the transcriptional activity of the promoter generally accounts for about 25% of transcriptional activity of all transcription within a cell. The strength of a promoter is often tissue-specific and thus may vary from one cell type to another. For example, CMV is a classic strong promoter because it generates high levels of transcriptional activity in many cell types. Examples of strong promoters include, but are not limited to: CMV; CMV/chicken β-actin; elongation factors 1A and 2A; SV40; RSV; and the MoLV LTR.

In another embodiment, a promoter is a tissue-specific promoter, which promotes transcription in a single cell type or narrow range of tissues. Examples of tissue-specific promoters include, but are not limited to: probasin (which promotes expression in prostate cells), an immunoglobulin promoter; a whey acidic protein promoter; a casein promoter; glial fibrillary acidic protein promoter; albumin promoter; β-globin promoter; and the MMTV promoter.

In yet another embodiment, a promoter is a hormone-responsive promoter, which promotes transcription only when exposed to a hormone. Examples of hormone-responsive promoters include, but are not limited to: probasin (which is responsive to testosterone and other androgens); MMTV promoter (which is responsive to dexamethazone, estrogen, and androgens); and the whey acidic protein promoter and casein promoter (which are responsive to estrogen).

For expression of eukaryotic genes in yeast, there are a variety of promoters to choose from for various purposes. The following are provided by way of example, and are not meant to be in any way limiting:

The Gal 1,10 promoter: This promoter is inducible by galactose. It is frequently valuable to be able to turn expression of your gene on and off so you can follow the time dependent effects of expression. The Gal promoter is slightly leaky, and so is appropriate where it is not essential to have absolutely no expression of the passenger gene in the absence of galactose. The Gal 1 gene and Gal 10 gene are adjacent and transcribed in opposite directions from the same promoter region. The regulatory region containing the UAS sequences can be cut out on a DdeI Sau3A fragment and placed upstream of any other gene to confer galactose inducible expression and glucose repression.

PGK, GPD and ADH1 promoters: These are high expression constitutive promoters. PGK=phosphoglycerate kinase, GPD=glyceraldehyde 3 phosphate dehydrogenase, ADH1=alcohol dehydrogenase ADH2 promoter: This gene is glucose repressible and it is strongly transcribed on non-fermentable carbon sources (similar to GAL 1,10 except not inducible by galactose).

CUP1 promoter: This is the metalothionein gene promoter. It is activated by copper or silver ions added to the medium. The CUP1 gene is one of a few yeast genes that is present in yeast in more than one copy. Depending on the strain, there can be up to eight copies of this gene.

PHO5 promoter: This promoter is derived from a gene that encodes an acid phosphatase. It is induced by low or no phosphate in the medium. The phosphatase is secreted in the chance it will be able to free up some phosphate from the surroundings. When phosphate is present, PHO5 message is s low as to be essentially undetectable. When phosphate is absent, this promoter is turned on strongly.

Protein: A biological molecule expressed by a gene or other encoding nucleic acid (e.g. a cDNA) and comprised of amino acids.

Purified: The term purified does not require absolute purity; rather, it is intended as a relative term. Thus, for example, a purified protein (or nucleic acid) preparation is one in which the protein (or nucleic acid) is more pure than the molecule in its natural environment within a cell (or other production vessel). In one embodiment, a preparation of a molecule is purified such that the molecule represents at least 50%, for example at least 70%, of the total content of the preparation.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Sambrook et al. (In: *Molecular Cloning: A Laboratory Manual*, Cold Spring Harbor, N.Y., 1989).

Regulated (or Conditional) Centromere (or Chromosome): A regulated or conditional centromere is a synthetic centromere the function of which can be altered, e.g., experimentally or through the application of a compound or drug or other influence. For instance, the function can be turned on or off (or made more or less effective) by a change in or manipulation of condition(s). One example of a change in or manipulation of a condition is expression/repression of protein(s) that are capable of binding to the synthetic centromere and thereby activate or inactivate (to some degree) a centroinere function. Inactivation of centromere function results in some level of chromosome loss, which loss can be detected, measured and/or tracked for instance using methods discussed and described herein. A chromosome containing a regulated (conditional) centromere may be referred to as a regulated (or conditional) chromosome.

Restriction Endonuclease or Restriction Enzyme: A protein (usually derived from bacteria) that cleaves a double-stranded nucleic acid, such as DNA, at or near a specific sequence of nucleotide bases, which is called a recognition site. A recognition site is typically four to eight base pairs in length and is often a palindrome. In a nucleic acid sequence, a shorter recognition site is statistically more likely to occur than a longer recognition site. Thus, restriction enzymes that recognize specific four- or five-base pair sequences will cleave a nucleic acid substrate relatively frequently and may be referred to as "frequent cutters."

Some restriction enzymes cut straight across both strands of a DNA molecule to produce "blunt" ends. Other restriction enzymes cut in an offset fashion, which leaves an overhanging piece of single-stranded DNA on each side of the cleavage point. These overhanging single strands are called "sticky ends" because they are able to form base pairs with a complementary sticky end on the same or a different nucleic acid molecule. Overhangs can be on the 3' or 5' end of the restriction site, depending on the enzyme.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are. Homologs or orthologs of a target protein, and the corresponding cDNA or gene sequence(s), will possess a relatively high degree of sequence identity when aligned using standard methods. This homology will be more significant when the orthologous proteins or genes or cDNAs are derived from species that are more closely related (e.g., human and chimpanzee sequences), compared to species more distantly related (e.g., human and *C. elegans* sequences).

Methods of alignment of sequences for comparison are well known in the art. Various programs and alignment algorithms are described in: Smith & Waterman *Adv. Appl. Math.* 2: 482, 1981; Needleman & Wunsch *J. Mol. Biol.* 48: 443, 1970; Pearson & Lipman *Proc. Natl. Acad. Sci. USA* 85: 2444, 1988; Higgins & Sharp *Gene,* 73: 237-244, 1988; Higgins & Sharp *CABIOS* 5: 151-153, 1989; Corpet et al. *Nuc. Acids Res.* 16, 10881-90, 1988; Huang et al. *Comp. Appls. Biosciences* 8, 155-65, 1992; and Pearson et al. *Meth. Mol. Bio.* 24, 307-31, 1994. Altschul et al. (*J. Mol. Biol.* 215:403-410, 1990), presents a detailed consideration of sequence alignment methods and homology calculations.

The NCBI Basic Local Alignment Search Tool (BLAST) (Altschul et al. *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx. When aligning short sequences (fewer than around 30 nucleic acids), the alignment can be performed using the BLAST short sequences function, set to default parameters (expect 1000, word size 7).

Since MegaBLAST requires a minimum of 28 bp of sequence for alignment to the genome, Pattern Match (available from the Protein Information Resource (PIR) at Georgetown, and at their on-line website) can be optimally used to align short sequences, such as the 15-30 bp, or more preferably about 20 to 22 bp, tags generated in concatamerized embodiments. This program can be used to identify the location of genomic tags within the genome. Another program that can be used to look for perfect matches between the 20 bp tags is 'exact match,' which is a PERL computer function that looks for identical matches between two sequences (one being the genome, the other being the 20 bp tag). Since it is expected that there will be single nucleotide polymorphisms within a subset of the identified tags, the exact match program cannot be used to align these tags. Instead, GRASTA (available from The Institute for Genomic Research) will be used, which is a modified FastA code that searches both nucleic acid strands in a database for similar sequences. This program is able to align fragments that contain a one (or more) base pair mismatch(es).

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence remains hybridized to a perfectly matched probe or complementary strand. Conditions for nucleic acid hybridization and calculation of stringencies can be found in Sambrook et al. (In *Molecular Cloning: A Laboratory Manual*, CSHL, New York, 1989) and Tijssen (*Laboratory Techniques in Biochemistry and Molecular Biology—Hybridization with Nucleic Acid Probes* Part I, Chapter 2, Elsevier, N.Y., 1993). Nucleic acid molecules that hybridize under stringent conditions to a protein-encoding sequence will typically hybridize to a probe based on either an entire protein-encoding or a non-protein-encoding sequence or selected portions of the encoding sequence under wash conditions of 2×SSC at 50° C.

Nucleic acid sequences that do not show a high degree of sequence identity may nevertheless encode similar amino acid sequences, due to the degeneracy of the genetic code. It is understood that changes in nucleic acid sequence can be made using this degeneracy to produce multiple nucleic acid molecules that all encode substantially the same protein. Further one of ordinary skill in the art will appreciate that these sequence identity ranges are provided for guidance only; it is entirely possible that significant homologs can be obtained that fall outside of the ranges provided.

Subject: Living multi-cellular vertebrate organisms, particularly a mammal, including human and veterinary subjects, such as cows, pigs, horses, dogs, cats, birds, reptiles, mice, rats, and fish.

Transformation-associated recombination (TAR) cloning: A system that allows for selective recombination of two or more sequences, for instance in order to concatenate and capture elements of an engineered centromeric region (e.g., a long synthetic tandem repeat sequence) into a MAC. TAR cloning involves direct isolation of a nucleic acid sequence, usually a specific target nucleic acid sequence or concatamer comprising more than one copy of the target sequence, from a complex mixture of nucleic acid sequences (e.g., a genome), in the form of a circular YAC.

Isolation of specific chromosomal regions and entire genes has typically involved a long and laborious process of identification of the region of interest among thousands random YAC clones. Using the TAR cloning technique in the yeast *Saccharomyces cerevisiae*, it is possible to directly isolate specific chromosomal regions and genes from complex genomes as large linear or circular YACs (Kouprina and Larionov, *Current Protocols in Human Genetics* 5.17-0.1-5.17.21, 1999). The speed and efficiency of TAR cloning, as compared to the more traditional methods of gene isolation, provides a powerful tool for the analysis of gene structure and function. Isolation of specific regions from complex genomes by TAR in yeast includes preparation of yeast spheroplasts and transformation of the spheroplasts by gently isolated total genomic DNA along with a TAR vector containing sequences homologous to a region of interest. Recombination between a genomic fragment and the vector results in a rescue of the region as a circular Yeast Artificial Chromosome (YAC). When both 3' and 5' ends sequence information is available for a target, that target sequence (e.g., a gene or other identified sequence) can be isolated by a vector containing two short unique sequences flanking the gene ("hooks"). Optionally, hook homology can be lowered to as low as about 85% identity, to increase recombination efficiency.

If sequence information is available only for one gene end [for example, for the 3' end based on Expressed Sequence Tag (EST) information], the gene can be isolated by a TAR vector that has one unique hook corresponding the known end and a repeated sequence as a second hook (such as Alu or B1 repeats for human or mouse DNA, respectively). Because only one of the ends is fixed, this type of cloning is called radial TAR cloning. TAR cloning produces libraries in which nearly 1% of the transformants contain the desired gene. A clone containing a gene of interest can be easily identified in the libraries by PCR.

Transduced and Transfected: A virus or vector transduces or transfects a cell when it transfers nucleic acid into the cell. A cell is "transfected" by a nucleic acid transduced into the cell when the DNA becomes stably replicated by the cell, either by incorporation of the nucleic acid into the cellular genome, or by episomal replication.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule capable of transporting another nucleic acid to which it has been linked. One type of vector is a "plasmid", which refers to a circular double-stranded DNA loop into which additional DNA segments may be ligated. Other vectors include cosmids, bacterial artificial chromosomes (BAC), yeast artificial chromosomes (YAC), and mammalian artificial chromosomes (MAC). Another type of vector is a viral vector, wherein additional DNA segments may be ligated into the viral (or virally derived) genome. Another category of vectors is integrating gene therapy vectors.

Certain vectors are capable of autonomous replication in a host cell into which they are introduced. Some vectors can be integrated into the genome of a host cell upon introduction into the host cell, and thereby are replicated along with the host genome. Some vectors, such as integrating gene therapy vectors or certain plasmid vectors, are capable of directing the expression of heterologous genes which are operatively linked to regulatory sequences (such as, promoters and/or enhancers) present in the vector. Such vectors may be referred to generally as "expression vectors."

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned or cited to herein are incorporated herein by reference in their entirety, even if the reference is not specifically incorporated. In case of conflict, the present specification, including explanations of terms, will control. The materials, methods, and examples are illustrative only and not intended to be limiting. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

III. Overview of Several Embodiments

Provided herein are methods of generating engineered centromeric sequences, both from native repeat sequences and repeat sequences that have been modified from a native sequence or synthetically produced. Also provided are methods of capturing such engineered centromeric sequences through in vivo recombination (e.g., in vivo homologous recombination) in vectors, thereby forming mammalian artificial chromosomes.

Thus, in a first exemplar embodiment there is provided a method of generating an engineered centromeric sequence, which method comprises rolling circle amplification (RCA) of a starting sequence comprising at least one mammalian repeat sequence or a synthetic sequence at least 90% identical to such a repeat sequence to produce a RCA product which is the engineered centromeric sequence. By way of example, the mammalian repeat sequence may comprise an alphoid repeat sequence, an Alu repeat sequence, a human gamma-8 satellite sequence, a mouse major satellite sequence, or a mouse minor satellite sequence. Optionally, the starting sequence further comprises a DNA sequence that is recognized by a DNA-biding protein or a specific RNA. For instance, such a sequence is a tet Operator (tetO) sequence; other sequences may be included that would be useful in regulating or rendering conditional the centromere (or a synthetic chromosome containing such a centromere). It is specifically contemplated that the RCA product produced by methods provided herein may itself be a mixture of different lengths of concatamerized repeat sequences.

In another embodiment a method of generating an engineered centromeric sequence comprises in vitro directional ligation, end to end, of copies of a starting sequence comprising at least one mammalian repeat sequence or a synthetic sequence at least 90% identical to such a repeat sequence.

Also provided are methods of generating a mammalian artificial chromosome (MAC). For instance, examples of such methods involve assembling one or more engineered centromeric sequences into a vector, wherein the engineered centromeric sequence is (1) produced by a method comprising rolling circle amplification (RCA) of a starting sequence comprising at least one mammalian repeat sequence or a synthetic sequence at least 90% identical to such a repeat sequence or (2) produced using directional in vitro ligation of multiple mammalian repeat sequences. For instance, assembling the one or more engineered centromeric sequences may involve homologous in vivo recombination, or more particularly yeast homologous recombination, such as transformation-associated recombination (TAR).

In another example of a method of generating a mammalian artificial chromosome, the vector is a transformation-associated recombination (TAR) vector. By way of illustration, such a TAR vector will include a yeast cassette, comprising: a yeast origin of replication; and a yeast selectable marker sequence; a mammalian marker sequence; and a sequence containing hooks homologous to sequence within the mammalian repeat sequence. In representative methods, the hooks comprise at least 30 contiguous nucleotides about 90% homologous to a sequence selected from an alphoid repeat, a Alu sequence, a human gamma-8 satellite, a mouse major satellite, or a mouse minor satellite. Preferably, the hook sequences are at or near the ends of such a repeat sequence. Optionally, the hook homology can be lowered to as low as about 85% identity, to increase recombination efficiency. Lower homology is feasible, but usually not optimal.

In yet other embodiments, the TAR vector further comprises: a bacterial origin of replication; and a bacterial selectable marker sequence.

It is particularly contemplated, in various methods, that the RCA product is a mixture of different lengths of concatamerized repeat sequence. By way of example, the RCA products in various embodiments will average about 1 to about 5 kb in length; average about 1 to about 10 kb in length; average more than 2 kb in length; average about 5 kb in length; or average more than about 5 kb in length. Looked at it from another way, in various embodiments the number of RCA products assembled into the artificial chromosome form a centromeric region of at least 10 kb; at least 20 kb; at least 50 kb; at least 70 kb; at least 80 kb; at least 100 kb; or more than 100 kb.

There is also provided method of making a mammalian artificial chromosome competent for maintenance in a mammalian cell, which method involves selecting a repeat sequence; amplifying the repeat sequence into a tandem repeat sequence using rolling-circle amplification (or concatamerizing the repeat sequence using directional in vitro ligation); and capturing the tandem repeat sequence in a nucleic acid molecule (such as a TAR vector) using in vivo homologous recombination to produce a mammalian artificial chromosome, wherein the mammalian artificial chromosome is competent for maintenance in a mammalian cell.

Also provided herein are regulated (or conditional) centromeres, which are synthetic centromeres the function of which can be altered through intervention (e.g., by manipulating the environment in which the centromere or an artificial chromosome containing it is present). Methods of making regulated centromeres, and regulated (conditional) artificial chromosomes containing such, are provided. Also provided are methods of using regulated centromeres and chromosomes in functional and structural analyses of centromeres, gene expression systems, pharmacology, and gene therapy.

Also contemplated herein are mammalian artificial chromosomes (MACs), made by any one of the methods provided. Optionally, such MACs also comprise at least one mammalian protein encoding sequence, such as for instance a transgene for expression in a cell to which the MAC is introduced.

IV. Methods of Producing MACs

Successful development of a Human Artificial Chromosome (HAC) cloning system would have profound effects on human gene therapy and on our understanding of the organization of human centromeric regions and a kinetochore function. Efforts so far to produce HACs have involved two basic approaches: paring down an existing functional chromosome, or building upward from DNA sequences that could potentially serve as functional elements. The first approach utilized telomere-directed chromosome fragmentation to systematically decrease chromosome size, while maintaining correct chromosomal function. The fragmentation has been targeted to both the X and Y chromosome centromere sequences by incorporating homologous sequences into the fragmentation vector. This approach has pared the Y and X chromosomes down to a minimal size of ~2.0 Mb which can be stably maintain in culture (Heller et al., *Proc. Natl. Acad. Sci. USA* 93:7125-7130, 1996; Mills et al., *Hum. Mol. Genet.* 8: 751-761, 1999; Kuroiwa et al., *Nature Biotech.* 18: 1086-1090, 2000). These deleted chromosome derivatives lost most of their chromosomal arms and up to 90% of their alphoid DNA array. None of the resultant mitotically stable derivatives contained alphoid DNA arrays shorter than ~100 kb, suggesting that this size block of alphoid DNA, alone or along with the short arm flanking sequence, is sufficient for a centromere function. The second approach was based on transfection of human cells by YAC or BAC constructs containing large arrays of alphoid DNA (Harrington et al., *Nat. Genet.* 15: 345-355, 1997, Ikeno et al., *Nature Biotech.* 16: 431439, 1998; Henning et al., *Proc. Nat. Acad. Sci. USA* 96: 592-597, 1999; Ebersole et al., *Hum. Mol. Genet.* 9:1623-1631, 2000). Because the formation of HACs was not observed with constructs containing random genomic fragments, these experiments demonstrated an absolute requirement of alphoid DNA for centromere function. In all cases formation of HACs was accompanied by 10-50-fold amplification of YAC/BAC constructs in transfected cells. Both approaches led to development of cell lines containing genetically marked chromosomal fragments exhibiting stable maintenance during cell divisions. These mini-chromosomes appear to be linear and about 2-12 Mb in size.

Further work led to the development of HACs that readily could be cloned and manipulated in microorganisms, rendering transfer to other mammalian cell types simpler. For instance, methods were developed whereby centromeric regions from mammalian chromosomes could be specifically cloned using transformation-associated recombination (see, e.g., U.S. patent publication 2004/0245317). Such isolates contain native (or near native) centromeric regions from human and other mammalian chromosomes. The isolation of such centromeric regions provided for mammalian artificial chromosomes (MACs) capable of being shuffled between bacterial, yeast and mammalian cells, such as human cells, based on the inclusion of cassettes within the MAC that would mediate maintenance of the molecule in each cell type.

Functional centromeres have been isolated from centromeric regions of human chromosomes, including the mini-chromosome ΔYq74 containing 12 Mb of the Y human chromosome (Heller et al., *Proc. Natl. Acad. Sci. USA* 93:7125-7130, 1996), and the human chromosome 22. The centromeric regions were isolated from total genomic DNA by using a novel protocol of Transformation-Associated Recombination (TAR) in yeast. TAR is a cloning technique based on in vivo recombination in yeast (Larionov et al., *Proc. Natl. Acad. Sci. USA* 93:13925-13930, 1996; Kouprina et al., *Proc. Natl. Acad. Sci. USA* 95: 4469-4474, 1998; Kouprina and Larionov, *Current Protocols in Human Genetics* 5.17.1-5.17.21, 1999). Such MACs can be vehicles for the delivery and expression of transgenes within cells and for the isolation and characterization of genes and other DNA sequences.

In other work, groups have reported construction of synthetic alphoid arrays using repetitive directional ligation on the basis of a native higher-order repeat fragment of 2-3 kb (Harrington et al., *Nat. Genet.* 15:345-355, 1997; Ohzeki et al., *J. Cell Biol.* 159, 765-775, 2002; Basu et al., *Nucleic Acids Res.* 33:587-596, 2005).

V. MACs that Incorporate Long Synthetic Tandem Repeats

We describe here in various embodiments methods to amplify tandem repeats of a few hundred bp, including particularly human alphoid tandem repeats, into long DNA arrays up to 120 kb or more that avoid a step of in vitro ligation. Examples of the methods include rolling circle amplification (RCA) of repeats in vitro and assembly of multiple copies of the RCA products by in vivo recombination in yeast to form artificial chromosomes. The synthetic arrays are competent in HAC formation when transformed into human cells; they also may be used to develop murine AC when transformed into murine cells, and so forth. Because short multimers can be easily modified before RCA amplification, these techniques can be used to identify, characterize, and alter repeat monomer regions, for instance those involved in kinetochore seeding. The methods have more general application in elucidating the role of other tandem repeats in chromosome organization and dynamics.

Synthetic tandem arrays produced using methods described herein are also useful for providing the centromeric function in artificial chromosomes, for instance mammalian artificial chromosomes (MACs) and more particularly human artificial chromosomes (HACs) or murine artificial chromosomes. Such artificial chromosomes have a variety of uses that will be recognized by those of ordinary skill in the art, including but not limited to use as vectors, in gene therapy, in study and expression of genes, particularly eukaryotic genes in the context of non-coding and native or near native (or heterologous) regulatory sequences, in shuttling systems, and so forth.

Advantages of MAC- or HAC-based systems over previous vector systems used in therapy are several. Being a fully functional chromosome, there is no theoretical upper size limit to the DNA that can be included in a MAC vector; therefore a large genomic locus with all endogenous (or heterologous, or altered) regulatory elements can be incorporated. MACs are autonomous, their maintenance in the nucleus does not disturb the host genome, and the expression of introduced genes will not be subject to position effects seen with transgenes randomly integrated in the host genome. Unlike current therapies relying on viral vectors, which have the potential to elicit adverse immunological responses, such responses should not arise using a HAC derived solely from human DNA.

Though various methods are provided herein, in one particular embodiment the method for producing a synthetic tandem repeat in the context of an artificial chromosome comprises two steps: i) amplification of monomer (or short multimer) units by rolling circle amplification (RCA) to 1-5 kb DNA fragments, and ii) co-transformation of the fragments into yeast cells along with a vector containing repeat-specific hooks. Further detail with regard to this embodiment, and other embodiments, is provided herein.

VI. Making Long Synthetic Tandem Repeats

It has now been determined that rolling circle amplification can be used to rapidly amplify alphoid and other repeats of a few hundred bp into long repetitive, tandem DNA arrays. Alternatively, in some embodiments relatively short repeat sequence arrays are assembled using in vitro directional ligation (see, e.g., Harrington et al., *Nat. Gen.* 15:345-355, 1997).

Various different types of tandem repeats are contemplated, as are various modified versions of such tandem repeats (for instance, starting monomers that are altered at one or more positions in order to alter or influence an activity of the resultant repeat array). Though various examples are provided herein, tandem repeat sequences are known to those of ordinary skill in the art, as are methods for modifying specific positions or sequences within a monomer or multimers of a repeat sequence. Likewise, the basic methodology of RCA is known. Descriptions provided herein are illustrative of specific example embodiments and are not considered or intended to be limiting.

Repeat Sequences

Alphoid DNA refers to DNA that is present near all known mammalian centromeres. Alphoid DNA is highly repetitive DNA, and it is made up generally of alpha satellite DNA. Alphoid DNA is typically AT rich DNA and also typically contains CENP-B protein binding sites (Barry et al., *Human Molecular Genetics*, 8(2):217-227, 1999; Ikeno et al., *Nature Biotechnology*, 16:431-39, 1998). While the alphoid DNA of each chromosome has common attributes, each chromosomal centromere also has unique features. For example alphoid DNA of the human chromosome 22 consists of two units 2.1 kb and 2.8 kb in length. These units can be identified by EcoRI digestion. In the human Y chromosome alphoid DNA arrays consists off two different size units (2.8 kb and 2.9 kb) that can be identified by SpeI digestion.

The centromere defined as ΔYq74 is the alphoid centromeric region that was isolated from the mini chromosome constructed by Brown et al. (*Human Molec. Gen.*, 3(8): 1227-1237, 1994). This region has a number of attributes, such as inverted repeats and a lack of any consensus CENP-B protein binding sites (see, for instance, US patent publication 2004/0245317).

The chromosome Y centromeric region is made up of two repeating units where each repeating unit is represented by a 2950 bp fragment and a 2847 bp fragment. These fragments that make up the macrostructure of the repeating unit of the chromosome Y alphoid DNA are determined by a SpeI digestion of the isolated alphoid DNA. In the centromeric region each unit is repeated 23 times forming a 140 kb alphoid DNA array. The units are organized as tandem repeats. Each of these fragments itself is made up of a smaller, divergent repeating unit. This repeating unit is about 170 bases long.

The number of repeating units included in a synthetic tandem repeat produced using methods provided herein may vary and may be ultimately dependent on the structure needed for appropriate segregation of the MACs/HACs. The repeating unit may be as small as one of the specific alpha satellite monomers, and in other embodiments, for example, the size may correspond to one of the major SpeI fragments, such as the 2.8 kb or 2.9 kb fragments. These characteristics may be applicable for other alphoid satellite and centromeric regions, and for other sequences found in tandem arrays in the genome and elsewhere, and this is most appropriately determined by the functions of these regions as discussed and recognized.

The macrostructure of the Y chromosome centromeric region is made up of a smaller alpha satellite region that is about 170 base pairs. Specifically, one 2950 bp fragment and one 2847 bp fragment in that order are made up of 34 variants of the about 170 bp alpha satellite region. These alpha satellites are numbered 1-34. The identity of these sequences amongst each other can be determined by tabulating the variations and similarities of the various sequences (see, for instance, SEQ ID NO: 1-34 of U.S. patent publication 2004/024531, each of which sequence is incorporated by reference herein). The variation within the sequences represents the divergence that has taken place within these regions.

The macrostructure defined by the 2847-2950 repeating unit isolated by a SpeI digestion of the isolated ΔYq74 region is the dominant structure that is present. A minor SpeI product is approximately 1800 bases long. The fragment moves as 1.6 kb fragment during electrophoresis; the abnormal mobility of the fragment is explained by the presence of palindromic sequence. This minor 1.6 kb fragment contains specific alpha satellite DNA also, but rather than having the alpha satellites arranged in a tandem array as the major repeating unit does, the minor fragment has six full alpha satellite repeats which are in tandem and three which are inverted repeats. Because this fragment is not detected in normal (non-truncated) chromosome Y, the fragment arose during truncation of the chromosome. It is known that chromosome truncation is often accompanied by rearrangement of the targeted region. These rearrangements occurred near the end of an alphoid DNA array.

CENP-B boxes are specific DNA binding sites for the DNA binding protein, CENP-B (Masumoto et al., *J. Cell Biol.*, 109:1963-1973, 1989). It has been suggested that CENP-B boxes are necessary for de novo kinetochore assembly. However, the chromosome Y centromeric DNA region does not have any CENP-B boxes, suggesting that MACs can be constructed without these DNA binding protein sites. Thus, in some embodiments it is acknowledged that the centromeric region of a MAC may not require, and may not include, a functional CENP-B protein binding site. Such MACs could be constructed by starting with an alphoid array sequence, or other array sequence, that does not have a CENP-B site sequence.

Among other types of repeats are gamma-satellite DNA, major satellite repeat and minor satellite repeats. Gamma-satellite DNA is a 220-bp tandemly arranged repetitive DNA with specificity for the centromeric region of the human X chromosome (Lee et al., *Chromosome Res.* 7(1):43-47, 1999). In the mouse, *Mus musculus domesticus*, two types of repetitive DNA sequences are associated with centromeres. These are the major satellite repeats (6 Mb of 234 bp units) and minor satellite repeats (600 kb of 120 bp units; Choo, *The Centromere*, Oxford University Press, Oxford, UK, 1997). In situ hybridization on metaphase chromosomes has shown that major satellite sequences are located pericentrically, whereas minor satellite sequences coincide with the centric constriction (Wong & Rattner, *Nucleic Acids Res.* 16:11645-11661, 1988; Joseph et al., *Exp. Cell Res.* 183:494-500, 1989).

Short interspersed repetitive sequences, including the human Alus and mouse B1 repeats (Miller & Capy, *Methods Mol Biol.* 260:1-20, 2004) also may be amplified, captured, analyzed, and exploited using methods described herein.

Rolling Circle Amplification

Rolling circle amplification (RCA) is an isothermal process for generating multiple copies of a sequence, which was developed from the rolling circle replication mechanism of microbes. In rolling circle DNA replication in vivo, a DNA polymerase extends a primer on a circular template (Kornberg & Baker, *DNA Replication*, W. H. Freeman, New York, 1991). The product consists of tandemly linked copies of the complementary sequence of the template.

RCA has been adapted for use in vitro for DNA amplification (Fire & Si-Qun Xu, *Proc. Natl. Acad Sci. USA*, 92:4641-4645, 1995; Lui et al., *J. Am. Chem. Soc.*, 118:1587-1594, 1996; Lizardi et al., *Nature Genetics*, 19:225-232, 1998; U.S. Pat. No. 5,714,320). RCA also has been used in a detection method using a probe called a "padlock probe" (International patent publication WO95/22623; Nilsson et al., *Nature Genetics*, 16:252-255, 1997; and Nilsson & Landegren, in *Laboratory Protocols for Mutation Detection*, Landegren, ed., Oxford University Press, Oxford, 1996, pp. 135-138). DNA synthesis has been limited to rates ranging between 50 and 300 nucleotides per second (Lizardi et al., *Nature Genetics*, 19:225-232, 1998; and Lee et al., *Molecular Cell*, 1:1001-1010, 1998). International patent publication WO 2005/003389 describes use of RCA procedures for in vitro amplification of unclonable DNA. See also published U.S. patent document 2003/0207267, and issued U.S. Pat. Nos. 5,854,033; 5,198,543; 5,576,204; and 5,001,050 for additional discussions of RCA techniques.

Optionally, the RCA amplification step can be omitted from the methods provided herein, and short repeat multimers (e.g., a dimer) can be concatermized (concatenated) directly by capture into a TAR vector. Alternatively, relatively short arrays of repeats can be assembled, for instance using directional in vitro ligation reaction. If desired, capture of such relatively short repeat sequences and arrays can be repeated to further lengthen the captured repeat array.

VII. Capture and Concatenation of RCA Repeats

Figure 2A:
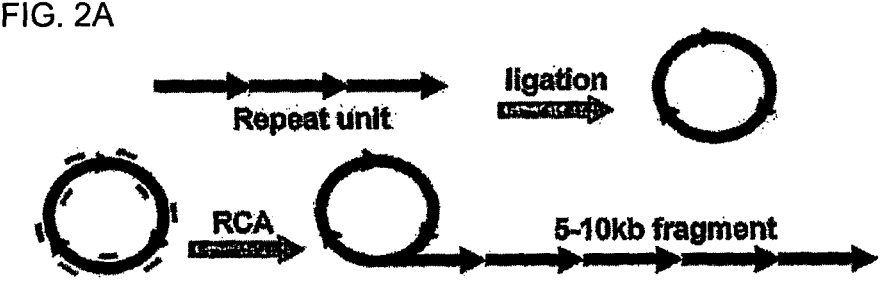
FIGS. 2A and 2B are one example scheme of construction of synthetic tandem arrays.
Figure 2B:
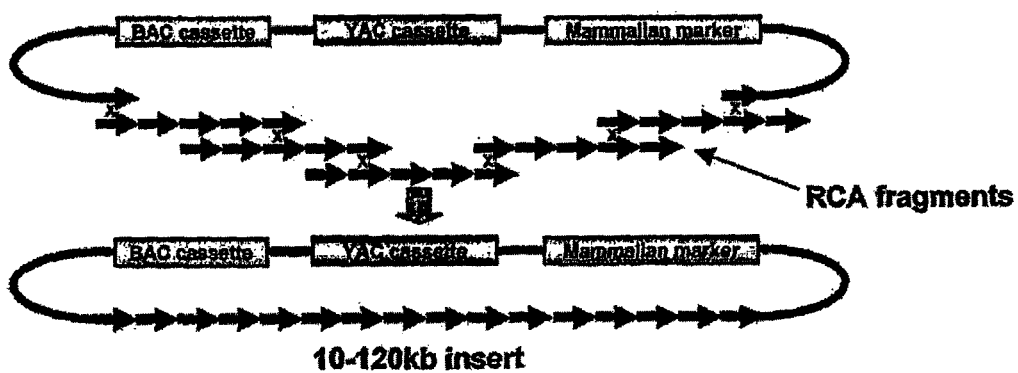

End to end concatenation and recombination of repeat sequences, such as RCA-amplified DNA fragments, accompanied by the interaction of recombined fragments with a TAR vector, results in rescue of large arrays (up to 140 kb) as circular YACs in yeast (see, e.g., FIG. 2B). Optionally, TAR vectors used in methods described herein also contain a BAC replicon; this enables these artificial chromosomes isolates to be transferred into prokaryotic (e.g., *E. coli*) cells.

In some embodiments, 1-5 kb DNA fragments containing synthetic concatamerized repeats (such as those obtained by RCA from a monomer, dimer, or other starting multimer) are co-transformation of the fragments into yeast cells along with a vector containing alphoid-specific hooks (which have at least about 85% identity with the target sequence). End to end recombination of repeat DNA concatamers, followed by the interaction of recombined fragments with the vector, results in a rescue of large arrays (up to 140 kb or more) as circular YACs in yeast.

Optionally, the starting repeat multimer sequence can itself have been obtained from a YAC generated by TAR cloning, for instance, the starting repeat multimer sequence can be a concatamerized synthetic repeat sequence generated in accordance with one of the methods described herein. Effectively, in such an embodiment, the TAR capture of repeat sequences is carried out more than once, for instance at least twice, thereby generating longer final repeat sequences in the resultant artificial chromosome.

TAR cloning exploits a high level of recombination between homologous DNA sequences during transformation in the yeast *Saccharomyces cerevisiae*. Yeast spheroplasts are transformed with a target DNA (e.g., a genome or other sequence or collection or mixture of two or more sequences) along with a TAR cloning vector containing 5' and 3' unique sequences specific to the target sequence. These unique sequences are cloned into, for instance, the polylinker of the TAR vector in such a way that after linearization of the vector between the targeting sequences the unique sequences become recombinogenic with a target sequence during transformation. Recombination between the gene-specific sequences in the vector and the gene-containing genomic fragment leads to the establishment of a circular YAC.

In one illustrative but non-limiting example, the basic TAR cloning vector pVC-ARS is used, which is a derivative of the Bluescript-based yeast-*E. coli* shuttle vector pRS313 (Sikorski and Hieter, *Genetics* 122:19-27, 1989). This plasmid contains a yeast origin of replication (ARSH4) from pRS313. pVC604 has an extensive polylinker consisting of 14 restriction endonuclease 6- and 8-bp recognition sites for flexibility in cloning of particular fragments of interest.

The functional DNA segments of the plasmid are indicated as follows: CEN6 a 196 bp fragment of the yeast centromere VI; HIS3=marker for yeast cells; $Amp_R$=ampicillin-resistance gene. This part of the vector allows it to be cloned and to propagate human DNA inserts as YACs. Construction of a TAR vector for isolation of centromeric regions includes cloning of short specific repeat (for instance, alphoid) DNA sequences (hooks). These hooks are homologous with the sequences at the ends of the target sequence that is to be captured during TAR cloning. For instance, the hooks in some embodiments comprise all or a portion of a repeat sequence such as those described herein. Optionally, the hook homology can be lowered to as low as about 85% identity, to increase recombination efficiency.

To propagate isolated centromeric DNAs in *E. coli* cells a set of retrofitting vectors can be used, similar for instance to those disclosed in U.S. patent publication 2004/0245317. A typical retrofitting vector contains two short (approximately 50 bp each) targeting sequences, A and B, flanking the Co1E1 origin of replication and the $Amp_R$ gene in the pVC604-based TAR cloning vectors (Kouprina et al., *Proc. Natl. Acad. Sci. USA* 95: 4469-4474, 1998). These targeting sequences are separated by a unique BamHI site. Recombination of the vector with a YAC during yeast transformation creates the shuttle vector construct: following the recombination event, the Co1E1 origin of replication in the TAR cloning vector is replaced by a cassette containing the F-factor origin of replication, the chloramphenicol acetyltransferase ($Cm_R$) gene, a mammalian genetic marker and the URA3 of some other yeast selectable marker. The presence of a mammalian marker (such as $Neo_R$ gene or $Hygro_R$ gene or $Bsd_R$ gene) allows for the selection of the construct during transfection into mammalian cells. There are numerous other yeast markers that can be substituted for the specific markers disclosed, and as will be recognized by one of ordinary skill in the art, the functionality of these substitutions can be determined. Some embodiments will incorporate these substitutions as long as they retain the desired property of the various MACs and shuffle vectors disclosed herein.

It is understood that various shuttle vectors have the properties of either shuttling between yeast and mammalian cells, such as human cells, or yeast and bacteria cells, or mammalian cells (e.g., human) and bacteria cells, or between all three different sets of cells. The cloning vectors often are designed so that they can be shuttle vectors as well as cloning vectors. Thus, there are parts of shuttle vectors in general and the disclosed cloning vectors that can be similar or the same. It is specifically contemplated that the shuttle vectors can be engineered such that they do not have the any parts derived from or even necessarily related to the parts of the cloning vectors. Likewise the cloning vectors typically will contain the parts necessary for acting as a shuffle vector. The cloning vectors also can be designed to function only in yeast, for example, and then later retrofitted if desired to function in other systems.

The size of the cloning vector construct can vary, for instance from about 10 kb to 30 kb. The size of the vector construct if it is to be a shuttle between yeast and mammalian cells beneficially would be based on the largest chromosome that can be maintained in the yeast. This is typically around 300 kb. In some embodiments it is less than or equal to about 1 mega base, or 900 kb, or 850 kb, or 800 kb, or 750 kb, or 700 kb, or 650 kb, or 600 kb, or 550 kb, or 500 kb, or 450 kb, or 400 kb, or 350 kb, or 250 kb, or 200 kb, or 150 kb, or 100 kb, or 50 kb.

When the vector is to be shuttled between a bacterial (BAC) and a yeast (YAC) system, or a BAC and a mammalian (MAC) system, the size typically is controlled by the bacterial requirements. This size is typically less than or equal to about 500 kb, 450 kb, or 400 kb, or 350 kb, or 250 kb, or 200 kb, or 150 kb, or 100 kb, or 50 kb.

The cloning vectors should contain a yeast cassette (which itself comprises, e.g., a yeast selectable marker, a yeast origin of replication and a yeast centromere), a bacterial cassette (which itself comprises, e.g., *E. coli* selectable marker, and *E. coli* origin of replication; co1E1 or F-factor) and a mammalian selectable marker. Some additional sequences that simplify construct manipulation can be included (such as rare cutting recognition sites, or lox sites), as well as sequences that would be required for proper replication of MAC in mammalian cells. These vectors can also have recombination sequences such as those discussed herein.

Once formed, an artificial chromosome can be analyzed using art-known techniques, for instance in order to determine or characterize the content of the captured, concatamerized repeat sequence. Confirmation of the repeat structure, while not essential, may be beneficial in order to ensure the fidelity of the cloning process in the hands of an individual. Example techniques for analysis of sequences in artificial chromosomes are described herein, for instance in the Examples below.

VIII. Making MACs Using Long Synthetic Tandem Repeats

Mammalian artificial chromosomes (MACs) are useful, for instance, as alternatives to viral vectors for gene therapy applications, as they allow for the introduction of large payloads of genetic information in a non-integrating, autonomously replicating format. The methods of capturing long synthetic repeat sequence arrays in YACs described herein can be used to generate centromere-like regions that support maintenance (e.g., replication and segregation) of the resultant MAC in a mammalian cell. Those synthetic repeat-based artificial chromosomes used as expression vectors beneficially will also contain one or more convenient sites for incorporating of a gene or other sequence for its expression.

In general, MACs consist of a number of different parts and can range in size. MACs also have a number of properties and characteristics which can be used to describe them. MACs would include for example, artificial chromosomes capable of being placed and maintained in humans, monkeys, apes, chimpanzees, bovines, ovines, ungulates, murines (e.g., mice or rats), as well as other mammals.

The size of the MACs is dictated at least in part by, for example, the size of the components (1) that are required for the MAC to function as a MAC and (2) that are included but not necessarily essential for the MAC to function as a MAC. The size also can be influenced by how the MACs are going to be used, for example whether they will be shuttled between bacterial and/or yeast cells. Typically a MAC will range from about 1 Mb (megabase) to about 10 Mb. They can also range from about 10 kb to about 30 Mb, from 50 kb to about 12 Mb, about 100 kb to about 10 Mb, about 25 kb to about 500 kb, about 50 kb to about 250 kb, about 75 kb to about 200 kb, or about 85 kb to about 150 kb.

Typically if the MACs are going to be shuttled between mammalian and bacterial cells they should be less than 300 kb in size. This type of MAC can also be less than about 750 kb or about 600 kb or about 500 kb or about 400 kb or about 350 kb or about 250 kb or about 200 kb or about 150 kb. If the MACs are going to be shuttled between mammalian and yeast cells they are typically less than 1 mega base in size. This type of MAC can also be less than about 5 mega bases or about 2.5 mega bases or about 1.5 mega bases or about 900 kb or about 800 kb or about 700 kb or about 600 kb or about 500 kb or about 400 kb or about 400 kb or about 200 kb or about 100 kb.

The size of the MACs is described in base pairs, but it is understood that unless otherwise stated, these numbers are not absolutes, but rather represent approximations of the sizes of the MACs. Thus, for each size of the MAC described it is understood that this size could be "about" that size. There is little functional difference between a nucleic acid molecule of 1,500,000 bases and one that is 1,500,342 bases. Those of skill in the art understand that the sizes and ranges are given as direction, but do not necessarily functionally limit the MACs.

MACs can take a variety of forms. The form of a MAC refers to the shape of the artificial chromosome. For instance, MACs can be linear. A linear MAC is an artificial chromosome that has the form or shape of a natural chromosome. This type of MAC has "ends" to the chromosome, much like most naturally occurring chromosomes. Linear MACs it must have telomeres. Telomeres are specialized purine rich sequences that are thought to protect the ends of a chromosome during replication, segregation, and mitosis. Telomere sequences and uses are well known in the art.

MACs can also be circular. There is no terminus to a circular MAC. When a MAC is circular, it does not need telomere sequence because there is no end of the chromosome that must be protected during replication, segregation, and mitosis. A circular MAC optionally may contain telomere sequence so that if it is linearized it can function as a linear MAC, but telomere sequence is not required for the circular MAC to function.

The content of a MAC can vary. The content can be characterized, for instance, by sequence, component parts, size, and function. The content can be influenced by a number of things, for example, the form that the MAC will take, whether the MAC is going to be shuttled between bacterial and/or yeast cells, and the type of mammalian cell into which the MAC will be introduced. In general, a circular MAC will include an origin of replication, a centromeric sequence or region, and one or more other components as discussed herein or known to one of ordinary skill in the art. Optionally, the origin of replication and centromeric function are contained in the alphoid sequences contained in the MACs.

Centromeric Region

The centromeric region of the MAC (also referred to herein more specifically as an engineered centromeric region, in light of the systems provided for making synthetic repeat arrays) can be discussed in the context of the function(s) that it performs. One such function is related to the appropriate segregation of the MAC of which it is a part during mitosis. Proper segregation is a main function of the centromere. This segregation results in a maintenance of MAC as an extra-chromosomal element in a single copy number in transfected cells. Formation of MACs can be detected by FISH (as an additional chromosome on the metaphase plate) or by immunofluorescence using kinetochore-specific antibodies, for instance, both of which are demonstrated herein. Alternatively, MAC sequences can be rescued by E. coli (or another prokaryote) or yeast transformation; this is facilitated if the MAC contains BAC and/or YAC cassettes.

The main function of the centromeric region of the described MACs is to provide a centromere-like activity to the MACs, which means that the MACs are replicated and segregated by a cell to which they are provided. Also encompassed, however, are embodiments where the centromeric region also functions, or contains a sequence that functions, as an origin of replication. By way of example, it has been demonstrated that alphoid regions, such as the alphoid regions isolated from the X chromosome and chromosome 21, can function in a MAC without a separate origin of replication, or in other words can function as an origin of replication in mammalian cells.

The centromeric region of the MACs and HACs provided herein comprises a long synthetic tandem repeat sequence prepared in accordance with a described method. A representative method includes RCA amplification of repeat sequence(s) into a concatenated repeat or array of repeat sequences, followed by TAR capture of one or more of the concatenated repeats into an artificial chromosome.

Optionally, the centromeric region of the described HACs functions as a regulated or conditional centromere. Regulated (conditional) centromere sequences include a sequence (or set of sequences, or array of sequences) that permits and enables altering the function of the centromere, e.g., experimentally or through the application of a compound or drug or other influence. One example of a sequence that makes a centromeric region "regulatable" or "conditional" is the tetracycline operator (tetO) sequence; the function of a tetO-containing centromeric region can be altered expression/repression of protein(s) that are capable of binding to the tetO sequence (and, in provided examples, inactivation of centromeric function that can be detected as measurable loss of the artificial chromosome containing the regulated centromere). Thus more generally, any sequence that is known to bind a protein may be included in the centromeric region sequence in order to convey the ability to regulate function of that centromere. This principle, and systems for use with it, is discussed more fully herein.

Telomeres

Optionally, a MAC can comprise one or more telomere regions. Telomeres are regions of DNA which help prevent the unwanted degradation of the termini of chromosomes. The telomere is a highly repetitive sequence that varies from organism to organism. For example, in mammals the most frequent telomere sequence repeat is $(TTAGGG)_n$, and the repeat structures can be from for example 2-20 kb. The following patents provide representative discussions of telomeres, telomerase and methods and reagents related to telomeres: U.S. Pat. Nos. 6,093,809, 6,007,989, 5,695,932, 5,645,986, and 4,283,500.

Origins of Replication

Origins of replication are regions of DNA from which DNA replication during the S phase of the cell cycle is primed. While yeast origins of replication, termed autonomously replicating sequence (ARS), are fully defined (Theis et al., Proc. Natl. Acad Sci. USA 94: 10786-10791, 1997), there does not appear to be a specific corresponding origin of replication sequence in mammalian DNA (Grimes and Cooke, Human Molecular Genetics, 7(10): 1635-1640, 1998). There are, however, numerous regions of mammalian DNA that can function as origins of replication (Schlessinger and Nagaraja, Ann. Med., 30:186-191, 1998; Dobbs et al., Nucleic Acids Res. 22:2479-89, 1994; and Aguinaga et al., Genomics 5:605-11, 1989). It is known that for every 100 kb of mammalian DNA sequence there is a sequence that will support replication, but in practice sequences as short as 20 kb can support replication on episomal vectors (Calos, Trends Genet. 12:463-466, 1996). This indicates that epigenetic mechanisms, such as CpG methylation patterning likely play some role in replication of DNA (Rein et al., Mol. Cell. Biol. 17:416-426, 1997).

The origin of replication of a disclosed MAC can be any size that supports replication of the MAC. One way of ensuring that the MAC has a functional ori sequence is to require that MAC contain at least 5 kb of mammalian genomic DNA. In other embodiments, it contains at least 10 kb, 15 kb, 20 kb, 25 kb, 30 kb, 35 kb, 40 kb, 45 kb, 50 kb, 60 kb, 70 kb, 80 kb, 90 kb, or 100 kb of mammalian genomic DNA. In general any region of mammalian DNA could be used as origin of replication. If there is replication of the MAC, the origin of replication is functioning as desired.

The origin of replication of the MAC can be obtained from any number of sources, including particularly any number of sources of mammalian DNA. By way of example, it can be any region of mammalian DNA that is not based on a repeat sequence, such as the alphoid DNA sequence.

A native alphoid DNA sequence does not contain an origin of replication in it, because the repeat sequences are so small, for example about 170 base pairs, and can be repeated many times, so that there is not enough variation for an origin of replication sequences to be present. However, in many instances these regions, when they contain multiple alphoid DNA repeats, can function as origins of replication in mammalian, such as human, cells (see, e.g., U.S. patent publication No. 2004/0245317). Also all HACs described so far are stable in human cells and therefore they contain an origin of replication.

Also included in MACs as described herein is a centromere region. It is understood that a centromere region, broadly defines a functional stretch of nucleic acid that allows for segregation of the MAC during the cell cycle and during mitosis. Although known sequences exist that can be used as a centromere region in a MAC, new methods for generating centromere regions are provided herein.

Markers

MACs can include nucleic acid sequence encoding a marker product. This marker product is used to determine if the MAC has been delivered to the cell and, once delivered, is being expressed. Non-limiting examples of marker genes include the *E. coli* lacZ gene which encodes beta-galactosidase, and green fluorescent protein.

In some embodiments the marker may be a selectable marker. Examples of contemplated selectable markers for mammalian cells are dihydrofolate reductase (DHFR), thymidine kinase (TK), neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are CHO DBFR—cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern & Berg, *J. Molec. Appl. Genet.* 1: 327, 1982), mycophenolic acid (Mulligan & Berg, *Science* 209: 1422, 1980), or hygromycin (Sugden et al., *Mol. Cell. Biol.* 5: 410-413, 1985). These three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

The use of markers can be tailored for the type of cell that the MAC is in and for the type of organism the cell is in. For example, if the MAC is to be a MAC that can shuffle between bacterial and yeast cells as well as mammalian cells, it may be desirable to engineer a different markers specific for the bacterial cell, for the yeast cell, and for the mammalian cell. Those of ordinary skill in the art, given the disclosed MACs, are capable of selecting and using appropriate marker(s) for a given set of conditions or a given set of cellular requirements.

Markers also can be useful in tracking a MAC through cell types and to determine if the MAC is present and functional in different cell types. The markers can also be useful in tracking any changes that may take place in the MACs of over time or over a number of cell cycle generations.

Transgenes

The transgenes that can be placed into the disclosed MACs can encode a variety of different types of molecules. By way of non-limiting examples, these transgenes can encode genes which will be expressed and thereby produce a protein product, or they can encode an RNA molecule that when it is expressed will encode functional nucleic acid, such as a ribozyme or small inhibitory RNA (or set thereof.

Functional nucleic acids are nucleic acid molecules that have a (or more than one) specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with a target mRNA of the host cell or a target genomic DNA of the host cell or a target polypeptide of the host cell. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($k_d$) less than $10^{-6}$, in some embodiments it will bind with a $k_d$ less than $10^{-8}$, a $k_d$ less than $10^{-10}$, or even a $k_d$ less than $10^{-12}$. A representative sample of methods and techniques that aid in the design and use of antisense molecules can be found in the following non-limiting list of patents: U.S. Pat. Nos. 5,135,917, 5,294,533, 5,627,158, 5,641,754, 5,691,317, 5,780,607, 5,786,138, 5,849,903, 5,856,103, 5,919,772, 5,955,590, 5,990,088, 5,994,320, 5,998,602, 6,005,095, 6,007,995, 6,013,522, 6,017,898, 6,018,042, 6,025,198, 6,033,910, 6,040,296, 6,046,004, 6,046,319, and 6,057,437.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Aptamers can bind very tightly, with $k_d$s from the target molecule of less than $10^{-12}$, or less than $10^{-6}$, less than $10^{-8}$, less than $10^{-10}$, or even less than $10^{-12}$.

Aptamers can bind the target molecule with a very high degree of specificity. For example, aptamers have been isolated that have greater than a 10000 fold difference in binding affinities between the target molecule and another molecule that differ at only a single position on the molecule (U.S. Pat. No. 5,543,293). Thus, in various embodiments, the aptamer has a $k_d$ with the target molecule at least 10 fold lower than the $k_d$ with a background binding molecule, or at least 100 fold lower, at least 1000 fold lower, or at least 10000 fold lower than the $k_d$ with a background binding molecule. It is preferred when doing the comparison for a polypeptide for example, that the background molecule be a different polypeptide. Representative examples of how to make and use aptamers to bind a variety of different target molecules can be found in the following non-limiting list of patents: U.S. Pat. Nos. 5,476,766, 5,503,978, 5,631,146, 5,731,424, 5,780,228, 5,192,613, 5,795,721, 5,846,713, 5,858,660, 5,861,254, 5,864,026, 5,869,641, 5,958,691, 6,001,988, 6,011,020, 6,013,443, 6,020,130, 6,028,186, 6,030,776, and 6,051,698.

Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes (for example, but not limited to the following: U.S. Pat. Nos. 5,334,711, 5,436,330, 5,616,466, 5,633,133, 5,646,020, 5,652,094, 5,712,384, 5,770,715, 5,856,463, 5,861,288, 5,891,683, 5,891,684, 5,985,621, 5,989,908, 5,998,193, 5,998,203, and international patent publications WO 9858058, WO 9858057, and WO 9718312) hairpin ribozymes (for example, but not limited to the following: U.S. Pat. Nos. 5,631,115, 5,646,031, 5,683,902, 5,712,384, 5,856,188, 5,866,701, 5,869,339, and 6,022,962), and tetrahymena ribozymes (for example, but not limited to the following: U.S. Pat. Nos. 5,595,873 and 5,652,107). There are also a number of ribozymes that are not found in natural systems, but which have been engineered to catalyze specific reactions de novo (for example, but not limited to the following: U.S. Pat. Nos. 5,580,967, 5,688,670, 5,807,718, and 5,910,408).

Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Representative examples of how to make and use ribozymes to catalyze a variety of different reactions can be found in the following non-limiting list of patents: U.S. Pat. Nos. 5,646,042, 5,693,535, 5,731,295, 5,811,300, 5,837,855, 5,869,253, 5,877,021, 5,877,022, 5,972,699, 5,972,704, 5,989,906, and 6,017,756.

Triplex forming functional nucleic acid molecules are molecules that can interact with either double-stranded or single-stranded nucleic acid. When triplex molecules interact with a target region, a structure called a triplex is formed, in which three strands of DNA form a complex dependant on both Watson-Crick and Hoogsteen base-pairing. Triplex molecules can bind target regions with high affinity and specificity. For instance, in some embodiments the triplex forming molecules bind the target molecule with a $k_d$ less than $10^{-6}$, less than $10^{-8}$, less than $10^{-10}$, or even less than $10^{-12}$. Representative examples of how to make and use triplex forming molecules to bind a variety of different target molecules can be found in the following non-limiting list of patents: U.S. Pat. Nos. 5,176,996, 5,645,985, 5,650,316, 5,683,874, 5,693,773, 5,834,185, 5,869,246, 5,874,566, and 5,962,426.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. Refer for instance to WO 92/03566 and Forster and Altman (*Science* 238:407-409, 1990).

Similarly, eukaryotic EGS/RNAse P-directed cleavage of RNA can be utilized to cleave desired targets within eukaryotic cells (Yuan et al., *Proc. Natl. Acad. Sci. USA* 89:8006-8010, 1992; WO 93/22434; WO 95/24489; Yuan and Altman, EMBO J. 14:159-168, 1995; and Carrara et al., *Proc. Natl. Acad. Sci. USA* 92:2627-2631, 1995). Representative examples of how to make and use EGS molecules to facilitate cleavage of a variety of different target molecules are found in the following non-limiting list of patents: U.S. Pat. Nos. 5,168,053, 5,624,824, 5,683,873, 5,728,521, 5,869,248, and 5,877,162.

The transgenes can also encode proteins. These proteins can be native to the organism or cell type, or they can be exogenous. In one example, if the transgene encodes a protein, it may be protein related to a certain disease state, wherein the protein is under-produced or is non-functional when produced from the native gene. In this situation, the protein encoded by the MAC is meant as a replacement protein. In other situations, the protein may be non-natural, meaning that it is not typically expressed in the cell type or organism in which the MAC is found. An example of this type of situation may be a protein or small peptide that acts as mimic or inhibitor or inhibitor of a target molecule which is unregulated in the cell or organism possessing the MAC.

Merely by way of example, the following is a list of full-length human genes (and their approximate size); each of the listed genes has been linked to at least one disease, and complete encoding sequence has been isolated from the human genome by TAR: HPRT (60 kb*), BRCA1 (84 kb*), BRCA2 (90 kb), hTERT (60 kb*), KAI1 (200 kb*), TEY1 (70 kb*), SCK (150 kb), ASPM (70 kb), ATM (200 kb), SPANX-C (83 kb), CMT2D (120 kb), NBS1 (64 kb), SPANX-C (70 kb), PEG3 (280 kb), and MUC2 (50 kb). These are representative, non-limiting examples of genes which could beneficially be expressed as transgenes from MACs and HACs produced as described herein. Functional expression has been demonstrated at least for those sequences indicated with an asterisk (*).

Control Sequences

The transgenes, or other sequences, in the MACs can contain or be associated with promoters, and/or enhancers to help control the expression of the desired gene product or sequence. A promoter is generally a sequence or sequences of DNA that function when in a relatively fixed location in regard to the transcription start site. A promoter contains core elements required for basic interaction of RNA polymerase and transcription factors, and may contain upstream elements and response elements.

Specific example promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g., beta actin promoter. The early and late promoters of the SV40 virus are conveniently obtained as an SV40 restriction fragment that also contains the SV40 viral origin of replication (Fiers et al., Nature, 273: 113, 1978). The immediate early promoter of the human cytomegalovirus is conveniently obtained as a HindIII E restriction fragment (Greenway et al., Gene 18: 355-360, 1982). Promoters from the host cell or related species also are useful herein.

The term "enhancer" generally refers to a sequence of DNA that functions at no fixed distance from the transcription start site and can be either 5' (Laimins et al., Proc. Natl. Acad. Sc. 78: 993, 1981) or 3' (Lusky et al., Mol. Cell Bio. 3: 1108, 1983) to the transcription unit. Furthermore, enhancers can be within an intron (Banerji et al., Cell 33: 729, 1983) as well as within the coding sequence itself (Osborne et al., Mol. Cell Bio. 4: 1293, 1984). They are usually between 10 and 300 bp in length, and they function in cis (rather than trans). Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, α-fetoprotein and insulin), typically one will use an enhancer from a eukaryotic cell virus. Specific examples are the SV40 enhancer on the late side of the replication origin (bp 100-270), the cytomegalovirus early promoter enhancer, the polyoma enhancer on the late side of the replication origin, and adenovirus enhancers.

The promoter and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

The promoter and/or enhancer region may act as a constitutive promoter and/or enhancer to maximize expression of the region of the transcription unit to be transcribed. In some embodiments, the promoter and/or enhancer region is active in all eukaryotic cell types. One examples of a promoter of this type is the CMV promoter (650 bases). Other constitutive promoters are SV40 promoters, cytomegaloviris (full length promoter), and retroviral vector LTF.

It has been shown that specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or more generally nucleated cells) may also contain sequences necessary for the termination of transcription which may affect mRNA expression. These regions are transcribed as polyadenylated segments in the untranslated portion of the mRNA encoding tissue factor protein. The 3' untranslated regions can also include one or more transcription termination sites. In some embodiments, the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In one embodiment of the transcription unit, the polyadenylation region is derived from the SV40 early polyadenylation signal and consists of about 400 bases. It is also preferred that the transcribed units contain other standard sequences alone or in combination with the above sequences improve expression from, or stability of, the construct.

One beneficial property that can optionally be engineered into a MAC, including the disclosed MACs, is the ability to be shuttled back and forth between mammalian, bacterial, and yeast cells. The MACs that have this property will have specialized structural features that, for example, allow for replication in two or all three types of cells. For example, DNA sequence that has origins of replication sufficient to promote replication in mammalian cells will typically not support replication in yeast cells. Yeast cells typically require ARS sequences for replication. It is thus beneficial to include known or cryptic ARS sequences in the disclosed MACs, for instance cryptic ARS sequences present within an alphoid DNA array (see, e.g., U.S. patent publication 2004/0245317). The ability to shuttle between these three different organisms allows for a broad range of recombinant biology manipulations that would not be present or as easily realized if the MACs only functioned in mammalian cells. For example, homologous recombination techniques, available in yeast, but not typically available in mammalian cells, can be performed on a MAC that can be shuffled back and forth between a yeast cell and a mammalian cell. Examples of such a beneficial advantage are described herein, for instance with regard to generating a long synthetic centromeric tandem repeat and inserting it into a MAC using transformation associated recombination in yeast. In addition, alphoid DNA arrays can be modified by homologous recombination in yeast to study centromere functions. Moreover, a transgene cloned in a MAC can be mutated by homologous recombination in yeast, for instance to study or alter a gene expression.

A circular MAC construct can be engineered from a linear MAC by circularization. Such circularization can be carried out, for instance, by homologous recombination in yeast similar to what has been done for linear YACs (Cocchia et al. Nucl. Acids Res. 28:E81, 2000). Alternatively, circularization could be induced using Lex-Cre site-specific recombination system (Qin et al., Nucl. Acids Res. 23: 1923-1927, 1995.)

Artificial chromosomes produced using methods described herein are stable, in that they are not lost from all cells at the time of cell division (with the exception of, in some instances, the described regulated/conditional artificial chromosomes). Rather, they segregate correction in the absence of selection and are thereby maintained in a cell or cell population over time. In various embodiments, they are maintained in a cell or cell population for at least one cell division, at least two, at least five, at least 10, at least 20, at least 50 cell divisions or more. By maintained at a cell divisions, it is understood that not every single cell in a population is required to contain one of the artificial chromosomes, though usually the majority of the cells will contain a low copy number, for instance preferably one of the artificial chromosomes. In some instances, however, at any instance or after a selected number of cell divisions/generations, at least about 25% of the cells in a population will contain at least one copy of the artificial chromosome. More preferably, at least about 30%, 40%, 50% or more of the cells will contain at least one copy, for instance, at least about 60%, 70%, 75%, 80% or even more. In particular embodiments, about 85%, 90%, 95%, or even 98% of the cells in a population, or more, will contain at least one (and preferably only one) copy of the artificial chromosome. By way of example, the presence and/or number of MACs in a cell (or population of cells) can be detected, determined and/or monitored using standard techniques, such as in situ hybridization (e.g., FISH) or other art known techniques.

Another beneficial property of MACs smaller than 500 kb is their ability to maintain size and structure when being shuttled between bacterial, yeast, and mammalian cells. This property is due in part to divergence that can exist in the alpha satellite regions of the centromeric region of the MAC. In certain constructs, the greater the internal homology, the greater the chance that homologous recombination events can arise in, for example, the host yeast cell. Especially in yeast and bacteria, the more divergent the sequences, the more stable the MAC will be. Thus, variation between the alpha satellites (or other repeat sequences) that make up the centromeric region of the MAC is a desirable feature in some embodiments. Variation may be at the level of 2%, 5%, 10%, or more, for instance as high as 15%, 20%, 25%, or even higher.

As discussed the disclosed MACs can optionally carry a one or more of a variety of transgenes; representative and non-limiting examples are discussed herein. These transgenes can perform a variety of functions, including but not limited to, the delivery of some type of pharmaceutical product, the delivery of some type of tool which can be used for the study of cellular function or the cell cycle, and so forth.

As with other transgene delivery systems, one of ordinary skill in the art will understand methods to determine and measure the efficiency with which a particular artificial chromosome is introduced into a target cell, the level at which it is maintained throughout time or numbers of doublings, and the level, location, and other characteristics of expression from any transgene(s) carried on it. Example methods for making such determinations are described herein, but are not intended to be limiting.

IX. Uses of MACs Having Long Synthetic Tandem Repeats

The disclosed MACs can further be characterized by their function. MACs beneficially should be able to both replicate and segregate normally during a cell cycle; in other words, a MAC should be mitotically stable. In some embodiments, a MAC will be maintained in a single copy number in a transfectant cell. In most embodiments, there is minimal, or preferably no, inhibition of expression of genes cloned in MAC. One element of the stability of the provided MACs is that they do not tend to integrate into mammalian chromosomes. Optionally, MACs can have a number of other functional properties.

The ability to co-amplify other DNA sequences along with repeat (e.g., alphoid) DNA during RCA will have a profound effect on our understanding of organization of a human centromeric region and a kinetochore function. For instance, alphoid DNA monomer can be co-amplified along with a tet operator (tetO) sequence (see, e.g., Tovar et al., *Mol. Gen. Genet.* 215 (1):76-80, 1988). Such a hybrid synthetic array is competent in HAC formation. The tet operator sequence can be used as a "hook" or "handle" for re-isolating the HAC from cells, as well as a target for destabilizing protein binding in embodiments that relate to regulated (conditional) centromeres and chromosomes).

By way of example, HACs generated from such synthetic DNA arrays can be used for studying the organization of a functional kinetochore and regulation of HAC copy number in mammalian cells, similar to that previously described for yeast artificial chromosomes (Chlebowicz-Sledziewska & Sledziewski, *Gene.* 39:25-31, 1985).

Analysis of Sequences that Support Centromere/Kinetochore Formation

Synthetically produced and manipulable Mammalian Artificial Chromosomes, including HACs, provide a unique opportunity to study kinetochore formation and to develop a new generation of vectors with a potential in gene therapy. An investigation into the structure/function relationship in centromeric tandem repeats in HACs requires the ability to manipulate repeat substructure efficiently.

Mutagenized arrays generated by RCA-TAR will be used to investigate how DNA divergence in a monomer, length of a monomer, and AT content affect the efficiency of HAC formation. In addition, role of CpG methylation within alphoid DNA in centromere chromatin assembly and HAC formation can be investigated using the methods and compositions described herein.

MACs as Expression Vectors

The MACs can include other sequences, for instance sequences that are not essential merely for the maintenance of the MAC in a cell. For instance, in some situations a MAC is acting much like a vector, in that it can be a vehicle for delivery and expression of exogenous DNA in a cell. MACs are beneficially used as expression vectors because they are stably replicated and propagated with the dividing cell. Thus there are a number of additions that optionally can be included in a MAC that can provide a new use for the MAC or aid in the use of the MAC, or both. A few non-limiting examples of these types of additions are marker regions, transgenes, and tracking motifs.

X. Conditional (or Regulatable) Centromeres and Chromosomes

The first conditional centromere was described by Hill and Bloom in the budding yeast (Hill & Bloom, *Prog Clin Biol Res.* 313:149-158, 1989; Hill & Bloom, *Mol Cell Biol.* 7:2397-40, 1987). That conditional centromere was constructed by orienting a conditional promoter so that when active, it would transcribe through the centromere, inactivating it. This approach was practical for the tiny (125 bp) yeast centromere, but not for human centromeres, which can be several million base pairs across.

A representative conditional centromere made and described herein is regulated by adjusting the chromatin at the centromere. In the first instance, this centromere can be turned off by expressing in cells a protein such as the tetracycline transactivator (tTA—Gossen & Bujard, *Proc. Nat. Acad. Sci. (USA)* 89, 5547-5551, 1992). This recruits the transcriptional machinery and is believed to inactivate the centromere by recruiting proteins that alter the chromatin such that it is no longer compatible with centromere function. Because any protein can in principle be fused to the tetracycline repressor and therefore targeted to the centromere, it is believed to be possible to identify proteins the targeting of which will make the centromere work better (e.g., stabilize the centromere and therefore the artificial chromosome), in addition to those the targeting of which inactivates (or reduces the function of) the centromere. If, for example, a minichromosome was engineered so that it expressed a protein whose binding to the centromere inactivated it (tTA is one example), then MACs could be made by growing cells (or potentially animal or human subjects) in the presence of tetracycline. This would allow the MAC to be stable, as the centromere would be functional. At any desired time, however, if tetracycline were removed from the nutrients, then the tTA would bind to the centromere and the chromosome would be lost. This would allow the MAC to function during a particular developmental window, and then be eliminated later from dividing cells.

Described below (in Example 3) is the construction and characterization of a HAC using artificially designed alphoid DNA that includes a tetO sequence. The formation efficiency of the tetO alphoid based construct was somewhat decreased as compared with controls, but the tetO alphoid HACs were stably maintained in host cells, indicating that tetO sequence does not effect a proper HAC segregation during mitotic divisions. On the formed HACs, the tetO sequence did not inhibit or undermine stability of the HAC. Despite the inclusion of tetO sequence, the resultant HAC was functional for formation of chromatin structures. Notably, tetO alphoid DNA repeat had an ability to form these chromatin structures autonomously.

Evidence described herein clearly demonstrates that tetR binds to the tetO sequence included in an engineered HAC. Because it exhibits accurate tetR binding, tetO alphoid HAC is useful for assays and systems that employ tetR-fusion proteins. tetR-VP16 binding to the tetO dimer HAC drastically decreased HAC stability. Thus, HAC destabilization (and subsequent lost) can be intentionally induced by the induction of open chromatin formation, without any change of DNA sequence. This is the first example of changing the function of a centromere, and thereby the stability of a chromosome, in higher eukaryote without any drug or toxic materials treatment affecting cell viability. This indicates the tetO alphoid HACs are useful as marker chromosomes that exhibit conditional chromosome stability.

Other engineered DNA binding protein specific sequence-based DNA sequences can be used in regulatable centromere sequences as contemplated herein. For instance, Tonaitti et al. (*Gene Therapy* 11:649-657, 2004) describe transcription regulatory systems that are engineered to provide fine modulation of gene expression. These include Tet-ON systems, which could readily be adapted for use in conditional centromeres and chromosomes. See also, the tetracycline responsive regulatory systems described in Baron & Bujard (*Meth. Enz.* 327,401-421, 2000) and references cited therein.

XI. Representative Uses of Artificial Chromosomes with a Conditional/Regulatable Centromere With the provision herein of mammalian artificial chromosomes having a regulated (conditional) centromere sequence, methods of their use are now enabled. The following provides example utilities.

Conditional artificial chromosomes can be used to study of functional organization of a mammalian centromere. They provide the opportunity to target a tetO HAC by different tetR protein fusions, which enables determining and measuring their effect on HAC segregation. The interspersed CENP-A chromatin clusters and modified histone H3 clusters have been found within a functional centromere domain. Targeting of a tetO HAC by different tetR protein fusions would allow investigation of the relations between such epigenetic chromatin assemblies and the centromere functions.

Conditional artificial chromosomes can also be used to study structural requirements for de novo HAC formation. The described example tetO HAC (a representative conditional artificial chromosome) was developed using a sequence unit containing only one complete 170 bp alphoid DNA monomer. By changing one or more nucleotides within the original monomer (e.g., by mutational analysis), then using the modified (mutated) sequence to generate a HAC (e.g. through amplification using the described TAR-RCA method), the alphoid DNA sequence can be analyzed to determine which nucleotides are critical for de novo HAC formation, as well as which influence and can be used to fine-tune this function.

Conditional artificial chromosomes can also be used in a system to register chromosome non-disjunction in mammalian cells. tetO HAC can be visualized using a fusion of GFP (or another label) attached to the TetR protein, which provides a simple assay for detection of HAC loss and HAC gain. This system is suitable for screening conditions that induce (or prevent) aneuploidy, including screening compounds for their influence on aneuploidy. This constitutes an important system that can be used as a drug control (test) in pharmacology. It is believed that, prior to this disclosure, there was no approach for this purpose described in human cells.

Conditional artificial chromosomes can also be used for regulated gene expression in mammalian cells. HACs represent a very promising system for regulated gene expression in mammalian cells. Any full-size gene can be targeted into an established HAC by site-specific recombination (for instance, using the LoxP-Cre system). There are at least two advantages of using conditional (e.g., tetO containing) HACs for this purpose: i) tetO HAC with the targeted gene can be easily detected after transfection; and ii) HAC loss may be easily induced by kinetochore inactivation. The ability to induce such loss is particularly useful to confirm that an observed phenotype is caused by expression of the transgene on the HAC (or MAC, depending on the circumstance). A similar approach involving a conditional centromere has been widely used in budding yeast.

Conditional artificial chromosomes can also be used to assist in transferring HACs into different host cells. The ability to visualize a conditional HAC using GFP greatly simplifies HAC transfer from one cell line to another cell line. This can be beneficial because different genotypes or phenotypes may impact or alter kinetochore function. Moving HACs to different cell lines can also be used to study regulation of gene expression within the HAC. It is also important to be able to mobilize a HAC carrying a disease-associated gene into a set of target cells obtained from different patients during gene therapy.

Because conditional HAC loss can be monitored with a GFP fusion (e.g., a GFT-TetR fusion), the conditional HAC system allows analysis of genetic control for proper chromosome segregation, similar to that in budding yeast. For example, extragenic suppressors can be identified, that prevent HAC destabilization after targeting by the VP16 cassette.

Centromeric chromatin containing multiple tetO sequences within HAC can be selectively purified using Tet-R column. The isolated protein spectrum may be analyzed both from interphase and metaphase chromosomes for instance, in order to characterize protein content of the associated kinetochore.

The systems and constructs described herein are also useful for studying and influencing epigenetic control of human centromere/kinetochore. Because the described tetO alphoid DNA array is competent in HAC formation, clones with chromosomal integrations of this array are a useful to investigate re-activation of a "silent centromere" in the chromosomes. Analysis of re-activation (e.g., involving targeting of centromere-specific proteins into the integration site) may benefit from the use of tetO sequences that allow simple HAC detection.

The example conditional MAC (or HAC) system based on a tetO sequence can be further manipulated by exposing cells bearing the tetO HAC to tetracycline, which blocks binding of a tTA protein to its target sequence on the HAC. If the tTA was expressed in cells bearing the tetO conditional artificial chromosome, but the cells were then grown in the presence of tetracycline, the HAC will remain stable (and therefore maintained). This can be used as the basis for a system where cells or organisms contain the conditional artificial chromosome for a desired period, for example, during embryonic or some other phase of development, but then later the cells or organisms are induced to lose the conditional HAC. For instance, including tetracycline in the nutrient supply would prevent the tTA from binding to the HAC; then removal of the tetracycline would allow the tTA to bind to the HAC and destabilize it, leading to loss.

XII. Delivery of the Compositions to Cells

Methods are known for the introduction of the BAC/YACs into mammalian cells, including for instance electroporation, lipofection and calcium phosphate precipitation. The compositions also can be delivered through a variety of nucleic acid delivery systems, direct transfer of genetic material, in but not limited to, plasmids, viral vectors, viral nucleic acids, phage nucleic acids, phages, cosmids, or via transfer of genetic material in cells or carriers such as cationic liposomes. Such methods are well known in the art and readily adaptable for use with the MACSs described herein. In certain cases, the methods will be modified to specifically function with large DNA molecules. Further, these methods can be used to target certain diseases and cell populations by using the targeting characteristics of the carrier or delivery system.

Transfer vectors can be any nucleotide construction used to deliver genes into cells (e.g., a plasmid), or as part of a general strategy to deliver genes, e.g., as part of recombinant retrovirus or adenovirus (Ram et al. *Cancer Res.* 53:83-88, 1993). Appropriate means for transfection, including viral vectors, chemical transfectants, or physico-mechanical methods such as electroporation and direct diffusion of DNA, are described by, for example, Wolff et al. (*Science,* 247, 1465-1468, 1990) and Wolff (*Nature,* 352:815-818, 1991).

As used herein, plasmid or viral vectors are agents that transport a MAC into a target cell without significant degradation and include a promoter yielding expression of a gene or other payload in the cells into which it is delivered. In some embodiments the MACs are derived from either a virus or a retrovirus. Viral vectors are Adenovirus, Adeno-associated virus, Herpes virus, Vaccinia virus, Polio virus, AIDS virus, neuronal trophic virus, Sindbis and other RNA viruses, including these viruses with the HIV backbone. Also contemplated are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, for instance, a transgene or marker gene, than other viral vectors. For these reason, retroviral vectors are a commonly used type of vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A particular embodiment is a viral vector which has been engineered so as to suppress the immune response of the host organism, elicited by the viral antigens. Optionally, vectors of this type will carry coding regions for Interleukin 8 or 10.

The disclosed compositions can be delivered to target cells in a variety of ways. For example, the compositions can be delivered through electroporation, lipofection, or calcium phosphate precipitation. The delivery mechanism chosen will depend in part on the type of cell targeted and whether the delivery is occurring for example in vivo or in vitro. For example, a contemplated mode of delivery for in vivo use would be the use of liposomes. Lipofection can be used, for instance, to yield as many as $5 \times 10^{-5}$ neomycin-resistant transfectants per microgram of BAC/YAC DNA.

Provided compositions can comprise for example, in addition to the disclosed MACs or vectors, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al., *Am. J. Resp. Cell. Mol. Biol.* 1:95-100, 1989; Felgner et al., *Proc. Natl. Acad. Sci USA* 84:7413-7417, 1987; and U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

The compositions can be administered in a pharmaceutically acceptable carrier and can be delivered to the subject's cells in vivo and/or ex vivo by a variety of mechanisms well known to those of ordinary skill in the art (e.g., uptake of naked DNA, liposome fusion, intramuscular injection of DNA via a gene gun, endocytosis and the like). If ex vivo methods are employed, cells or tissues can be removed and maintained outside the body according to standard protocols well known to those of ordinary skill in the art. The compositions can be introduced into the cells via any gene transfer mechanism, such as, for example, calcium phosphate mediated gene delivery, electroporation, microinjection or proteoliposomes. The transduced cells then can be infused (e.g., in a pharmaceutically acceptable carrier) or homotopically transplanted back into the subject using standard methods for the cell or tissue type. Standard methods are known for transplantation or infusion of various cells into a subject.

In methods which include the administration and uptake of exogenous DNA into the cells of a subject (for instance, gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector can be delivered in vivo by electroporation, one technology for which is available from Genetronics, Inc. (San Diego, Calif.) as well as by means of a SONOPORATION machine (ImaRx Pharmaceutical Corp., Tucson, Ariz.).

The compositions can be administered in vivo in a pharmaceutically acceptable carrier. The term "pharmaceutically acceptable" includes a material that is not biologically or otherwise undesirable, e.g., the material may be administered to a subject, along with the nucleic acid or vector, without causing substantial undesirable biological effects or interacting in a deleterious manner with any of the other components of the pharmaceutical composition in which it is contained. The carrier would usually be selected to minimize any degradation of the active ingredient(s) and to minimize any adverse side effects in the subject, as would be well known to one of ordinary skill in the art.

The compositions may be administered orally, parenterally (e.g. intravenously), by intramuscular injection, by intraperitoneal injection, transdermally, extracorporeally, topically or the like, although topical intranasal administration or administration by inhalant is considered to be preferred in some instance. As used herein, "topical intranasal administration" means delivery of the compositions into the nose and nasal passages through one or both of the nares, and can comprise delivery by a spraying mechanism or droplet mechanism, or through aerosolization of the nucleic acid or vector. The latter may be effective when a large number of subjects is to be treated simultaneously. Administration of the composition by inhalant can be through the nose or mouth via delivery by a spraying or droplet mechanism. Delivery also can be directly to any area of the respiratory system (e.g., lungs) via intubation.

The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. An appropriate amount can be determined by one of ordinary skill in the art using only routine experimentation given the teachings herein.

Parenteral administration of the composition, if used, is generally characterized by injection. Injectable compositions can be prepared in conventional forms, either as liquid solutions or suspensions, solid forms suitable for solution of suspension in liquid prior to injection, or as emulsions. More recently approaches for parenteral administration involve use of a slow release or sustained release system such that a constant dosage can be maintained.

The materials may be in solution or suspension (for example, incorporated into microparticles, liposomes, or cells). These may be targeted to a particular cell type via antibodies, receptors, or receptor ligands. The following references provide examples of the use of such technology to target specific proteins to tumor tissue (Senter et al., *Bioconjugate Chem.*, 2:447-451, 1991; Bagshawe, *Br. J. Cancer*, 60:275-281, 1989; Bagshawe et al., *Br. J. Cancer*, 58:700-703, 1988; Senter et al., *Bioconjugate Chem.*, 4:3-9, 1993; Battelli et al., *Cancer Immunol. Immunother.*, 35:421-425, 1992; Pietersz and McKenzie, *Immunolog. Reviews*, 129:57-80, 1992; and Roffler, et al., *Biochem. Pharmacol*, 42:2062-2065, 1991). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references provide examples of the use of such technology to target specific proteins to tumor tissue (Hughes et al., *Cancer Research*, 49:6214-6220, (1989); and Litzinger and Huang, *Biochimica et Biophysica Acta*, 1104:179-187, 1992). In general, receptors useful as targets for this type of delivery are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis have been reviewed (see, for instance, Brown and Greene, *DNA and Cell Biology* 10:6, 399-409, 1991).

The compositions, including particularly at least one MAC, can be used therapeutically in combination with a pharmaceutically acceptable carrier. Pharmaceutical carriers are known to those of ordinary skill in the art. These most typically would be standard carriers for administration of drugs to mammalian subjects such as humans, including solutions such as sterile water, saline, and buffered solutions at physiological pH.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, flavor maskers, diluents, emulsifiers, dispersing aids or binders may be desirable.

Some of the compositions, or combination therapy compounds administered with the described MACs, may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Other MACs which do not have a specific pharmaceutical function, but which may be used for tracking changes within cellular chromosomes or for the delivery of diagnostic tools for example, can be delivered in ways similar to those described for the pharmaceutical products.

The following examples are provided to illustrate certain particular features and/or embodiments. These examples should not be construed to limit the invention to the particular features or embodiments described.

EXAMPLES

Example 1

Generation of Long Synthetic Tandem Repeats

This example provides a description of methods for generating long synthetic tandem repeats using rolling-circle amplification, and for capturing these sequences using TAR.

Methods

Rolling-Circle Amplification

Rolling-circle amplification (RCA) was performed using an Amersham TempliPhi kit according to manufacturer's instructions, except that reactions were scaled-up to 100 µl and were spiked with a template specific primer mix to a final concentration of 2 pmoles/µl. The TempliPhi 100 DNA amplification kit has a sample buffer containing hexamers that prime DNA synthesis specifically; an enzyme mix containing Phi29 DNA polymerase and random hexamers, and a reaction buffer containing deoxyribonucleotides.

Optionally, the RCA reaction can be carried out using Phi29 DNA polymerase and exonuclease-resistant random hexamers with thiophosphate linkages for the two 3' terminal nucleotides. In a total volume of 10 µl, the final concentrations were 1 U/µl of Phi29 DNA polymerase and 4 pmol/µl of exonuclease-resistant random hexamers in 50 mM Tris-HCl buffer (pH 7.5), containing 10 mM $MgCl_2$, 10 mM $(NH_4)_2SO_4$, 200 ng/µl BSA, 4 mM DTT, 0.2 mM dNTP and template DNA.

Purified alphoid DNAs dissolved in water was used as a template for the RCA reaction. The amplification reaction was started by adding a premix from the TempliPhi kit of 5 µl of reaction buffer, 0.2 µl of enzyme mix and 1 µl of $MnCl_2$ (0-20 mM), followed by incubation at 30° C. for 12-16 hours. The mixture was subsequently heated at 65° C. for 10 min to inactivate the enzyme. The amount of amplified DNA was estimated by measuring its absorbance at 260 nm with a NanoDrop ND-1000 spectrophotometer (NanoDrop Technologies, Rockland, Del.).

RCA primers for alphoid DNA were AATCTGCA (SEQ ID NO: 1), ACTAGACA (SEQ ID NO: 2), ACAGAGTT (SEQ ID NO: 3) for the upper strand, and AGAGTGTT (SEQ ID NO: 4), TCTGAGAA (SEQ ID NO: 5), GGCCTCAA (SEQ ID NO: 6) for the lower strand. Primers for mouse major satellite were ACTTGACGA (SEQ ID NO: 7), TGCACACTGA (SEQ ID NO: 8) for the upper strand, and TTAGAAATGT (SEQ ID NO: 9), GAATATGGCG (SEQ ID NO: 10) for the lower strand. Primers for mouse minor satellite were AATGAGTT (SEQ ID NO: 11), TTCGTTGGAAACGGG (SEQ ID NO: 12) for the upper strand, and AGTGTGGTT (SEQ ID NO: 13) for the lower strand. Primers for human gamma-8 satellite were AATTCTGGG (SEQ ID NO: 14) for the upper strand, and CCAGAATT (SEQ ID NO: 15), GACACCTC (SEQ ID NO: 16) for the lower strand. Primers for the human Alu repeat were AATGTAGC (SEQ ID NO: 17), TCCTGAGCTCA (SEQ ID NO: 18) for the upper strand, and GTAATCCC (SEQ ID NO: 19) for the lower strand. All RCA primers carried thio-modified phosphate linkages for the last two bases of the 3' end.

Target templates were obtained by PCR from genomic DNA for mouse major, minor and human gamma-satellites, and by PCR from cloned human HPRT gene for the Alu repeat. Primers contained a restriction enzyme site such that the circular template would reconstitute a complete monomer after ligation. Typically one or two bases were substituted at the ligation junction as a result of the introduced restriction enzyme site. PCR primers are summarized in Table 1. PCR products were cloned into Invitrogen Topo vectors. The 2-mer, 4-mer, and 5-mer alphoid template DNAs were obtained by cloning directly into the pBluescript II EcoRI site from a EcoRI digested PAC clone containing ~35 copies of the human chromosome 21 11-mer.

TABLE 1

PCR Primers used for repeat unit isolation

| Name | Primer sequence | SEQ ID NO: | Repeat unit size |
|---|---|---|---|
| Mouse major F | 5' acgtgaattctggcgaggaaaactgaaaaaggtg 3' | 20 | 234 bp |
| Mouse major R | 5' gccagaattcacgtcctaaagtgtgtatttctca 3' | 21 | |
| Mouse minor F | 5' gagtgaattccactgaaaaacacattcgttggaaacggg 3' | 22 | 120 bp |
| Mouse minor R | 5' ttcagtggaattcactcatctaatatgttctacagtgtgg 3' | 23 | |
| Alu repeats F | 5' ttaaatgaattctgagcatggtggctcacacctgt 3' | 24 | 807 bp |
| Alu repeats R | 5' atttcagaattcgaagccaaggcagttggattgtt 3' | 25 | |
| Gamma 8 repeats F | 5' cgatgaaggcctctccgatcct 3' | 26 | 1,962 bp |
| Gamma 8 repeats R | 5' gaaagtcctgggggcttctgga 3' | 27 | |

Circular reaction templates were generated from gel-purified and ligated inserts derived from clones in PUC-base plasmids. Ligation was performed under dilute conditions at ~1 ng/µl. Circular templates were directly mixed into the RCA reaction at ~0.1-0.2 ng per 10 µl of reaction, and the reactions carried out for 12 hours (overnight tat 30° C.). Reaction products were phenol/chloroform extracted and ethanol precipitated prior to cloning. The size range and quantity of output double-stranded DNA was similar to that of a control reaction using PUC19 and random hexamers.

Extension (Concatamerization) of RCA Products by Recombinational Cloning in Yeast RCA products were cloned in yeast using a vector with appropriate hooks. Size of alphoid satellite hooks was ~40 bp. For other types of repeats the size of hooks was ~100 bp (Table 2).

Acids Res. 31:e29, 2003). RCA product (2-3 µg) and 0.2 µg of the linearized vector were used per transformation. Typically, under such conditions between 200 and 1,000 transformants were obtained. Omitting of RCA product from the transformation mix resulted in decrease of the yield of transformants to about 5-20 colonies. Optionally, the hook homology can be lowered to as low as about 85% identity, to increase recombination efficiency.

Individual His$^+$ transformants were streaked onto SD-His plates (~100 colonies per plate), incubated overnight at 30° C., and individual colonies were used for isolating high molecular weight yeast DNA. To determine the size of inserts, chromosomal-size yeast DNA was digested by NotI, separated by CHEF and blot hybridized with an insert-specific probe.

TABLE 2

Targeting hook sequences

| Name | Hook sequence | Product size |
|---|---|---|
| Mouse major 5' SEQ ID NO: 28 | 5' gatccggaccgatggcgaggaaaactgaaaaaggtggaa aatttagaaatgtccactgtaggacgtggaatatggcaagaaaact gaaaatcatggaaaatgagaaacatccacttgacgaacgcgt gatc 3' | 131 bp |
| Mouse major 3' SEQ ID NO: 29 | 5' gatcacgcgttgaaaaatgacgaaatcactaaaaacgtgaa aaatgagaaatgcacactgaaggacctggaatatggcgagaaaa ctgaaaatcacggaaaatgagaaatacacactttaggacgtgc ggaccggatc 3' | 138 bp |
| Mouse minor 5' SEQ ID NO: 30 | 5' gatccggaccgacagtgtatatcaatgagttacaatgagaaa catggaaaatgataaaaaccacactgtagaaacgcgtgatc 3' | 83 bp |
| Mouse minor 3' SEQ ID NO: 31 | 5' gatcacgcgtaacatattagatgagtgagttacactgaaaaac acattcgttggaaacgggatttgtagacggaccggatc 3' | 81 bp |
| Alu repeats 5' SEQ ID NO: 32 | 5' gatccggaccgtcaagaccagcctaggcaatgtagcgagac gccatctcaaaatattaaaaataagtaaataagtaaataaaaagaa ggttaagtatacaaatgtatttcctttgttgtgaatttatttcaattttatagtg attttttttttttgagacgaagtctcactcttgtcccacgcgtgatc 3' | 189 bp |
| Alu repeats 3' SEQ ID NO: 33 | 5' gatcacgcgtatcttggttcactgcaacctctgcgtgggctcaa gcaatcctcccacctcccctttccagagtagcggggaccacaggtgtg tgccaccacacctgactaattttttgcacggaccggatc 3' | 129 bp |
| Gamma 8 repeats 5' SEQ ID NO: 34 | 5' gatccggaccgactatggtggacattgtggtcaggcagaggt gagaagacagtgagaccgcagggaatgctgggagcctcctaggg atgtctctcccaccccagaagcttaccatngttgtttcggatgggctgt aatacccatgctttggtacgcgtgatc 3' | 163 bp |
| Gamma 8 repeats 3' SEQ ID NO: 35 | 5' gatcacgcgtgtagagggaagaattggcaagactgcaggt aatgctgcgaccctcccaaggagagcctctcccatcctagaagccc cccaggtctgtcacggataggctgtagtgtcggaccggatc 3' | 128 bp |
| Human alpha satellite 5' SEQ ID NO: 36 | 5' atgcatcgataagagtgtttcaaaactgctctatcaaaaggaa tgttcaacgcgtgatc 3' | 59 bp |
| Human alpha satellite 3' SEQ ID NO: 37 | 5' gatcacgcgtgagttgaatgcaaacttcacaaagaagtttctg agaatgctcgaggcatgcat 3' | 63 bp |

The basic targeting vector TAR-NV contains YAC (HIS3, CEN6, ARSH4) and BAC (Cm, ori F) cassettes as well as a mammalian selectable marker (Neo or BS). Before transformation, the vectors were linearized to release (expose) targeting hooks. The highly transformable S. cerevisiae strain VL6-48N (MATalpha, his3-A200, trp1-Δ1, ura3-Δ1, lys2, ade2-101, met14), which has HIS3 and URA3 deletions, was used for transformation. Conditions for spheroplast transformation have been described previously (Leem et al., Nucleic To convert YACs to BACs, DNAs from pooled transformants were electroporated into E. coli cells (DH10B or Stb14; Invitrogen. The yeast-bacteria-mammalian cell shuttle vector, BRV1, was used for retrofitting the large circular YACs for propagation as BACs and subsequent transfection into mammalian cells using the selectable marker NeoR. The vector contains two short (approximately 300 bp each) targeting sequences, A and B, flanking the ColE1 origin of replication in a pRS303-based TAR cloning vector. These targeting sequences are separated by an unique BamHI site. Recombination of the BamHI-linearized BRV1 vector with a YAC in yeast leads to replacement of the ColE1 origin of replication in the TAR cloning vector by a cassette containing the F-factor origin of replication, the chloramphenicol acetyl-transferase (CmR) gene, the NeoR gene, and the URA3 yeast selectable marker. A standard lithium acetate transformation procedure was used for retrofitting of HPRT YACs. YAC retrofitting was highly efficient: more than 95% of Ura+His+ transformants obtained with BRV1 contained retrofitted YACs. These constructs were moved to E. coli by electroporation using standard techniques. In brief, yeast chromosome-size DNAs were prepared in agarose plugs and, after melting and agarase treatment, the DNAs were electroporated into DH10B competent cells (GIBCO/BRL) by using a Bio-Rad Gene Pulser. Inserts were sized by CHEF after NotI digestion of BAC DNA isolated from 20 to 40 bacterial transformants for each construct.

In some cases, in order to further increase size of array, one or more additional rounds of recombinational cloning were carried. For this purpose, 5 μg of BAC DNA with the largest insert from the previous round of cloning was digested with SalI to cleave at the insert/vector junctions. The vector DNA was eliminated with an additional Sau3AI digestion. The final digest was precipitated with ethanol/sodium acetate and dissolved in 20 μl of water. Digested DNA (3-4 μg) and 0.2-0.3 μg of the linearized vector were used for yeast spheroplast transformation. The yield of clones with 2-3-fold larger insert size was 2-5%.

Results

Construction of Synthetic Tandem Arrays

The first step in the generation of synthetic tandem arrays involves in vitro rolling circle amplification (RCA) of repeats (FIG. 2A). Phi 29 polymerase has a high processivity and can extend newly replicated strands from circular double-stranded templates for several kilobases in vitro. Multiply-primed RCA results in hyper-branching of newly synthesized strands, yielding exponential amplification in copy number. Priming of 'hyper-branched' rolling-circle amplification is routinely achieved with random hexamers on complex DNA (Dean et al., Genome Res. 11:1095-1099, 2001). The low complexity of tandem repeat DNA, however, results in inefficient amplification with random primers. Therefore, for alphoid DNA repeats as well as for other types of repeats, specific exonuclease resistant primers based on conserved regions of the repeat monomer were synthesized. Cloned fragments derived from BAC inserts or PCR products amplified from genomic DNA were gel purified as restriction fragments and formed into circles by ligation to be used as template DNA. Cleavage and primer sites were chosen to reform a complete monomer upon ligation. Starting circular template taken from a dilute ligation reaction was as low as 0.1 ng per 10 μl of RCA reaction.

Dimer, 4-mer (quadramer), and 5-mer (pentamer) repeats of the alphoid 170-bp monomer were first used for RCA. All of these in the current example were derived from the human chromosome 21 type I 11-mer HOR (FIG. 1) (Ikeno et al., Nat. Biotechnol. 16:431-439, 1998; Ohzeki et al., J. Cell Biol. 159, 765-775, 2002). The smallest template DNA used in this example was a double-stranded 340 bp alphoid dimer. It is worth noting that RCA has been used successfully on single-stranded circular templates of 50-100 nucleotides in length (Fire & Xu, Proc. Natl. Acad. Sci. USA. 92:4641-4645, 1995), indicating that synthetic circular oligonucleotides can be used as a substrate and the resultant single-stranded linear product converted to double stranded DNA for analysis and cloning.

FIG. 3A illustrates RCA reactions for a 340 bp alphoid DNA dimer. Although DNA molecules with mobility higher than 20 kb are seen, they are likely to be reaction intermediates having anomalous migration (FIG. 3, lanes 1 and 2). Cleavage of reaction products with an appropriate enzyme resulted in restoration of the input template fragment (FIG. 3A, lanes 3 and 4), demonstrating the faithfulness of the polymerization. Similar results were obtained for RCA reactions with the 4-mer, the 5-mer and a 6-mer. The DNA yield from a 100 μl multiply-primed RCA reaction is sufficient for several cloning experiments.

The second step involves assembling of RCA products into long alphoid DNA arrays by in vivo homologous recombination in yeast. For this purpose, the RCA amplified products are co-transformed into yeast spheroplasts along with the targeting vector TAR-NV (FIG. 2B). Homologous recombination between the ends of RCA products results in a rescue of large tandem arrays in the targeting vector as circular YACs. Between 200 and 1,000 His+ transformants were typically obtained when a mixture containing 0.02 μg of the targeting vector and 3 μg of RCA reaction product generated from alphoid DNA units was used.

The results of analysis of transformants obtained with RCA product generated from a 5-mer alphoid DNA unit are presented herein. CHEF analysis of the YAC clones demonstrated that the majority of yeast transformants (120/120) contain alphoid DNA inserts with size bigger than 5 kb. In 20% of the transformants, the insert size was bigger than 15 kb. 5% of the transformants contain YACs in which array size ranged from 30 to 140 kb. The clones with inserts bigger than 30 kb were efficiently transferred into E. coli cells for further analysis (FIG. 3B). The same yield of clones carrying a large insert size was observed for 4-mer and 6-mer alphoid units.

The yield of recombinant clones with a large alphoid DNA arrays was lower when the 2-mer-based RCA product was used. While only 5% of the clones were larger than 15 kb, analysis of 200 transformants did not reveal inserts bigger than 50 kb, suggesting that large arrays generated from the 2-mer are less stable in yeast.

Several alphoid 2-mer-, 4-mer-, and 5-mer-based clones generated by in vivo recombinational cloning are shown in FIG. 3C, 3D and Table 3. Random sequencing from cloned arrays indicated that the resulting arrays faithfully reflect input template DNA. Non-alphoid tandem arrays were also synthesized, including those composed of mouse major and minor satellite, human gamma-8 satellite and human Alu repeat and then cloned by recombination in yeast using targeting vectors with appropriate hooks (Table 3).

We conclude that in vivo recombination in yeast is highly efficient in assembling fragments containing tandem repeats.

TABLE 3

Synthetic arrays generated from different types of repeats

| Repeat unit | Size of the unit (in kb) | Size of arrays (in kb) | Fold increase |
|---|---|---|---|
| Human alphoid DNA | | | |
| 2-mer | 0.34 | 27, 30, 35 | ×103 |
| 2-mer* | 0.34 | 30, 50 | ×147 |
| 4-mer | 0.68 | 40, 50, 70 | ×103 |
| 5-mer | 0.85 | 50, 120, 140 | ×165 |
| 6-mer | 1.02 | 35 | ×35 |
| Mouse major satellite, 3-mer | 0.7 | 55 | ×79 |
| Mouse minor satellite, 4-mer** | 0.5 | 10 | ×20 |

TABLE 3-continued

Synthetic arrays generated from different types of repeats

| Repeat unit | Size of the unit (in kb) | Size of arrays (in kb) | Fold increase |
|---|---|---|---|
| Human gamma-8, 10-mer** | 1.95 | 10 | ×5 |
| Human Alu, 3-mer** | 0.8 | 7.5 | ×9 |

*In this 2-mer the level of homology between two monomers is 70%.
**Apparent small size of inserts is due to the limited number of transformants analyzed.

Stability of Synthetic Centromeric Tandem Repeat Inserts

The synthetic arrays generated by RCA and recombinational cloning (described in Example 1) have a higher sequence identity per unit length than their endogenous counterparts, and therefore may have been less stable when cloned. However, 40-120 kb arrays generated from the 4-mer and 5-mer did not show significant instability in yeast. Clones containing alphoid DNA fragments isolated from chromosome 21 (11-mer-based array), and the clones with synthetic arrays derived from the 5-mer or 4-mer revealed single bands after their linearization followed by Southern blot hybridization. These inserts were also reasonably structurally stable during their propagation in a recA bacterial host (DH10B) at 30° C. (FIG. 3A, 3B). Growth of the cells at higher temperature (37° C.) resulted in some structural instability in the large blocks of alphoid DNA.

In contrast, the analysis of 2-mer-based alphoid repeat arrays bigger than 35 kb revealed a structural instability that could not be overcome by growing the cells at a lower temperature or changing the host strain (Stb14). Small deletions were observed in 10-20% of subclones. However, the 2-mer based arrays with a size of 25 kb were reasonably stable (FIG. 4C). This suggests that ~23% of divergence between two monomers in the 2-mer is not enough to maintain the array stably if their length is bigger than 35 kb. Increase of divergence up to 35% results in a significant stabilization of the array. With such a level of divergence we were able to generate a 50 kb 2-mer-based synthetic array that stably propagated in *E. coli* cells.

We conclude that despite a high sequence homology between alphoid monomers, synthetic arrays can be faithfully constructed and isolated, and will be useful for further studies including functional studies.

Example 2

Artificial Chromosomes with Long Synthetic Centromeric Tandem Repeats

This example provides a description of methods of delivering and analyzing HACs in cultured human cells.

Methods

Cell Culture and BAC DNA Transfection

Human fibrosarcoma cell line HT1080 was grown in DMEM medium supplemented with 10% FBS (Invitrogen), penicillin, streptomycin and glutamine. BAC DNA (400 ng) prepared as in Example 1 was purified using a Qiagen Large Construction kit (Qiagen) and transfected into $6 \times 10^5$ HT1080 cells using Lipofectamine reagent (Gibco BRL) according to the manufacture's instructions. Stable transformants were selected with 400 μg/ml of G418 (Wako).

Cytological Detection of Human Artificial Chromosomes

Standard techniques for fluorescence in situ hybridization (FISH) were carried out for the alphoid BAC transformed cell lines, essentially as previously described (Masumoto et al., *Exp. Cell Res.* 181:181-196, 1989). Two probes were used as controls to determine HAC formation: one corresponds to alphoid DNA in the repeats, and the other to the vector used for cloning alphoid DNA. If both probes stain the same region, HAC staining is considered real.

A 1868 bp p11-4 alphoid DNA probe (SEQ ID NO: 39) containing 11 copies of an alphoid DNA monomer (GI: 550080) was use to detect HAC generated from the amplified 5-mer alphoid DNA. Vector probe (4,661 bp from GI: 1817729; positions 1813 to 6473 of SEQ ID NO: 40) was generated using PCR from pBAC108L (GI: 1817729) using primers BACX (5'-CCCTCGAGTGAGCGAGGAAGCAC-CAGGG-3') (SEQ ID NO: 41) and BACS (5'-GCTCGTC-GACAGCGACACACTTGCATCGG-3') (SEQ ID NO: 42). PCR products were labeled using a nick translation kit with digoxygenin-11dUTP or biotin-16dUTP (Roche Diagnostics).

PCR products were amplified from HT1080 genome using three sets of primers for pan-alphoid DNA: α(1)18a (5'-ACA-GAAGCATTCTCAGAA-3') (SEQ ID NO: 43) and α(1)18b (5'-TTCTGAGAATGCTTCTGT-3') (SEQ ID NO: 44); alpha (Y)a (5'-AGAAACTTCTTTGTGATG-3') (SEQ ID NO: 45) and alpha(Y)b (5'-CATCACAAAGAAGTTTCT-3') (SEQ ID NO: 46); CB15a (5'-TCGTTGGAAACGGGA-3') (SEQ ID NO: 47) and CB15b (5'-TCCCGTTTCCAACGA-3') (SEQ ID NO: 48). See also Ohzeki et al., *J. Cell Biol.* 159, 765-775, 2002; Ikeno et al., *Hum. Mol. Genet.* 3:1245-1257, 1994; and Masumoto et al., *Chromosoma* 107:406-416, 1998.

Plasmid DNAs or PCR products were labeled using a nick translation kit with digoxigenin-11dUTP or biotin16-dUTP (Roche Diagnostics). Indirect immunofluorescence and simultaneous staining by FISH were carried out as previously described (Masumoto et al., *Exp. Cell Res.* 181:181-196, 1989). Antibodies used were anti-CENP-A (mAN1, Masumoto et al., *Chromosoma* 107:406-416, 1998), anti-CENP-B (2D8D8, Ohzeki et al., *J. Cell Biol.* 159, 765-775, 2002) and anti-CENP-E (mAb177, Yen et al., *EMBO J.* 10:1245-1254, 1991). Images were captured using a cooled-CCD camera (PXL, Photometrics Ltd) mounted on Zeiss microscope, and analyzed by IPLab software (Signal Analytics).

Results

A Synthetic Alphoid DNA Array is Competent in HAC Formation

All HACs reported to date have used a native higher-order repeat (HOR) as the basic repeat structure for the centromeric sequence. It is not known if artificially constructed arrays are competent for de novo centromere formation in human cells. To further validate the cloned arrays, we attempted to generate HACs in cultured cells using the ~120 kb 5-mer-based synthetic array generated as in Example 1. The 5-mer array was derived as a subfragment of the human chromosome 21, 11-mer HOR that has been used successfully for de novo HAC formation (Ohzeki et al., *J. Cell Biol.* 159, 765-775, 2002). The 5-mer array contains a CENP-B box density similar to that of the 11-mer (2.63 vs. 2.35 per kb, respectively). The native 11-mer contains one monomer with a mutant CENP-B box that cannot bind CENP-B (Ohzeki et al., *J. Cell Biol.* 159, 765-775, 2002). The 5-mer retains this monomer. The ratio of mutant to canonical CENP-B boxes is elevated 3.4-fold in the 5-mer.

Figure 5C:
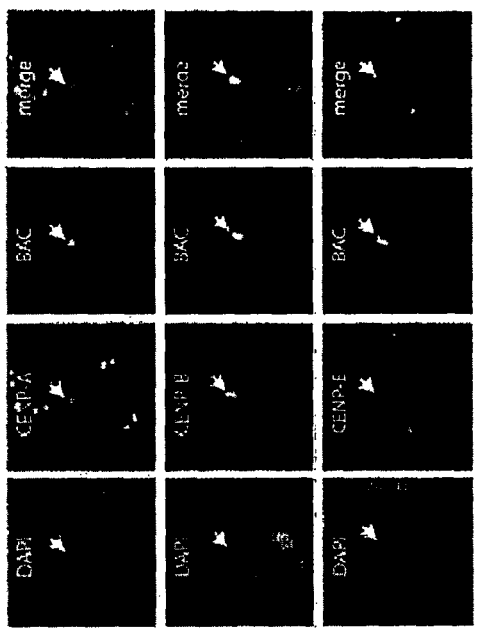
FIGS. 5A-5C are a series of chromosome spreads showing HAC formation using the 120 kb synthetic alphoid 5-mer-based array.
Figure 5B:
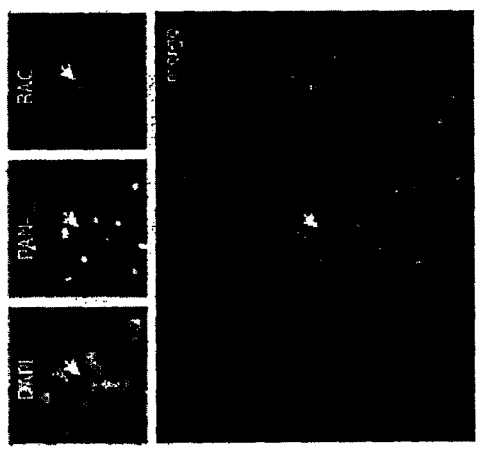
Figure 5A:
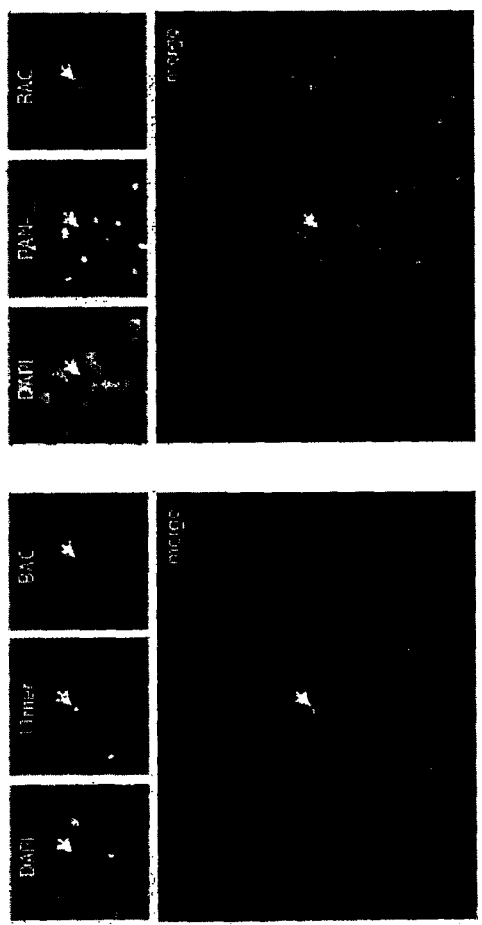

Following lipofection of BAC DNA to HT1080 cells and G418 selection, 29 resistant cell lines were expanded and examined for the presence of HACs by dual FISH with BAC and human chromosome 21 alphoid probes. Three cell lines (10%) were found to contain candidate HACs with 50% or more of individual mitotic cell spreads showing HAC signals (FIG. 5A). A control transfection performed in parallel using a BAC with a 60 kb insert of the complete 11-mer yielded 17% of examined colonies with HACs in at least 50% of cells. Size and copy number of the HACs was in the range normally reported for de novo formation. A pan-alphoid probe (blocked for chromosome 21 specific alphoid sequence) did not hybridize to the HACs (clone HT4-10 in FIG. 5B), suggesting that these three HACs had been assembled without recruiting any endogenous functioning centromere sequences. The candidate HACs also bind to CENP-A and CENP-E, two centromere proteins found at functioning kinetochores, and also are all covered with strong CENP-B signals (FIG. 5C), indicating that the 5-mer array has formed the functional centromere de novo.

Discussion

The ability to relatively rapidly construct defined alphoid construct variants will greatly increase the feasibility of exploring the sequence requirements for de novo centromere assembly. Previously two groups reported the construction of synthetic alphoid arrays using repetitive directional ligation on the basis of a native higher-order repeat fragment of 2-3 kb (Harrington et al., *Nat. Genet.* 15:345-355, 1997; Ohzeki et al., *J. Cell Biol.* 159, 765-775, 2002; Basu et al., *Nucleic Acids Res.* 33:587-596, 2005). This approach has two main limitations. Firstly, it is a slow, laborious strategy not easily scaled up for rapid generation of tandem repeats with engineered changes. More important, the method suggests the use of artificially introduced restriction sites that will remain in multiple copies in the final constructs.

In the examples herein, we describe a new strategy to generate large synthetic DNA repeats with a predetermined structure by in vivo recombination in yeast. Synthetic arrays were generated from the different "units" of alphoid DNA, including an alphoid DNA 2-mer. We also showed that their structural stability is sufficient to carry out functional tests and to be used in functional mammalian artificial chromosome. We examined the capacity of a 5-mer-based 120 kb array generated from a part of the native 11-mer HOR to form a HAC. The 3.4-fold higher frequency of mutant CENP-B boxes in the 5-mer when compared to the native 11-mer did not result in a loss of HACs formation. The specific mutations in the CENP-B box are known to abolish CENP-B binding and all unmodified HORs used as a basis for HAC formation carry one or more monomers with defective CENP-B boxes. Our data suggests that there is minimal negative gain-of-function effect, if any, on formation efficiency due to these mutations. This is in agreement with a recent paper describing analysis of synthetic alphoid DNA arrays generated by repetitive ligation of a 16-mer from chromosome 17 (Basu et al., *Nucleic Acids Res.* 33:587-596, 2005).

The assembly of de novo centromeres from the artificially constructed 5-mer-based synthetic array occurred with an efficiency similar to that for native alphoid DNA fragments, suggesting that the existence of a HOR structure for type I arrays at human centromeres is a by-product of human-specific evolutionary mechanisms. The rapid evolution of centromere repeats among different species is consistent with this view. A higher-order repeat structure has not been detected as yet at the centromeres for most of the organisms for which centromeric tandem repeats have been identified (Guenatri et al., *J. Cell Biol.* 166:493-505, 2004; Jiang et al., *Trends Plant. Sci.* 8:570-575, 2003; Sun et al., *Genome Res.* 13:182-194, 2003).

Alphoid repeats from different centromeres are not equivalent in their ability to assemble de novo centromeres (Kouprina et al., *Nucleic Acids Res.* 31:922-934, 2003; Schueler et al., *Science* 1294:109-115, 2001). The presence of the CENP-B box is necessary to trigger efficient assembly, yet it is clear that other sequence signals also play a role. These may be unknown motifs that bind centromere proteins or non-specific sequence signal(s) based on epigenetic chromatin assembly. The interplay between such factors and the CENP-B protein may not be equivalent among randomly cloned alphoid repeats. The method presented here is a powerful technique for investigations into the sequence requirements of centromeric tandem repeat function.

There are many other varieties of tandem repeats populating the genomes of eukaryotes, some of which are known to play important roles in cell function by forming or maintaining specialized chromatin required for chromosome segregation, the stabilizing of chromosome ends, or gene regulation, and may be an important substrate for rapid evolution. Because many types of DNA repeats may be similarly amplified, the method provided herein has more general application to exploit such repeats in various roles and to elucidate the role of tandem repeats in the genome. For example, by creating a set of nonalphoid DNA arrays (for instance, human gamma-8 satellite, mouse major and minor satellites, and Alu), the question of how the composition and length of a tandem repeat array effects heterochromatin formation can be address by targeting the arrays to a structurally defined ectopic chromosomal site by Cre-lox site-specific recombination. Such research may also shed light on, and assist in overcoming or controlling the phenomenon of repeat-induced gene silencing that prevents transgene expression (McBurney et al., *Exp. Cell Res.* 1274:1-8, 2002).

Amplified non-alphoid DNA arrays may be also useful for construction of a new generation of HACs. As shown, previous systems of HAC formation have been accompanied by amplification of input constructs (Harrington et al., *Nat. Genet.* 15:345-355, 1997; Ikeno et al., *Nat. Biotechnol.* 16:431-439, 1998; Ebersole et al., *Hum. Mol. Genet.* 9:1623-1631, 2000; Larin & Mejia, *Trends Genet.* 18:313-319, 2002; Laner et al., *Cytogenet. Genome Res.* 107:9-13, 2004; Ohzeki et al., *J. Cell Biol.* 159, 765-775, 2002; Kouprina et al., *Nucleic Acids Res.* 31:922-934, 2003; Basu et al., *Nucleic Acids Res.* 33:587-596, 2005). Mounting evidence indicates that constitutive heterochromatin may also be required for proper centromere function (Bernard & Allshire, *Trends Cell. Biol.* 12:419-424, 2002; Bailis & Forsburg, *Cell Cycle* 3:416-418, 2004). One may suggest that a lack of a heterochromatin-forming domain within a transforming construct is a cause of its multimerization. Combination of synthetic alphoid arrays with non-alphoid DNA arrays may prevent such events. Mouse major satellite repeats forming megabase-size blocks in pericentromeric regions are candidates for heterochromatin forming domain in HAC constructs. They do not associate with CENP-A or other kinetochore-specific proteins; instead, they are highly heterochromatic and are believed to play a role in centromere stabilization.

Example 3

Production of a Human Artificial Chromosome with a Conditional Centromere

This example describes production of a human artificial chromosome (HAC) with a regulated centromere. The HAC was generated from a tandem array of an artificial alpha-satellite dimer. CENP-B box in one monomer was replaced by a 42 bp tetracycline operator (tetO) sequence. The tetO sequences enable visualizing the HAC, for instance during mitotic divisions. They also provide "handles" by which any desired protein can be targeted to the HAC centromere as a tetracycline repressor fusion protein. The fusion protein is useful, for instance, to monitor an effect of targeting on stability of the HAC, or to intentionally alter (e.g., reduce) stability of the HAC.

Such a targeting revealed that the centromeric protein CENP-H, and the heterochromatin protein HP1, have no detectable effect for HAC segregation. In contrast, targeting of the tetracycline Trans-Activator protein (tTA), a fusion of the Tet-Repressor and the transcriptional activation domain of VP16, dramatically destabilized the HAC. This indicates that transcriptionally competent, open chromatin structure within the main component of the HAC may compromise centromere function.

The ability to selectively target different proteins into a HAC and regulate centromere function opens the way for functional and structural analysis of the human centromere, kinetochore and heterochromatin, as well as for new HAC-based, regulatable gene expression systems.

HAC analyses in human HT1080 cells demonstrated the importance of alphoid DNA and CENP-B box, typical of human centromere DNA configuration, for de novo functional centromere assembly as a stable chromosome. CENP-A chromatin clusters preferentially assembled on the insert alphoid DNA and the modified histone H3 nucleosomes assembled on the YAC vector arm. While HACs became the most suitable system to investigate de novo centromere/kinetochore formation, the mechanisms of HAC formation have not yet been completely understood. All the alphoid YAC/BAC DNA introduced into cells were multimerized. HAC formation usually occurred with 30% of transformed cell line and did not occur in 100% of transformed cell lines. Thus, epigenetic chromatin assembly mechanisms were involved in the fate of the input DNA, HAC formation or integration. The insertion of additional transcriptional marker gene(s) on the YAC/BAC vector arms significantly decreased HAC formation activity. Despite this failure in HAC formation, centromere components (CENP-A, -B, -C) assembled at the integration sites correlating with a transcriptionally active state on both vector arms which are not compatible with heterochromatin formation, suggesting that epigenetic assembly of heterochromatin is required for the establishment of a stable artificial chromosome.

Observation of a GFP tagged HAC in living mitotic HT1080 cells showed that HACs are accurately aligned at the spindle equator by controlling the tension balance and the sister chromatids of the HAC are resolved at the same timing as natural chromosome separation synchronizes with mitotic cell cycle progression. Thus, CENP-A chromatin clusters and the modified histone H3 nucleosomes assembled on the multimer of the input alphoid YAC can provide a common foundation not only for the functional CENP-A chromatin core but also for the most mechanisms required for the stable chromosomes. Thus, the first-generation HACs have an advantage for identifying the important structure required for a stable human chromosome because they consist entirely of introduced alphoid YAC/BAC DNA molecules.

It was hypothesized that the tetracycline operator (tetO) sequences would provide a "handle" by which any desired protein could be targeted to the HAC centromere as a tetracycline repressor (tetR) fusion protein. This kind of regulatable (conditional) HAC construct enables analysis of the structure required for chromosome segregation process in vivo, and can be used for regulatable gene expression in many contexts.

The tetracycline operator-repressor system is a well-established system used for regulating protein-DNA interactions in mammalian cells. The system is generally used for regulated gene expression, since TetR-fused with the transcriptional activation domain of virion protein VP16 of herpes simplex virus (HSV) can induce gene expression of target genes under the control of an attenuated CMV promoter containing tetO motifs. VP16 forms a transcriptional regulatory complex. The transcriptional activation domain (AD) of the VP16 protein has been shown to directly interact with several general transcription factors including the TATA-binding protein (TBP), TFIIB, and the SAGA histone acetylase complex in vivo. Through these interactions, tetR-VP16 AD fusion proteins (tTA) are known to stimulate chromatin remodeling and mRNA initiation by RNA polymerase II at the promoter. Therefore, assembly of tTA induces a transcriptionally competent open chromatin structure around its binding site.

In this example, the first regulatable (conditional) human artificial chromosome (HAC) is described in which an artificial DNA sequence has been used to construct a functional centromere. This system is exemplified in the HT1080 cell line. This HAC is based on an artificially designed alpha-satellite (alphoid) dimer in which one monomer of 167 bp is natural, coming from human chromosome 17, and includes a binding site for CENP-B (CENP-B box). The other monomer is artificial, corresponding to the 171 bp consensus sequence for human alpha-satellite DNA identified by Choo and Vissel (*Nucleic Acids Res.* 19, 1179-1182, 1991), except that the 42 bp tetO has been inserted in the position where the CENP-B box would normally be found (see FIG. 6A).

HAC analyses in human HT1080 cells demonstrated the importance of alphoid DNA and CENP-B box, typical of human centromere DNA configuration, for de novo functional centromere assembly as a stable chromosome. CENP-A chromatin clusters preferentially assembled on the insert alphoid DNA and the modified histone H3 nucleosomes assembled on the YAC vector arm. While HACs are recognized as a powerful system to investigate de novo centromere/kinetochore formation, the mechanisms of HAC formation have not yet been completely understood. During HAC formation, all the alphoid YAC/BAC DNA introduced into cells is typically multimerized. HAC formation usually occurs in about 30% of the transformed cell line and does not occur in 100% of transformed cell lines. Thus, epigenetic chromatin assembly mechanisms may be involved in the fate of the input DNA, which can be either HAC formation or integration. The insertion of additional transcriptional marker gene(s) on the YAC/BAC vector arms significantly decreased HAC formation activity. Despite this failure in HAC formation, centromere components (CENP-A, -B, -C) assembled at the sites where the YAC/BAC vector had integrated into a host chromosome. The preference for integrating into host chromosomes as opposed to forming a HAC correlated with a transcriptionally active state on both vector arms. Apparently, transcription of the YAC/BAC vector is not compatible with heterochromatin formation. This suggests that epigenetic assembly of heterochromatin is required for the establishment of a stable artificial chromosome.

Observation of a GFP tagged HAC in living mitotic HT1080 cells showed that HACs are accurately aligned at the spindle equator by controlling the tension balance resulting from attachment of the sister kinetochores to opposite spindle poles, and the sister chromatids of the HAC are resolved at the same timing as the sister chromatids of the natural chromosomes. This separation is synchronized with mitotic cell cycle progression. Thus, CENP-A chromatin clusters and the modified histone H3 nucleosomes assembled on the multimer of the input alphoid YAC can provide a common foundation not only for the functional CENP-A chromatin core but also for the most mechanisms required for the stable chromosomes. Thus, the first-generation HACs provide an advantage for identifying the important structure required for a stable human chromosome because they consist entirely of introduced alphoid YAC/BAC DNA molecules.

Synthetic Alphoid DNA with tetO Sequence Retained HAC Formation Activity.

An artificial alphoid dimer was generated (using methods essentially similar to those in Examples 1 and 2) as a repeat unit, consisting of an alphoid monomer derived from chromosome 17 alphoid 16-mer (which includes a CENP-B binding motif (CENP-B box)) and a consensus alphoid monomer in which sequence corresponding to the CENP-B box was replaced with a 42 bp fragment containing a tetO motif (FIG. 6A). For most efficient HAC formation, the candidate alphoid DNA length should be more than 50 kb, because 50-70 kb alphoid DNA showed similar high efficiency for the HAC formation.

Figure 7:
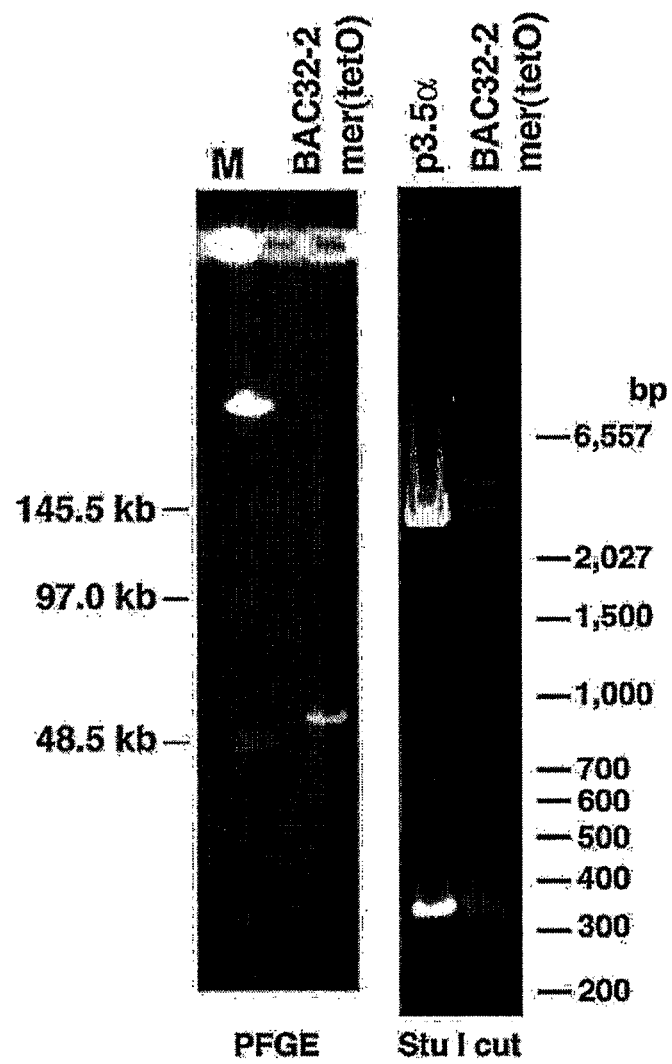
FIG. 7 shows an ethidium bromide stained gel following pulsed-field gel electrophoresis (PFGE) of *E. coli* genomic DNA containing the BAC32-2mer(tetO) treated with NotI restriction enzyme (left panel). Structural analysis of BAC32-2mer(tetO) with the restriction enzyme (right panel). BAC32-2mer(tetO) and p3.5α (a plasmid containing 10 repeats of tetO dimer alphoid) were treated by StuI, which restriction site appears once per tetO dimer alphoid DNA.

To extend the modified tetO alphoid dimer, rolling circle amplification was applied using φ29phage DNA polymerase and transformation-associated recombination (TAR) cloning in yeast (FIG. 6B; Ebersole et al., *Nucleic Acids Res.* 2005; 33(15): e130). This yielded a 50 kb of tetO dimer alphoid repeat cloned in a BAC vector (BAC32-2mer (tetO)). Restriction analysis with StuI restriction enzyme digestion (the StuI site occurs once per tetO dimer) showed that the DNA construct of tetO dimer repeats did not change during the extension processes (FIG. 7).

The 50 kb of tetO dimer alphoid DNA (BAC32-2mer (tetO)) was introduced into human HT1080 cells for HAC formation, using methods essentially as described above. FISH analyses of the transformants with a chromosome 17-specific alphoid probe and a BAC probe indicated that HACs with these probe signals were formed in two cell lines of the analyzed 46 transformants (FIG. 6C and Table 4). This level of HAC formation is lower than the frequency of HAC formation found when using cloned bona fide centromeric alphoid DNA—possibly because epigenetic events necessary for centromere formation occur less readily on the artificial DNA sequence. In spite of this, the resulting HACs appear to have normal stability.

TABLE 4

Efficiency of HAC formation following transfection with BAC32-2mer(tetO) DNA

| Introduced DNA | Analyzed cell lines | No. of cell lines: either HAC or integration signals as the predominant fate of transfected DNA | | |
|---|---|---|---|---|
| | | HAC | Mini-chromosome recruited a host fragment | Host chromosomal integration |
| wild type 11.32 (60 kb) | 41 | 12 (29.3%) | 0 | 29 (70.7%) |
| BAC32-2mer(tetO) (50 kb) | 46 | 2 (4.3%) | 4 (8.7%) | 40 (87.0%) |

However, HAC formation efficiency was lower (4.3%) and the portion of cell population containing a HAC in each cell line was also lower (35.7% or 28.6% of cells) than the HAC formation efficiencies of wt 60 kb 11-mer alphoid BAC made from chromosome 21 type I alphoid DNA (α21-I) (30% of analyzed cell lines contained HAC within more than 50% of the cell population). In some cases, BAC32-2mer(tetO) also caused mini-chromosome formation accompanied with a truncated host chromosomal arm fragments in four of 46 cell lines. These results suggested that replacement of tetO in an alphoid unit affected a decrease in the HAC formation efficiency and an increase in generation of truncated mini-chromosomes. FISH analysis of HACs with inter- and intra-Alu PCR probes indicated that a weaker signal was detected on the HACs than the lowest signal on host chromosomes; in some instances, almost no signal was detected. This indicates that the HACs were formed without recruiting detectable host chromosomal fragment. Thus, although formation efficiency was low, tetO alphoid DNA still retained HAC formation activity.

Several sub-cell lines were obtained, containing one copy of the HAC in most cells from the original two-HAC cell lines (Table 5). In those sub-cell lines, HACs were maintained stably even in non-selective condition (R=0.0024, or 0.0054, Table 5).

TABLE 5

HAC frequency in BAC32-2mer(tetO) derived cell lines and stability of the HACs

| | | ratio of cells: either HAC or integration signals as the predominant fate of transfected DNA | | |
|---|---|---|---|---|
| | | | Host chromosomal integration | |
| clones | loss rate | HAC | centromere | arm |
| AB2-2-18 | | 35.7% | 0 | 64.3% |
| AB2-2-18-21* | 0.0024 | 100% | 0 | 0 |
| AB2-5-4 | | 28.6% | 71.4% | 0 |
| AB2-5-4-19** | 0.0054 | 100% | 0 | 0 |

*a subclone from AB2-2-18
**a subclone from AB2-5-4

Figures 8A, 8B, 8C, 8D, 8E:
FIGS. 8A-8E are a series of micrographs, illustrating that the HAC segregates correctly in mitosis.

FISH analysis with a BAC probe indicated that during prometaphase to metaphase, BAC signal on the HAC aligned at the metaphase plate. The signals were separated to each spindle poles with the same timing as the host chromosomes in anaphase. Finally HAC signals were detected in the separated sister nuclei (FIG. 8). Thus, the HAC containing tetO alphoid DNA segregates correctly.

Tetracycline Repressor (tetR) and Functional Centromere Proteins Assembled at tetO Alphoid Sequence on the HAC.

To confirm that the tetR protein can target the tetO sequences on the HAC, RFP-tetR fusion protein was expressed in cells containing BAC32-2mer(tetO). The signal of RFP-tetR was observed as a single dot in interphase nuclei, where the RFP-tetR signal on the HAC overlapped with all of the centromere proteins tested, including CENP-A, CENP-B, CENP-C and CENP-H (FIGS. 9 and 10). These results indicate that once formed, the tetO alphoid HAC was stably maintained with functional assembly of centromere protein CENP-A, -B, -C, and -H, and that it can be targeted with tetR fusion proteins.

Several Different Chromatin Structures Were Formed on tetO Alphoid HAC.

To confirm whether CENP-A and CENP-B observed by indirect immunofluorescence on tetO alphoid HAC were directly assembled to the tetO alphoid DNA, analyzed tetO alphoid HAC were analyzed using a chromatin immunoprecipitation (ChIP) assay (FIG. 11). Antibodies against CENP-A and CENP-B enriched the tetO alphoid unit on the HAC in immunoprecipitates, similar to the enrichments of endogenous 11-mer alphoid on chromosome 21 at the centromere and the synthetic 11-mer on the control HAC (FIGS. 11A and 11B). These results indicate that existence of tetO sequence did not inhibit directly the assembly of CENP-A and -B on the tetO alphoid sequences.

Figure 11A:
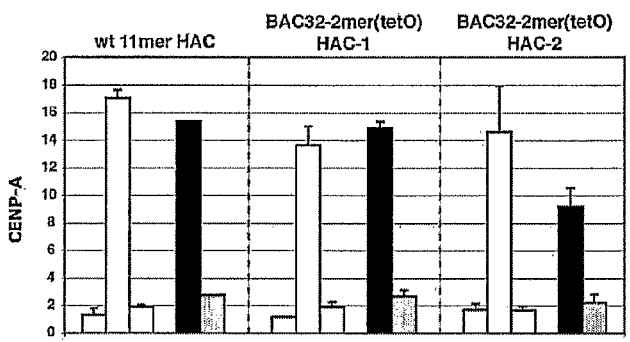
FIGS. 11A-11E are a series of bar charts, illustrating ChIP analysis of CENPs assembly and modified histone H3 at the tetO alphoid HACs. The results of ChIP analysis using antibodies against CENP-A (FIG. 11A), CENP-B (FIG. 11B), dimethylated histone H3 Lys4 (H3K4me2, FIG. 11C), trimethylated histone H3 Lys4 (H3K4me3, FIG. 11D) and trimethylated histone H3 Lys9 (H3K9me3, FIG. 11E) are illustrated. The assemblies of these proteins on the control HAC derived from the 60 kb synthetic chromosome 21 type I 11-mer alphoid BAC (left), on the tetO alphoid HACs in AB2-2-18-21 sub-cell line (middle) and in AB2-5-4-19 sub-cell line (right) were shown. The bar charts show the relative rate of recovery of the target DNA loci by immunoprecipitation with each antibodies, calculated by dividing percentage recovery of each DNA locus (5S rDNA, chromosome 21 alphoid DNA, Sat2, synthetic alphoid DNA and the selective marker gene) by those of the mouse normal IgG. Error bars indicate s.d. (n=3). The average recovery of synthetic alphoid DNA (tetO dimer alphoid and synthetic 11-mer) and chromosome 21 type I 11-mer alphoid DNA with anti CENP-A and CENP-B antibodies compared with those of the marker genes, 5S ribosomal DNA and Sat2 were significantly different (P<0.05). The average recoveries of tetO dimer alphoid by anti H3K4me2 antibody were significantly higher than that of the synthetic 11-mer of control HAC and chromosome 21 type I 11-mer (P<0.05).
Figure 11B:
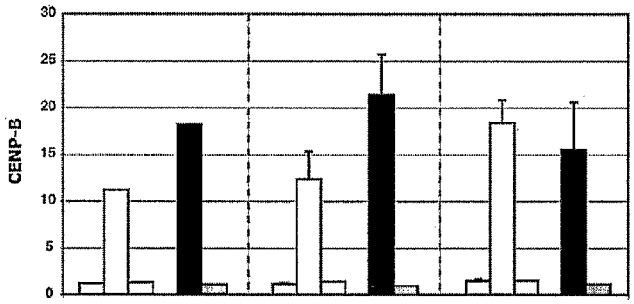
Figure 11C:
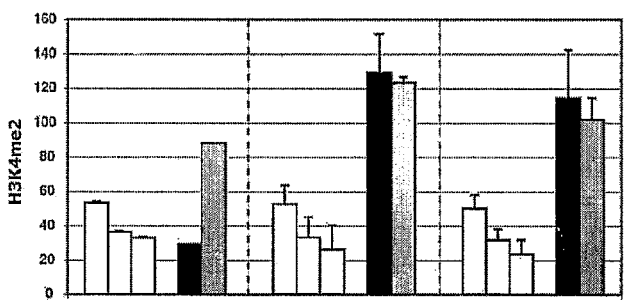

To analyze whether the inclusion of tetO sequence affects other aspects of chromatin assembly on the tetO alphoid HAC, ChIP assays were carried out using antibodies against modified histones H3 (H3k4me2, H3K4me3, H3K9me3). Transcriptionally competent H3K4me2 associated with tetO alphoid on the HAC at a high level comparable with the endogenous 11-mer alphoid on chromosome 21 at the centromere and the synthetic 11-mer on the control HAC (FIG. 11C). This result suggests that tetO alphoid HAC tends to form a neutral or more open chromatin. The tendency of tetO alphoid HAC to form more open chromatin might depend on the inclusions the tetO motif in the alphoid unit.

Figure 11D:
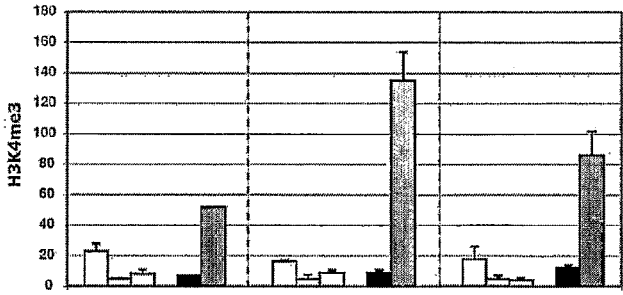

Transcriptionally active H3K4me3 assembled at the marker gene on tetO alphoid HAC at a high level, but at low levels at the tetO alphoid itself, as well as at endogenous 11-mer alphoid on chromosome 21 at the centromere and the synthetic 11-mer on the control HAC (FIG. 11D).

Figure 11E:
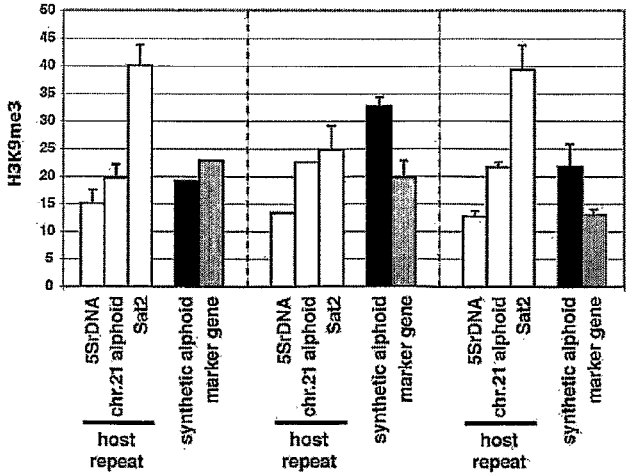

Heterochromatic H3K9me3 assembled on the tetO alphoid sequences at a level similar to that on the synthetic 11-mer on the control HAC (FIG. 11E). This is consistent with previous observations that acquisition of heterochromatin structure is also necessary for the stable HAC coincident with the assembly of a kinetochore structure (Nakashima et al., *J Cell Sci.* 118(24):5885-98, 2005).

All these results suggest that, although the introduced BAC32-2mer(tetO) tends to form a more open chromatin structure (as detected by association with H3K4me2), similar distinctive chromatin structures (H3K9me3 and CENP-A) assembled on the tetO alphoid HAC as well as at the wildtype synthetic 11-mer on the control HAC. Because the tetO alphoid HAC exhibits the same high stability characteristic of HACs containing only canonical human alphoid DNA, this observation indicates that the differences are not critical for function of the kinetochore established on the novel HAC.

Binding of tTA (tetR-VP16) Induced tetO Dimer HAC Loss.

Figure 12A:
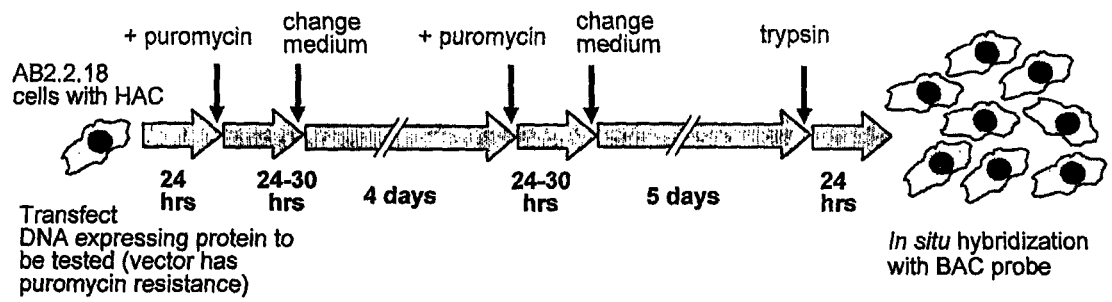
FIGS. 12A-12C illustrate transcriptional activator targeting into the HAC functionally inactivates the kinetochore.
Figure 12B:
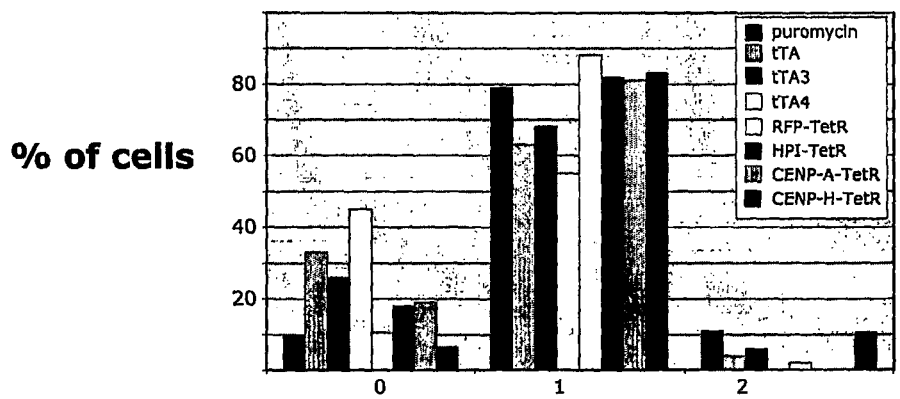
Figure 12C:
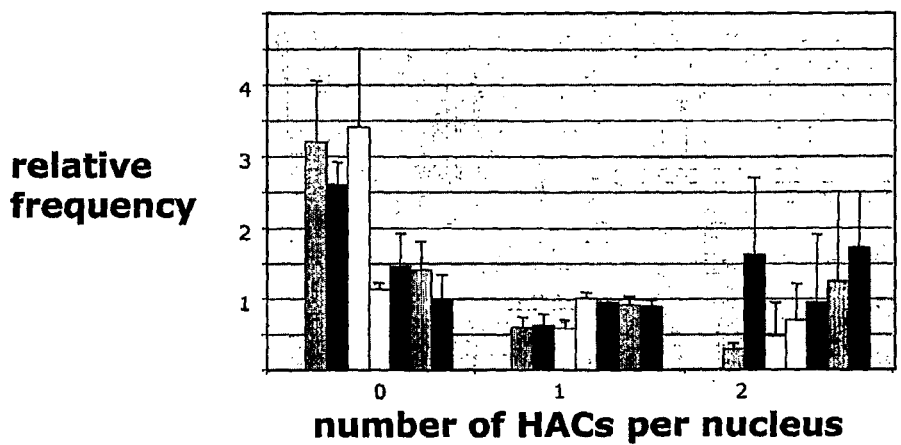

All of the analyzed HACs assembled centromere chromatin (CENP-A assembly), euchromatin (H3K4me2, H3K4me3) and heterochromatin (H3K9me3) structures on the multimer of the input alphoid YAC/BAC DNA. If these epigenetic chromatin assemblies are necessary for stable chromosome segregation, the targeting of tTA on tetO alphoid sequence and the induction of transcriptionally competent open chromatin was proposed to affect stability of the HAC.

tTA, tTA3 and tTA4 (mutant proteins of tTA) were expressed in clones containing the tetO dimer HAC. After 12 days of culture without selective condition, HAC copy numbers of polyclonal transformants were counted by FISH analysis (FIG. 12). Co-expression of tTA proteins caused a drastic destabilization of the tetO containing HAC, which was lost in 23-45% of tTA (and its mutants) expressing cells. The frequency of cells lacking the HAC was 2.5-3.4 fold higher than the number of cells lacking the control vector or tetR transformed cells, whereas those cells expressing HP1, CENP-A or CENP-H fused with tetR showed <1.4 fold loss.

Figure 13:
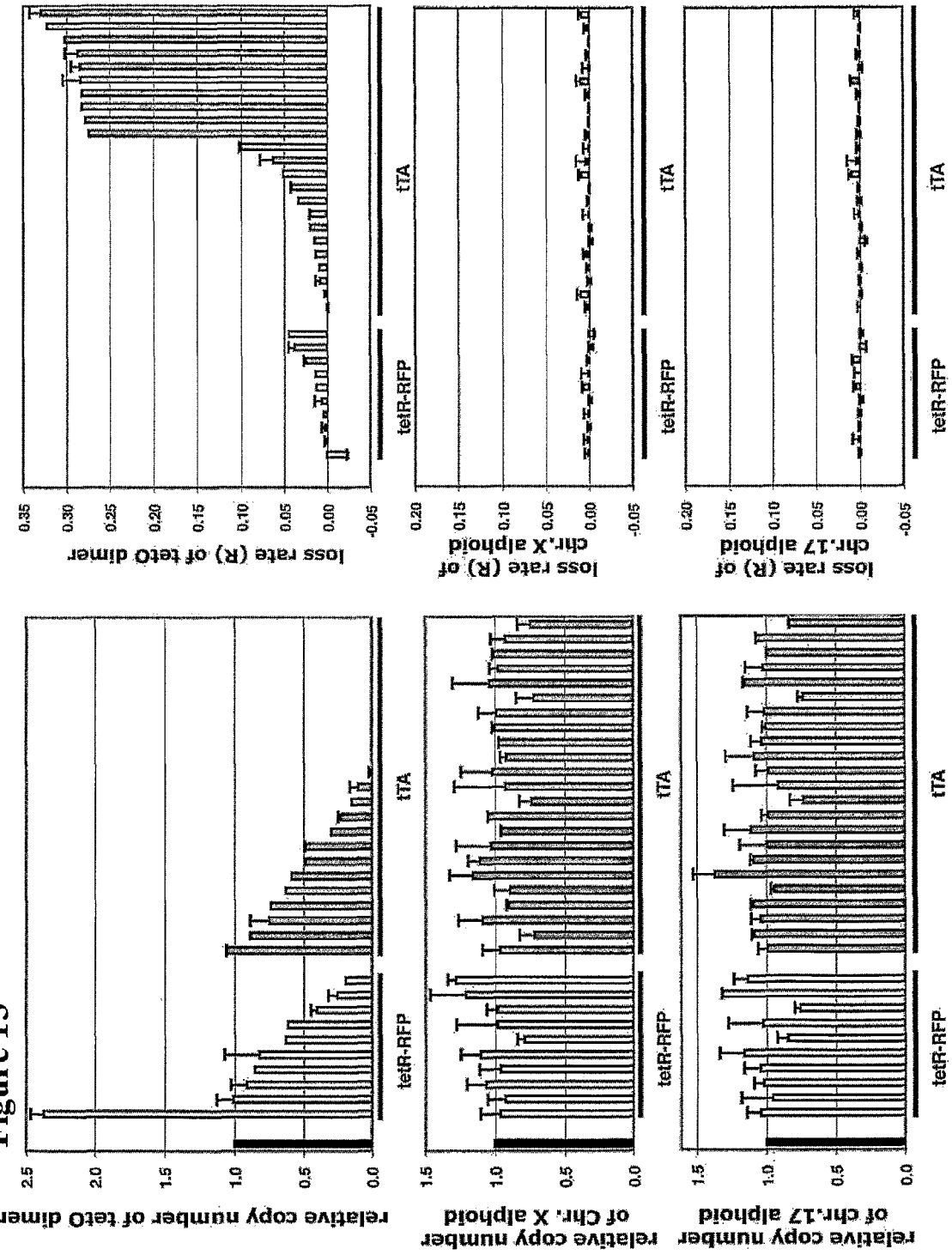
FIG. 13 shows the results of a colony assay for the tTA induced instability of the tetO alphoid HAC. The relative copy numbers of tetO dimer alphoid DNA in individual 23 colonies of tTA (gray bars) or 10 colonies of RFP-tetR (white bars) expressing HAC sub-cell line (AB2-5-4-19) against that of original cell line (black bar) were analyzed by real-time PCR (left upper panel). Colonies were cultured in non-selective media for 37 days. Chromosome loss rate of the tetO alphoid HAC per generation of the colonies was calculated with a formula (N=a relative copy number of the tetO alphoid, $N_{37}=(1-R)^{37}$) (right upper panel). A significant loss of the tetO alphoid HAC was observed in 10 colonies (43.5%) of tTA expressing cell lines (P<0.01). The relative copy numbers of host chromosome X (left middle panel) and chromosome 17 (left lower panel) alphoid DNA were shown. The loss rate of host alphoid DNAs (right panels) in tTA or RFP-tetR expressing colonies did not significantly change with those of RFP-tetR expression cells (P>0.15 or 0.83). Bars indicate s.d.

The copy number of tetO alphoid DNA in single isolated tetR- or tTA-expressing cell lines was analyzed by real-time PCR (FIG. 13). The loss rate of the HAC (R) after 37 days culture without drug selection was calculated with the following formula (where N=a relative copy number):

$$N_{37}=N_0\times(1-R)^{37}$$

Seven of ten tetR expressing cell lines showed a HAC loss rate (R<0.013) similar to non-regulated (e.g., usual) de novo HACs (R=0.001-0.015; Ikeno et al., *Nat. Biotechnol.* 16:431-439, 1998; Ohzeki et al., *J. Cell Biol.* 159, 765-775, 2002). In addition, three of ten tetR expressing cell lines showed increased instability of the HAC (R=0.025-0.044). Thus, tetR fusion protein binding to tetO alphoid HAC caused a mild increase in chromosome loss. It is possible that tetR binding may change some physical properties of the tetO alphoid sequence, which properties may be important for functional centromere assembly.

However, a significant loss of the tetO alphoid HAC was caused by tTA bindings (P=0.00014). Ten of 23 cell lines (43.5% of cells) showed a drastic loss of the HAC after 37 days culture without selective drug. The chromosome loss rates in those cell lines were remarkably high (R=0.27-0.3). Chromosome loss rates in eight cell lines (34.8%) were higher (R=0.015-0.1) than those of non-regulated (usual) de novo HACs. Five cell lines (21.7%) showed similar loss levels to those of usual de novo HACs (R<0.013). These results are consistent with the chromosome loss events observed cytologically on the individual transformants.

The copy number loss rate in each clone calculated from host chromosome X alphoid (R=−0.004~0.009) and chromosome 17 alphoid (R=−0.008~0.009) did not change with those of RFP-tetR expression cells (P>0.15 or 0.83, respectively). This result indicates that the drastic chromosome loss event was specific for the tetO alphoid HAC under conditions of tTA protein expression.

Without intending to be bound by any theory or mechanism, we propose that the extent of tetO dimer HAC loss by tTA varied among cell lines because: a) HAC loss events depend on tTA expression level in individual cell lines, and/or b) HAC loss events do not depend simply on tTA expression level. In the latter case, tTA expression alone might not be sufficient to change the chromatin structures on tetO alphoid HAC. When levels of tTA that assembled on the tetO alphoid HAC surpasses a threshold level, the balance of functional chromatin assembly on the tetO dimer HAC might not able to be maintained; thus these structures and the HAC might be lost. In both cases, the tetO alphoid HAC instability was clearly induced by tTA binding to tetO in the alphoid DNA insert.

All the results described above indicate that, on the stable tetO alphoid HAC, several distinctive chromatin structures were formed. Once the balance of those chromatin structures was changed by tTA binding to the tetO sequence in the alphoid insert on the HAC, it appears that the functional chromatin structure essential for chromosome stability may be easily lost.

In tTA expressing cells, lagging HAC signals in anaphase cells and HAC signals outside of interphase nuclei were frequently observed (FIG. 14). These results suggest that one result of tTA binding is that the tetO alphoid HAC might lose (or be reduced in) its mitotic stability and fail to segregate with the other chromosomes. Such an unstable HAC might be excluded from the nucleus containing the bulk of the chromosomes, forming an extremely tiny micronucleus. Such a small micronucleus might be deficient in formation of nuclear pores or other structures required for replication of the DNA within it. Therefore, the destabilized HAC would be lost from the cell population

Discussion

We succeeded in constructing a HAC using artificially designed alphoid DNA that includes a tetO sequence. The formation efficiency of the tetO alphoid based construct is somewhat decreased as compared with controls, which indicates that some sequence and/or property of alphoid DNA might be changed by the tetO insertion. Once formed, however, the tetO alphoid HACs were stably maintained in host cells, indicating that tetO sequence does not prevent proper HAC segregation during mitotic divisions. On the formed HACs, the tetO sequence did not inhibit or undermine stability of the HAC. Centromere chromatin (CENP-A, -B, -C and -H), transcriptionally competent chromatin (H3K4me2, H3K4me3), and heterochromatin (H3K9me3) were formed on the tetO alphoid HAC as well as on the HAC derived from wt 11-mer alphoid BAC.

TetO alphoid HACs tend to form transcriptional competent chromatin structure (rich in H3K4me2). Despite the inclusion of tetO sequence, the resultant HAC was functional for formation of chromatin structures. This result suggests that these chromatins were essential for HAC stability as a chromosome. Notably, tetO alphoid DNA repeat and BAC vector had an ability to form these chromatin structures autonomously.

This example clearly demonstrates that tetR binds to the tetO sequence included in the HACs. TetR assembly to tetO sequence of tetO alphoid HAC occurred in a doxycycline dependent manner. Because it exhibits accurate tetR binding, tetO alphoid HAC is useful for assays and systems that employ tetR-fusion proteins.

tetR-VP16 binding to the tetO dimer HAC drastically decreased HAC stability. Thus, HAC destabilization can be intentionally induced by the induction of open chromatin, without any change of DNA sequence. This suggests that linear DNA information of a HAC candidate (e.g., an alphoid DNA-containing BAC) is sufficient to form chromatin structures required for chromosome stability, but the important influence appears to be the balance between those chromatins. Therefore, once that balance was changed by (in this example) tTA binding, the HAC could not retain its entire structure as a stable chromosome and loss occurred. This feature can be exploited to generate regulated (conditional) chromosomes.

This example also describes the first example of changing the function of a centromere, and thereby the stability of a chromosome, in higher eukaryote without any drug or toxic materials treatment affecting cell viability. This indicates the tetO alphoid HACs are useful as marker chromosomes that exhibit conditional chromosome stability.

This disclosure provides methods for generating long synthetic centromeric tandem repeats, which are sufficient and effective as centromeric regions that support maintenance of mammalian (e.g., human) artificial chromosomes in vivo. The disclosure further provides MACs and HACs generated using such long synthetic centromeric tandem repeats (including for instance tet operator (tetO) containing synthetic repeats) and methods of using such in various applications. It will be apparent that the precise details of the compositions, materials, and methods described may be varied or modified without departing from the spirit of the described invention. We claim all such modifications and variations that fall within the scope and spirit of the claims below.

The invention claimed is:

1. A method of generating a mammalian artificial chromosome (MAC) having a regulated centromere, comprising:

assembling one or more engineered centromeric sequences into a vector, wherein the engineered centromeric sequence comprises (1) at least one mammalian repeat sequence comprising an alphoid repeat sequence, a mouse minor satellite sequence or a synthetic sequence at least 90% identical to such a repeat sequence; and (2) a tet Operator (tetO) sequence wherein binding of a transactivator to the tetO sequence disrupts the function of the centromere of the MAC.

2. The method of claim 1, wherein assembling one or more engineered centromeric sequences comprises homologous in vivo recombination.

3. The method of claim 2, wherein the homologous in vivo recombination is yeast homologous recombination.

4. The method of claim 2, wherein the vector is a transformation-associated recombination (TAR) vector comprising:

a yeast cassette, comprising:
a yeast origin of replication; and
a yeast selectable marker sequence;
a mammalian marker sequence; and
a sequence containing hooks homologous to sequence within the mammalian repeat sequence.

5. The method of claim 4, wherein the hooks comprise at least 30 contiguous nucleotides at least 90% homologous to a sequence selected from an alphoid repeat, or a mouse minor satellite.

6. The method of claim 4, wherein the TAR vector further comprises:

a bacterial origin of replication; and
a bacterial selectable marker sequence.

7. The method of claim 1, wherein the engineered centromeric sequence is produced by rolling circle amplification (RCA) of a starting sequence to produce a RCA product which is the engineered centromeric sequence, wherein the RCA product is a mixture of different lengths of concatamerized repeat sequence.

8. The method of claim 7, wherein the RCA products:
average about 1 to about 5 kb in length;
average about 1 to about 10 kb in length;
average more than 2 kb in length;
average about 5 kb in length; or
average more than 5 kb in length.

9. The method of claim 7, wherein the number of RCA products assembled into the artificial chromosome form a centromeric region of:
at least 10 kb;
at least 20 kb;
at least 50 kb;
at least 70 kb;
at least 80 kb;
at least 100 kb; or
more than 100 kb.

10. A method of making a mammalian artificial chromosome having a regulated centromere competent for maintenance in a mammalian cell, comprising:
selecting a starting sequence comprising (1) at least one mammalian repeat sequence comprising an alphoid repeat sequence, a mouse minor satellite sequence or a synthetic sequence at least 90% identical to such a repeat sequence; and (2) a tet Operator (tetO) sequence;
amplifying the starting sequence into a tandem repeat sequence using rolling-circle amplification; and
capturing the tandem repeat sequence in a nucleic acid molecule using in vivo homologous recombination to produce a mammalian artificial chromosome,
wherein the centromere of the mammalian artificial chromosome comprises the tandem repeat sequence, and
wherein the mammalian artificial chromosome is competent for maintenance in a mammalian cell; and wherein binding of a transactivator to the tetO sequence disrupts the function of the centromere of the MAC.

11. The method of claim 10, wherein the nucleic acid molecule is a TAR vector.

12. A mammalian artificial chromosome (MAC), made by the method of claim 1.

13. The MAC of claim 12, further comprising an expression cassette containing at least one mammalian protein encoding sequence.

14. A mammalian artificial chromosome (MAC), made by the method of claim 10.

15. The MAC of claim 14, further comprising an expression cassette containing at least one mammalian protein encoding sequence.

16. The method of claim 10, wherein amplifying the starting sequence into a tandem repeat sequence using rolling-circle amplification comprises producing a RCA product comprising the tandem repeat sequence amplified from the starting sequence using rolling-circle amplification, wherein the RCA product is a mixture of different lengths of concatamerized starting sequence.

17. The method of claim 16, wherein the RCA products:
average about 1 to about 5 kb in length;
average about 1 to about 10 kb in length;
average more than 2 kb in length;
average about 5 kb in length; or
average more than 5 kb in length.

18. The method of claim 16, wherein the number of RCA products assembled into the artificial chromosome form a centromeric region of:
at least 10 kb;
at least 20 kb;
at least 50 kb;
at least 70 kb;
at least 80 kb;
at least 100 kb; or
more than 100 kb.

* * * * *